United States Patent
Blaschke-Bonkowsky et al.

(10) Patent No.: US 10,421,991 B2
(45) Date of Patent: Sep. 24, 2019

(54) RAPID EPIDEMIOLOGIC TYPING OF BACTERIA

(71) Applicants: BioFire Diagnostics, LLC, Salt Lake City, UT (US); University of Utah Research Foundation, Salt Lake City, UT (US)

(72) Inventors: Anne Jeannette Blaschke-Bonkowsky, Salt Lake City, UT (US); Mark Aaron Poritz, Salt Lake City, UT (US)

(73) Assignees: BioFire Diagnostics, LLC, Salt Lake City, UT (US); University of Utah Research Foundation, Salt Lake City, UT (US)

( * ) Notice: Subject to any disclaimer, the term of this patent is extended or adjusted under 35 U.S.C. 154(b) by 438 days.

(21) Appl. No.: 14/938,242

(22) Filed: Nov. 11, 2015

(65) Prior Publication Data

US 2016/0153034 A1    Jun. 2, 2016

Related U.S. Application Data

(63) Continuation of application No. 12/467,654, filed on May 18, 2009, now Pat. No. 9,200,329.

(60) Provisional application No. 61/054,357, filed on May 19, 2008.

(51) Int. Cl.
| | |
|---|---|
| *C12P 19/34* | (2006.01) |
| *C12Q 1/6848* | (2018.01) |
| *C12Q 1/686* | (2018.01) |
| *C12Q 1/689* | (2018.01) |

(52) U.S. Cl.
CPC ......... *C12Q 1/6848* (2013.01); *C12Q 1/686* (2013.01); *C12Q 1/689* (2013.01); *C12Q 2600/156* (2013.01); *C12Q 2600/16* (2013.01)

(58) Field of Classification Search
USPC .......... 435/6.1, 6.11, 6.12, 91.1, 91.2, 91.51, 435/183; 436/94, 501; 536/23.1, 24.3, 536/24.33, 25.32
See application file for complete search history.

(56) References Cited

U.S. PATENT DOCUMENTS 7,255,992 B2    8/2007 Ecker et al.

OTHER PUBLICATIONS

Larionov et al., A standard curve based method for relative real time PCR data processing. BMC Bioinformatics, 6, 62, 2005.*
Bocchini et al. "Panton-Valentine Leukocidin Genes Are Associated With Enhanced Inflammatory Response and Local Disease in Acute Hematogenous *Staphylococcus aureus* Osteomyelitis in Children" *Pediatrics* 117:433-440 (2006).

(Continued)

*Primary Examiner* — Frank W Lu
(74) *Attorney, Agent, or Firm* — Myers Bigel, P.A.

(57) ABSTRACT

Methods for typing a strain of an organism are provided, the methods comprising the steps of amplifying, in a single reaction mixture containing nucleic acid from the organism, dividing the reaction mixture into a plurality of sets of second-stage reaction wells, each set of second-stage reaction wells containing a different pair of second-stage primers, subjecting each of the second-stage reaction wells to amplification conditions to generate a plurality of second-stage amplicons, melting the second-stage amplicons to generate a melting curve for each second-stage amplicon, and identifying the strain of the organism from the melting curves.

5 Claims, 32 Drawing Sheets

Specification includes a Sequence Listing.

(56) References Cited

OTHER PUBLICATIONS

Boye et al. "A new multiplex PCR for easy screening of methicillin-resistant *Staphylococcus aureus* SCCmec types I-V" *Clinical Microbiology and Infection* 13:725-727 (2007).
Bradford, Patricia A. "Extended-Spectrum β-Lactamases in the 21$^{st}$ Century: Characterization, Epidemiology, and Detection of This Important Resistance Threat" *Clinical Microbiology Reviews* 14(4):933-951 (2001).
Chongtrakool et al. "Staphylococcal Cassette Chromosome mec (SCCmec) Typing of Methicillin-Resistant *Staphylococcus aureus* Strains Isolated in 11 Asian Countries: a Proposal for a New Nomenclature for SCCmec Elements" *Antimicrobial Agents and Chemotherapy* 50(3):1001-1012 (2006).
Cookson et al. "Evaluation of Molecular Typing Methods in Characterizing a European Collection of Epidemic Methicillin-Resistant *Staphylococcus aureus* Strains: the HARMONY Collection" *Journal of Clinical Microbiology* 45(6):1830-1837 (2007).
Cuny et al. "PCR for the identification of methicillin-resistant *Staphylococcus aureus* (MRSA) strains using a single primer pair specific for SCCmec elements and the neighbouring chromosome-borne orfX" *Clinical Microbiology and Infection* 11:834-837 (2005).
Deurenberg et al. "Rapid detection of Panton-Valentine leukocidin from clinical isolates of *Staphylococcus aureus* strains by real-time PCR" *FEMS Microbiology Letters* 240:225-228 (2004).
Deurenberg et al. "The molecular evolution of methicillin-resistant *Staphylococcus aureus*" *Clinical Microbiology and Infection* 13:222-235 (2007).
Diep et al. "Roles of 34 Virulence Genes in the Evolution of Hospital- and Community-Associated Strains of Methicillin-Resistant *Staphylococcus aureus*" *The Journal of Infectious Diseases* 193:1495-1503 (2006).
Dobrowolski et al. "Real time PCR assays to detect common mutations in the biotinidase gene and application of mutational analysis to newborn screening for biotinidase deficiency" *Molecular Genetics and Metabolism* 78:100-107 (200.
Dobrowolski et al. "Validation of Dye-Binding/High-Resolution Thermal Denaturation for the Identification of Mutations in the SLC22A5 Gene" *Human Mutation* 25:306-313 (2005).
Elnifro et al. "Multiplex PCR: Optimization and Application in Diagnostic Virology" *Clinical Microbiology Reviews* 13(4):559-570 (2000).
Elnifro et al. "Multiplex Polymerase Chain Reaction for Diagnosis of Viral and Chlamydial Keratoconjunctivitis" *Investigative Ophthalmology & Visual Science* 41:1818-1822 (2000).
Enright et al. "Multilocus sequence typing" *Trends in Microbiology* 7(12):482-487 (1999).
Enright et al. "Multilocus Sequence Typing for Characterization of Methicillin-Resistant and Methicillin-Susceptible Clones of *Staphylococcus aureus*" *Journal of Clinical Microbiology* 38(3):1008-1015 (2000).
Fosheim et al. "Evaluation of the AdvanDx VRE EVIGENE Assay for Detection of vanA in Vancomycin-Resistant *Staphylococcus aureus*" *Journal of Clinical Microbiology* 45(5):1611-1613 (2007).
Francois et al. "A Novel Multiplex Real-Time PCR Assay for Rapid Typing of Major Staphylococcal Cassette Chromosome mec Elements" *Journal of Clinical Microbiology* 42(7):3309-3312 (2004).
Giaever et al. "Genomic profiling of drug sensitivities via induced haploinsufficiency" *Nature Genetics* 21:278-283 (1999).
Hagen et al. "Development of a real-time PCR assay for rapid identification of methicillin-resistant *Staphylococcus aureus* from clinical samples" *International Journal of Medical Microbiology* 295:77-86 (2005).
Hiramatsu, Keiichi "Vancomycin resistance in Staphylococci" *Drug Resistance Updates* 1:135-150 (1998).
Huletsky et al. "New Real-Time PCR Assay for Rapid Detection of Methicillin-Resistant *Staphylococcus aureus* Directly from Specimens Containing a Mixture of Staphylococci" *Journal of Clinical Microbiology* 42(5):1875-1884 (2004).
Johnsson et al. "Detection of Panton-Valentine leukocidin gene in *Staphylococcus aureus* by LightCycler PCR: clinical and epidemiological aspects" *Clinical Microbiology and Infection* 10:884-889 (2004).
Ma et al. "Predominance of Clones Carrying Panton-Valentine Leukocidin Genes among Methicillin-Resistant *Staphylococcus aureus* Strains Isolated in Japanese Hospitals from 1979 to 1985" *Journal of Clinical Microbiology* 44(12):4515-4527 (2006).
McKinney et al. "Rapid, comprehensive screening of the human medium chain acyl-CoA dehydrogenase gene" *Molecular Genetics and Metabolism* 82:112-120 (2004).
Milheiriço et al. "Update to the Multiplex PCR Strategy for Assignment of mec Element Types in *Staphylococcus aureus*" *Antimicrobial Agents and Chemotherapy* 51(9):3374-3377 (2007).
Oliveira et al. "Multiplex PCR Strategy for Rapid Identification of Structural Types and Variants of the mec Element in Methicillin-Resistant *Staphylococcus aureus*" *Antimicrobial Agents and Chemotherapy* 46():2155-2161 (2002).
Palais et al. "Quantitative heteroduplex analysis for single nucleotide polymorphism genotyping" *Analytical Biochemistry* 346:167-175 (2005).
Paterson, David L. "Resistance in gram-negative bacteria: Enterobacteriaceae" *American Journal of Infection Control* 34(5)(Supplement I):S20-S28 (2006).
"Plasmid, definition of Wikipedia" (8 pages)(Printed on Sep. 25, 2011).
Reed et al. "High-resolution DNA melting analysis for simple and efficient molecular diagnostics" *Pharmacogenomics* 8(6):597-608 (2007).
Sanchez et al. "A multiplex assay with 52 single nucleotide polymorphisms for human identification" *Electrophoresis* 27:1713-1724 (2006).
Stamper et al. "Clinical Validation of the Molecular BD GeneOhm StaphSR Assay for Direct Detection of *Staphylococcus aureus* and Methicillin-Resistant *Staphylococcus aureus* in Positive Blood Cultures" *Journal of Clinical Microbiology* 45(7):2191-2196 (2007).
Van Leeuwen et al. "Multilocus Sequence Typing of *Staphylococcus aureus* with DNA Array Technology" *Journal of Clinical Microbiology* 41(7):3323-3326 (2003).
Vandenesch et al. "Community-Acquired Methicillin-Resistant *Staphylococcus aureus* Carrying Panton-Valentine Leukocidin Genes: Worldwide Emergence" *Emerging Infectious Diseases* 9(8):978-984 (2003).
Vandersteen et al. "Identifying Common Genetic Variants by High-Resolution Melting" *Clinical Chemistry* 53(7):1191-1198 (2007).
Winzeler et al. "Functional Characterization of the *S. cerevisiae* Genome by Gene Deletion and Parallel Analysis" *Science* 285:901-906 (1999).
Wittwer et al. "Minimizing the Time Required for DNA Amplification by Efficient Heat Transfer to Small Samples" *Analytical Biochemistry* 186:328-331 (1990).
Wittwer et al. "Rapid Cycle DNA Amplification: Time and Temperature Optimization" *BioTechniques* 10(1): 76-83 (1991).
Wittwer et al. "Continuous Fluorescence Monitoring of Rapid Cycle DNA Amplification" *BioTechniques* 22:130-138 (1997).
Wittwer et al. "The LightCycler™: A Microvolume Multisample Fluorimeter with Rapid Temperature Control" *BioTechniques* 22(1):176-181 (1997).
Wittwer et al. "High-Resolution Genotyping by Amplicon Melting Analysis Using LCGreen" *Clinical Chemistry* 49(6):853-860 (2003).
Zhang et al. "Novel Multiplex PCR Assay for Characterization and Concomitant Subtyping of Staphylococcal Cassette Chromosome mec Types I to V in Methicillin-Resistant *Staphylococcus aureus*" *Journal of Clinical Microbiology* 43(10):5026-5033 (2005).
Zhou et al. "Closed-Tube Genotyping with Unlabeled Oligonucleotide Probes and a Saturating DNA Dye" *Clinical Chemistry* 50(8):1328-1335 (2004).

* cited by examiner

RAPID EPIDEMIOLOGIC TYPING OF BACTERIA

PRIORITY

This application is a continuation application of, and claims priority to, U.S. application Ser. No. 12/467,654 filed on May 18, 2009 and issued as U.S. Pat. No. 9,200,329 on Dec. 1, 2015, which claims priority to U.S. Provisional Patent Application Ser. No. 61/054,357 filed on May 19, 2008, and titled Rapid Epidemiologic Typing of Bacteria, the entire contents of each of which are incorporated by reference herein.

GOVERNMENT INTEREST

This invention was made with government support under Grant Nos. U01 AI061611, K12 HD001410, and R43 AI063695 awarded by National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 1267-6TSCT_ST25.txt, 17,396 bytes in size, generated on Jan. 20, 3016 and filed via EFS-Web, is provided in lieu of a paper copy. This Sequence Listing is incorporated by reference into the specification for its disclosures.

BACKGROUND OF THE INVENTION

In the United States, Canada, and Western Europe infectious disease accounts for approximately 7% of human mortality, while in developing regions infectious disease accounts for over 40% of human mortality. Infectious diseases lead to a variety of clinical manifestations. Among common overt manifestations are fever, pneumonia, meningitis, diarrhea, and diarrhea containing blood. While the physical manifestations suggest some pathogens and eliminate others as the etiological agent, a variety of potential causative agents remain, and clear diagnosis often requires a variety of assays be performed. Traditional microbiology techniques for diagnosing pathogens can take days or weeks, often delaying a proper course of treatment.

In recent years, the polymerase chain reaction (PCR) has become a method of choice for rapid diagnosis of infectious agents. PCR can be a rapid, sensitive, and specific tool to diagnose infectious disease. A challenge to using PCR as a primary means of diagnosis is the variety of possible causative organisms and the low levels of organism present in some pathological specimens. It is often impractical to run large panels of PCR assays, one for each possible causative organism, most of which are expected to be negative. The problem is exacerbated when pathogen nucleic acid is at low concentration and requires a large volume of sample to gather adequate reaction templates. In some cases there is inadequate sample to assay for all possible etiological agents. A solution is to run "multiplex PCR" wherein the sample is concurrently assayed for multiple targets in a single reaction. While multiplex PCR has proved to be valuable in some systems, shortcomings exist concerning robustness of high level multiplex reactions and difficulties for clear analysis of multiple products. To solve these problems, the assay may be subsequently divided into multiple secondary PCRs. Nesting secondary reactions within the primary product increases robustness. However, this further handling can be expensive and may lead to contamination or other problems.

Similarly, immuno-PCR ("iPCR") has the potential for sensitive detection of a wide variety of antigens. However, because traditional ELISA techniques have been applied to iPCR, iPCR often suffers from contamination issues that are problematic using a PCR-based detection method.

The present invention addresses various issues of contamination in biological analysis.

SUMMARY OF THE INVENTION

Accordingly, methods for identifying an organism or typing a strain of the organism are provided, comprising the steps of: (a) obtaining a sample of the organism, (b) amplifying, in a single reaction mixture containing nucleic acid from the organism, a plurality of first-stage amplicons using pairs of first-stage primers, the pairs of first-stage primers designed to hybridize to genomic regions of the organism that are specific to that organism, (c) dividing the reaction mixture into a plurality of sets of second-stage reaction wells, each set of second-stage reaction wells containing a different pair of second-stage primers, (d) subjecting each of the second-stage reaction wells to amplification conditions to generate a plurality of second-stage amplicons, (e) melting the second-stage amplicons to generate a melting curve for each second-stage amplicon, and (f) identifying the organism or strain from the melting curves.

In another illustrative aspect, methods for identifying a plasmid-borne genes in an organism are provided, comprising the steps of (a) obtaining a sample of the organism, (b) amplifying, in a single reaction mixture containing nucleic acid from the organism, a plurality of first-stage amplicons using pairs of first-stage primers, the pairs of first-stage primers designed to hybridize to plasmid-based sequences, (c) dividing the reaction mixture into a plurality of sets of second-stage reaction wells, each set of second-stage reaction wells containing a different pair of second-stage primers, (d) subjecting each of the second-stage reaction wells to amplification conditions to generate a plurality of second-stage amplicons, (e) melting the second-stage amplicons to generate a melting curve for each second-stage amplicon, and (f) identifying the strain of the organism from the melting curves.

Additional features of the present invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 15A shows that second-stage primers specific for either the rpoB or gyrB gene of Pa amplify only from the Pa template, except for a minor amplification with Ec in late cycles.

FIG. 15B shows that the rpoB "enteric" second-stage primer amplifies Ec, Kp and Ko, but for the gyrB gene a specific primer targets only Kp.

FIG. 15C shows that second-stage primers specific for either the rpoB or gyrB gene of Hi amplify only from the Hi template, except for a minor amplification with Ko near the end of the reaction.

FIG. 17A shows the results from the rpoB gene, while FIG. 17B shows the results from the gyrB gene.

FIG. 18A shows amplification of the gyrB gene, while FIG. 18B shows the results for the rpoB gene for this target.

FIG. 19A shows amplification using the "pan-enteric" primers, FIG. 1913 shoes amplification using *E. coli* preferential primers, FIG. 19C shows amplification using *K. pneumoniae* primers, and FIG. 19D shows amplification using *E. cloacae* primers.

FIG. 20A is a table showing illustrative Cp cut-off values, and FIG. 20B shows a flow-chart using the values of FIG. 20A.

FIG. 21A shows the results for exon 1, in which all patients were homozygous for a single allele; no heteroduplexes were formed during melting and all curves matched the control. FIG. 21B shows exon 5, in which one patient had a heterozygous single nucleotide change from T to C, easily observable here by the early melting heteroduplex (curve shifted to the left).

FIG. 23A shows melting curves normalized by the LightScanner software to highlight differences. When compared in this manner, the melting curves of A+X and B+X are shown to be different from the melting curve of X alone. C+X, however, has exactly the same melting properties as X alone, suggesting that these isolates have the same sequence at this locus (allele X=allele C). FIG. 23B shows a "difference plot" generated by the LightScanner software and used to magnify melting curve differences for easier visualization. In this type of analysis, one melting curve is designated as the reference allele, and the difference in fluorescence of the reference and another allele are plotted at each temperature. In the difference plot shown here, the unknown X is designated as the reference, and relative differences are shown. Melting curves from A+X and B+X again show significant differences when compared to X alone; no difference is seen in C+X vs X alone, suggesting that X and C are highly similar, if not identical, in sequence.

DETAILED DESCRIPTION

The self-contained nucleic acid analysis pouches described herein may be used to assay a sample for the presence of various biological substances, illustratively antigens and nucleic acid sequences, illustratively in a single closed system. In one embodiment, the pouch is used to assay for multiple pathogens. Illustratively, various steps may be performed in the optionally disposable pouch, including nucleic acid preparation, primary large volume multiplex PCR, dilution of primary amplification product, and secondary PCR, culminating with real-time detection and/or post-amplification analysis such as melting-curve analysis. It is understood, however, that pathogen detection is one exemplary use and the pouches may be used for other nucleic acid analysis or detection of other substances, including but not limited to peptides, toxins, and small molecules. Further, it is understood that while the various steps may be performed in pouches of the present invention, one or more of the steps may be omitted for certain uses, and the pouch configuration may be altered accordingly.

While PCR is the amplification method used in the examples herein, it is understood that any amplification method that uses a primer may be suitable. Such suitable procedures include polymerase chain reaction (PCR); strand displacement amplification (SDA); nucleic acid sequence-based amplification (NASBA); cascade rolling circle amplification (CRCA), loop-mediated isothermal amplification of DNA (LAMP); isothermal and chimeric primer-initiated amplification of nucleic acids (ICAN); target based-helicase dependant amplification (HDA); transcription-mediated amplification (TMA), and the like. Therefore, when the term PCR is used, it should be understood to include other alternative amplification methods. It is understood that protocols may need to be adjusted accordingly.

Figure 1:
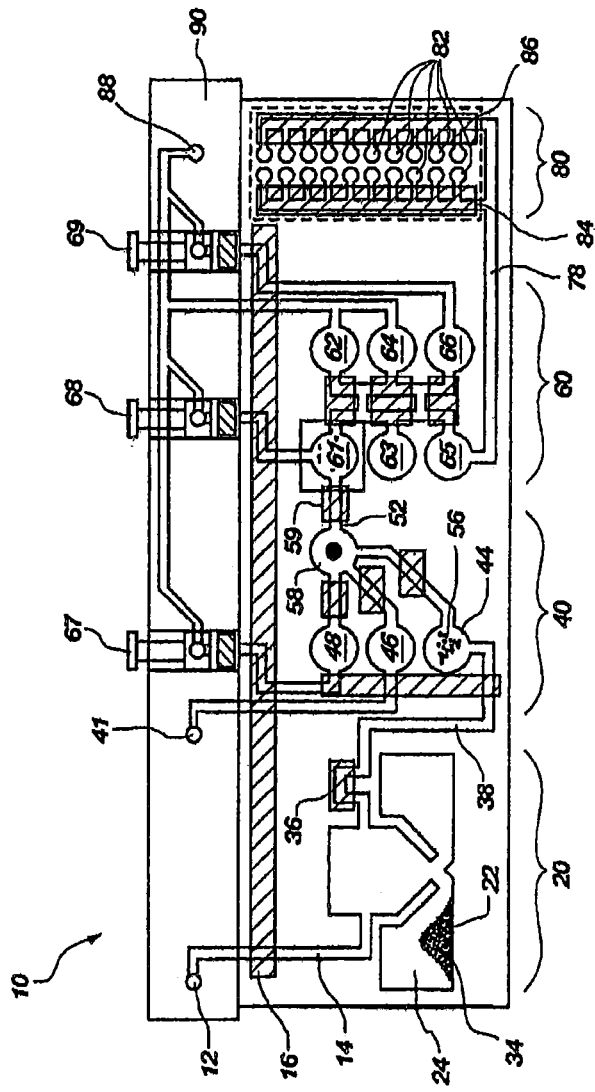
FIG. 1 shows a flexible pouch according to one embodiment of this invention.

FIG. 1 shows an illustrative self-contained nucleic acid analysis pouch 10. Pouch 10 has a cell lysis zone 20, a nucleic acid preparation zone 40, a first-stage amplification zone 60, and a second-stage amplification zone 80. A sample containing nucleic acid is introduced into the pouch 10 via sample injection port 12. Pouch 10 comprises a variety of channels and blisters of various sizes and is arranged such that the sample flows through the system. The sample passes through the various zones and is processed accordingly.

Sample processing occurs in various blisters located within pouch 10. Various channels are provided to move the sample within and between processing zones, while other channels are provided to deliver fluids and reagents to the sample or to remove such fluids and reagents from the sample. Liquid within pouch 10 illustratively is moved between blisters by pressure, illustratively pneumatic pressure, as described below, although other methods of moving material within the pouch are contemplated.

While other containers may be used, illustratively, pouch 10 is formed of two layers of a flexible plastic film or other flexible material such as polyester, polyethylene terephthalate (PET), polycarbonate, polypropylene, polymethylmethacrylate, and mixtures thereof that can be made by any process known in the art, including extrusion, plasma deposition, and lamination. Metal foils or plastics with aluminum lamination also may be used. Other barrier materials are known in the art that can be sealed together to form the blisters and channels. If plastic film is used, the layers may be bonded together, illustratively by heat sealing. Illustratively, the material has low nucleic acid binding capacity.

For embodiments employing fluorescent monitoring, plastic films that are adequately low in absorbance and auto-fluorescence at the operative wavelengths are preferred. Such material could be identified by trying different plastics, different plasticizers, and composite ratios, as well as different thicknesses of the film. For plastics with aluminum or other foil lamination, the portion of the pouch that is to be read by a fluorescence detection device can be left without the foil. For example, if fluorescence is monitored in the blisters 82 of the second stage amplification zone 80 of pouch 10, then one or both layers at blisters 82 would be left without the foil. In the example of PCR, film laminates composed of polyester (Mylar, Dupont, Wilmington Del.) of about 0.0048 inch (0.1219 mm) thick and polypropylene films of 0.001-0.003 inch (0.025-0.076 mm) thick perform well. Illustratively, pouch 10 is made of a clear material capable of transmitting approximately 80%-90% of incident light.

In the illustrative embodiment, the materials are moved between blisters by the application of pressure, illustratively pneumatic pressure, upon the blisters and channels. Accordingly, in embodiments employing pneumatic pressure, the pouch material illustratively is flexible enough to allow the pneumatic pressure to have the desired effect. The term "flexible" is herein used to describe a physical characteristic of the material of pouch. The term "flexible" is herein defined as readily deformable by the levels of pneumatic pressure used herein without cracking, breaking, crazing, or the like. For example, thin plastic sheets, such as Saran™ wrap and Ziploc® bags, as well as thin metal foil, such as aluminum foil, are flexible. However, only certain regions of the blisters and channels need be flexible, even in embodiments employing pneumatic pressure. Further, only one side of the blisters and channels need to be flexible, as long as the blisters and channels are readily deformable. Other regions of the pouch 10 may be made of a rigid material or may be reinforced with a rigid material.

Illustratively, a plastic film is used for pouch 10. A sheet of metal, illustratively aluminum, or other suitable material, may be milled or otherwise cut, to create a die having a pattern of raised surfaces. When fitted into a pneumatic press (illustratively A-5302-PDS, Janesville Tool Inc., Milton Wis.), illustratively regulated at an operating temperature of 195° C., the pneumatic press works like a printing press, melting the sealing surfaces of plastic film only where the die contacts the film. Various components, such as PCR primers (illustratively spotted onto the film and dried), antigen binding substrates, magnetic beads, and zirconium silicate beads may be sealed inside various blisters as the pouch 10 is formed. Reagents for sample processing can be spotted onto the film prior to sealing, either collectively or separately. In one embodiment, nucleotide tri-phosphates (NTPs) are spotted onto the film separately from polymerase and primers, essentially eliminating activity of the polymerase until the reaction is hydrated by an aqueous sample. If the aqueous sample has been heated prior to hydration, this creates the conditions for a true hot-start PCR and reduces or eliminates the need for expensive chemical hot-start components. This separate spotting is discussed further below, with respect to FIG. 5C, but it is understood that such spotting may be used with any of the embodiments discussed herein.

Figure 2A:
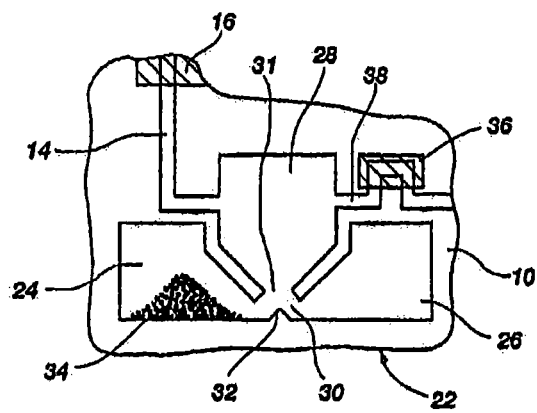
FIG. 2A shows an embodiment of the cell lysis zone of the flexible pouch according to FIG. 1.
Figure 2B:
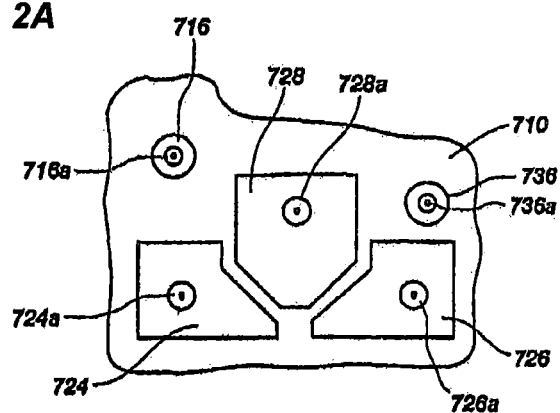
FIG. 2B shows an embodiment of a portion of a bladder corresponding to the cell lysis zone shown in FIG. 2A.

When pneumatic pressure is used to move materials within pouch 10, in one embodiment a "bladder" may be employed. The bladder assembly 710, a portion of which is shown in FIG. 2B, may be manufactured in a process similar to that of making the pouch, but individual blisters in the bladder assembly 710 include pneumatic fittings (illustratively fitting 724a) allowing individual bladders within the bladder assembly 710 to be pressurized by a compressed gas source. Because the bladder assembly is subjected to compressed gas and may be used multiple times, the bladder assembly may be made from tougher or thicker material than the pouch. Alternatively, bladders may be formed from a series of plates fastened together with gaskets, seals, valves, and pistons. Other arrangements are within the scope of this invention.

When pouch 10 is placed within the instrument, the pneumatic bladder assembly 710 is pressed against one face of the pouch 10, so that if a particular bladder is inflated, the pressure will force the liquid out of the corresponding blister in the pouch 10. In addition to pneumatic bladders corresponding to many of the blisters of pouch 10, the bladder assembly may have additional pneumatic actuators, such as bladders or pneumatically-driven pistons, corresponding to various channels of pouch 10. When activated, these additional pneumatic actuators form pinch valves to pinch off and close the corresponding channels. To confine liquid within a particular blister of pouch 10, the pinch valve pneumatic actuators are inflated over the channels leading to and from the blister, such that the actuators function as pinch valves to pinch the channels shut. Illustratively, to mix two volumes of liquid in different blisters, the pinch valve pneumatic actuator sealing the connecting channel is depressurized, and the pneumatic bladders over the blisters are alternately pressurized, forcing the liquid back and forth through the channel connecting the blisters to mix the liquid therein. The pinch valve pneumatic actuators may be of various shapes and sizes and may be configured to pinch off more than one channel at a time. Such an illustrative pinch valve is illustrated in FIG. 1 as pinch valve 16, which may be used to close all injection ports. While pneumatic actuators are discussed herein, it is understood that other ways of providing pressure to the pouch are contemplated, including various electromechanical actuators such as linear stepper motors, motor-driven cams, rigid paddles driven by pneumatic, hydraulic or electromagnetic forces, rollers, rocker-arms, and in some cases, cocked springs. In addition, there are a variety of methods of reversibly or irreversibly closing channels in addition to applying pressure normal to the axis of the channel. These include kinking the bag across the channel, heat-sealing, rolling an actuator, and a variety of physical valves sealed into the channel such as butterfly valves and ball valves. Additionally, small Peltier devices or other temperature regulators may be placed adjacent the channels and set at a temperature sufficient to freeze the fluid, effectively forming a seal. Also, while the design of FIG. 1 is adapted for an automated instrument featuring actuator elements positioned over each of the blisters and channels, it is also contemplated that the actuators could remain stationary, and the pouch could be transitioned in one or two dimensions such that a small number of actuators could be used for several of the processing stations including sample disruption, nucleic-acid capture, first and second-stage PCR, and other applications of the pouch such as immunoassay and immuno-PCR. Rollers acting on channels and blisters could prove particularly useful in a configuration in which the pouch is translated between stations. Thus, while pneumatic actuators are used in the presently disclosed embodiments, when the term "pneumatic actuator" is used herein, it is understood that other actuators and other ways of providing pressure may be used, depending on the configuration of the pouch and the instrument.

With reference to FIG. 1, an illustrative sample pouch 10 configured for nucleic acid extraction and multiplex PCR is provided. The sample enters pouch 10 via sample injection port 12 in fitment 90. Injector port 12 may be a frangible seal, a one-way valve, or other entry port. Vacuum from inside pouch 10 may be used to draw the sample into pouch 10, a syringe or other pressure may be used to force the sample into pouch 10, or other means of introducing the sample into pouch 10 via injector port 12 may be used. The sample travels via channel 14 to the three-lobed blister 22 of the cell lysis zone 20, wherein cells in the sample are lysed. Once the sample enters three-lobed blister 22, pinch valve 16 is closed. Along with pinch valve 36, which may have been already closed, the closure of pinch valve 16 seals the sample in three-lobed blister 22. It is understood that cell lysis may not be necessary with every sample. For such samples, the cell lysis zone may be omitted or the sample may be moved directly to the next zone. However, with many samples, cell lysis is needed. In one embodiment, bead-milling is used to lyse the cells.

Bead-milling, by shaking or vortexing the sample in the presence of lysing particles such as zirconium silicate (ZS) beads 34, is an effective method to form a lysate. It is understood that, as used herein, terms such as "lyse," "lysing," and "lysate" are not limited to rupturing cells, but that such terms include disruption of non-cellular particles, such as viruses. FIG. 2A displays one embodiment of a cell lysis zone 20, where convergent flow creates high velocity bead impacts, to create lysate. Illustratively, the two lower lobes 24, 26 of three-lobed blister 22 are connected via channel 30, and the upper lobe 28 is connected to the lower lobes 24, 26 at the opposing side 31 of channel 30. FIG. 2B shows a counterpart portion of the bladder assembly 710 that would be in contact with the cell lysis zone 20 of the pouch 10. When pouch 10 is placed in an instrument, adjacent each lobe 24, 26, 28 on pouch 10 is a corresponding pneumatic bladder 724, 726, 728 in the bladder assembly 710. It is understood that the term "adjacent," when referring to the relationship between a blister or channel in a pouch and its corresponding pneumatic actuator, refers to the relationship between the blister or channel and the corresponding pneumatic actuator when the pouch is placed into the instrument. In one embodiment, the pneumatic fittings 724a, 726a of the two lower pneumatic bladders 724, 726 adjacent lower lobes 24, 26 are plumbed together. The pneumatic fittings 724a, 726a and the pneumatic fitting 728a of upper pneumatic bladder 728 adjacent upper lobe 28 are plumbed to the opposing side of an electrically actuated valve configured to drive a double-acting pneumatic cylinder. Thus configured, pressure is alternated between the upper pneumatic bladder 728 and the two lower pneumatic bladders 724, 726. When the valve is switched back and forth, liquid in pouch 10 is driven between the lower lobes 24, 26 and the upper lobe 28 through a narrow nexus 32 in channel 30. As the two lower lobes 24, 26 are pressurized at the same time, the flow converges and shoots into the upper lobe 28. Depending on the geometry of the lobes, the collision velocity of beads 34 at the nexus 32 may be at least about 12 m/sec, providing high-impact collisions resulting in lysis. The illustrative three-lobed system allows for good cell disruption and structural robustness, while minimizing size and pneumatic gas consumption. While ZS beads are used as the lysing particles, it is understood that this choice is illustrative only, and that other materials and particles of other shapes may be used. It is also understood that other configurations for cell lysis zone 20 are within the scope of this invention.

While a three-lobed blister is used for cell lysis, it is understood that other multi-lobed configurations are within the scope of this invention. For instance, a four-lobed blister, illustratively in a cloverleaf pattern, could be used, wherein the opposite blisters are pressurized at the same time, forcing the lysing particles toward each other, and then angling off to the other two lobes, which then may be pressurized together. Such a four-lobed blister would have the advantage of having high-velocity impacts in both directions. Further, it is contemplated that single-lobed blisters may be used, wherein the lysing particles are moved rapidly from one portion of the single-lobed blister to the other. For example, pneumatic actuators may be used to close off areas of the single-lobed blister, temporarily forming a multi-lobed blister in the remaining areas. Other actuation methods may also be used such as motor, pneumatic, hydraulic, or electromagnetically-driven paddles acting on the lobes of the device. Rollers or rotary paddles can be used to drive fluid together at the nexus 32 of FIG. 2A, illustratively if a recirculation means is provided between the upper and lower lobes and the actuator provides peristaltic pumping action. Other configurations are within the scope of this invention.

Figure 12A:
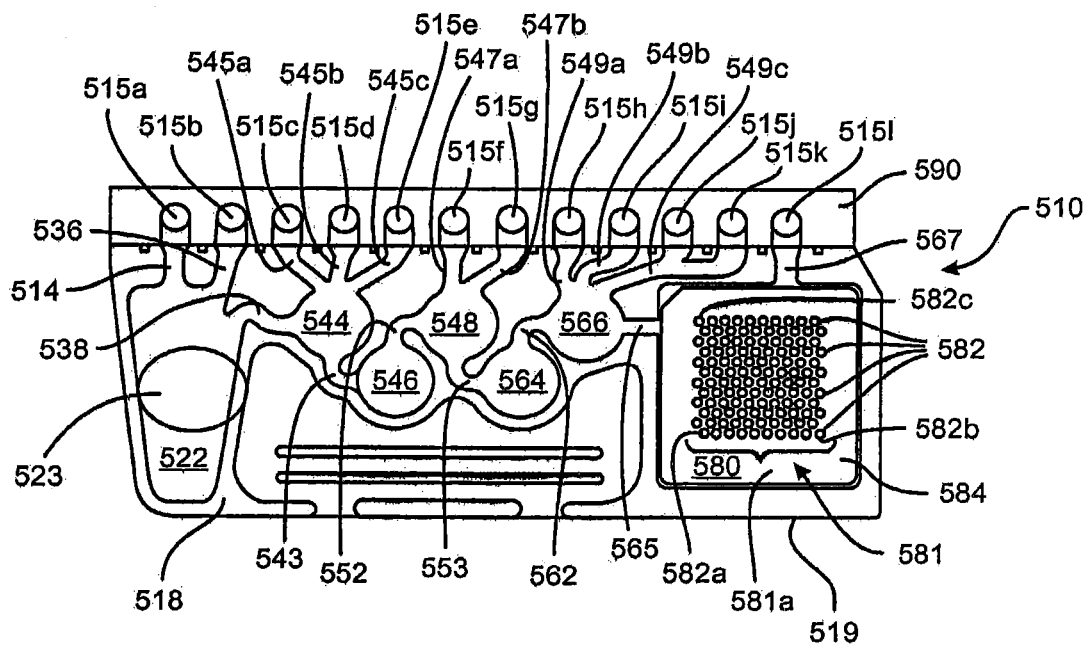
FIG. 12A is similar to FIG. 6A, except showing a pouch having a second-stage high density array.
Figure 12B:
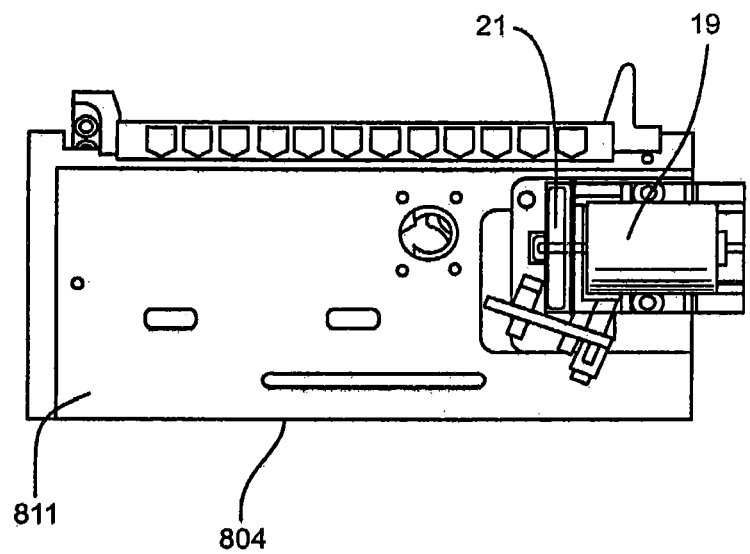
FIG. 12B shows a modification of a component of the instrument of FIG. 8. A support member has been provided with a motor configured for use with the pouch of FIG. 12A.

It may also be possible to move the sample and lysing particles quickly enough to effect lysis within a single-lobed lysis blister without temporarily forming a multi-lobed blister. In one such alternative embodiment, as shown in FIG. 2B, vortexing may be achieved by impacting the pouch with rotating blades or paddles 21 attached to an electric motor 19. The blades 21 may impact the pouch at the lysis blister or may impact the pouch near the lysis blister, illustratively at an edge 17 adjacent the lysis blister. In such an embodiment, the lysis blister may comprise one or more blisters. FIG. 12A shows an embodiment comprising one such lysis blister 522. FIG. 12B shows a bead beating motor 19, comprising blades 21 that may be mounted on a first side 811 of second support member 804, of instrument 800 shown in FIG. 8. It is understood, however, that motor 19 may be mounted on first support member 802 or on other structure of instrument 800.

FIG. 2B also shows pneumatic bladder 716 with pneumatic fitting 716a, and pneumatic bladder 736 with pneumatic fitting 736a. When the pouch 10 is placed in contact with bladder assembly 710, bladder 716 lines up with channel 12 to complete pinch valve 16. Similarly, bladder 736 lines up with channel 38 to complete pinch valve 36. Operation of pneumatic bladders 716 and 736 allow pinch valves 16 and 36 to be opened and closed. While only the portion of bladder assembly 710 adjacent the cell lysis zone is shown, it is understood that bladder assembly 710 would be provided with similar arrangements of pneumatic blisters to control the movement of fluids throughout the remaining zones of pouch 10.

Other prior art instruments teach PCR within a sealed flexible container. See, e.g., U.S. Pat. Nos. 6,645,758 and 6,780,617, and co-pending U.S. patent application Ser. No. 10/478,453, herein incorporated by reference. However, including the cell lysis within the sealed PCR vessel can improve ease of use and safety, particularly if the sample to be tested may contain a biohazard. In the embodiments illustrated herein, the waste from cell lysis, as well as that from all other steps, remains within the sealed pouch. However, it is understood that the pouch contents could be removed for further testing.

Figure 3:
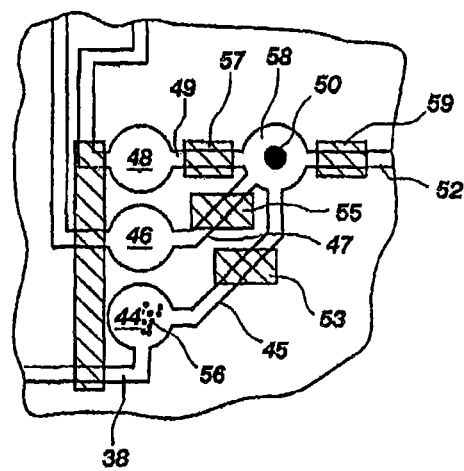
FIG. 3 shows an embodiment of the nucleic acid preparation zone of the flexible pouch according to FIG. 1.

Once the cells are lysed, pinch valve 36 is opened and the lysate is moved through channel 38 to the nucleic acid preparation zone 40, as best seen in FIG. 3, after which, pinch valve 36 is closed, sealing the sample in nucleic acid preparation zone 40. In the embodiment illustrated in FIG. 3, purification of nucleic acids takes the bead-milled material and uses affinity binding to silica-based magnetic-beads 56, washing the beads with ethanol, and eluting the nucleic acids with water or other fluid, to purify the nucleic acid from the cell lysate. The individual components needed for nucleic acid extraction illustratively reside in blisters 44, 46, 48, which are connected by channels 45, 47, 49 to allow reagent mixing. The lysate enters blister 44 from channel 38. Blister 44 may be provided with magnetic beads 56 and a suitable binding buffer, illustratively a high-salt buffer such as that of 1-2-3™ Sample Preparation Kit (Idaho Technology, Salt Lake City, Utah) or either or both of these components may be provided subsequently through one or more channels connected to blister 44. The nucleic acids are captured on beads 56, pinch valve 53 is then opened, and the lysate and beads 56 may be mixed by gentle pressure alternately on blisters 44 and 58 and then moved to blister 58 via pneumatic pressure illustratively provided by a corresponding pneumatic bladder on bladder assembly 710. The magnetic beads 56 are captured in blister 58 by a retractable magnet 50, which is located in the instrument adjacent blister 58, and waste may be moved to a waste reservoir or may be returned to blister 44 by applying pressure to blister 58. Pinch valve 53 is then closed. The magnetic beads 56 are washed with ethanol, isopropanol, or other organic or inorganic wash solution provided from blister 46, upon release of pinch valve 55. Optionally, magnet 50 may be retracted allowing the beads to be washed by providing alternate pressure on blisters 46 and 58. The beads 56 are once again captured in blister 58 by magnet 50, and the non-nucleic acid portion of the lysate is washed from the beads 56 and may be moved back to blister 46 and secured by pinch valve 55 or may be washed away via another channel to a waste reservoir. Once the magnetic beads are washed, pinch valve 57 is opened, releasing water (illustratively buffered water) or another nucleic acid eluant from blister 48. Once again, the magnet 50 may be retracted to allow maximum mixing of water and beads 56, illustratively by providing alternate pressure on blisters 48 and 58. The magnet 50 is once again deployed to collect beads 56. Pinch valve 59 is released and the eluted nucleic acid is moved via channel 52 to first-stage amplification zone 60. Pinch valve 59 is then closed, thus securing the sample in first-stage amplification zone 60.

It is understood that the configuration for the nucleic acid preparation zone 40, as shown in FIG. 3 and described above, is illustrative only, and that various other configurations are possible within the scope of the present disclosure.

The ethanol, water, and other fluids used herein may be provided to the blisters in various ways. The fluids may be stored in the blisters, the necks of which may be pinched off by various pinch valves or frangible portions that may be opened at the proper time in the sample preparation sequence. Alternatively, fluid may be stored in reservoirs in the pouch as shown pouch 110 in FIG. 5A, or in the fitment as discussed with respect to pouch 210 of FIG. 6A, and moved via channels, as necessary. In still another embodiment, the fluids may be introduced from an external source, as shown in FIG. 1, especially with respect to ethanol injection ports 41, 88 and plungers 67, 68, 69. Illustratively, plungers 67, 68, 69 may inserted into fitment 90, illustratively of a more rigid material, and may provide a measured volume of fluid upon activation of the plunger, as in U.S. patent application Ser. No. 10/512,255, herein incorporated by reference. The measured volume may be the same or different for each of the plungers. Finally, in yet another embodiment, the pouch may be provided with a measured volume of the fluid that is stored in one or more blisters, wherein the fluid is contained within the blister, illustratively provided in a small sealed pouch within the blister, effectively forming a blister within the blister. At the appropriate time, the sealed pouch may then be ruptured, illustratively by pneumatic pressure, thereby releasing the fluid into the blister of the pouch. The instrument may also be configured the provide some or all of the reagents directly through liquid contacts between the instrument and the fitment or pouch material provided that the passage of fluid is tightly regulated by a one-way valve to prevent the instrument from becoming contaminated during a run. Further, it will often be desirable for the pouch or its fitment to be sealed after operation to prohibit contaminating DNA to escape from the pouch. Various means are known to provide reagents on demand such as syringe pumps, and to make temporary fluid contact with the fitment or pouch, such as barbed fittings or o-ring seals. It is understood that any of these methods of introducing fluids to the appropriate blister may be used with any of the embodiments of the pouch as discussed herein, as may be dictated by the needs of a particular application.

As discussed above, nested PCR involves target amplification performed in two stages. In the first-stage, targets are amplified, illustratively from genomic or reverse-transcribed template. The first-stage amplification may be terminated prior to plateau phase, if desired. In the secondary reaction, the first-stage amplicons may be diluted and a secondary amplification uses the same primers or illustratively uses nested primers hybridizing internally to the primers of the first-stage product. Nested primers may be fully internal to the first-stage amplification primers, or there may be some overlap with the nested primers shifted in the 3'-direction. Advantages of nested PCR include: a) the initial reaction product forms a homogeneous and specific template assuring high fidelity in the secondary reaction, wherein even a relatively low-efficiency first-stage reaction creates adequate template to support robust second-stage reaction; b) non-specific products from the first-stage reaction do not significantly interfere with the second stage reaction, as different nested primers are used and the original amplification template (illustratively genomic DNA or reverse-transcription product) may be diluted to a degree that eliminates its significance in the secondary amplification; and c) nested PCR enables higher-order reaction multiplexing. First-stage reactions can include primers for several unique amplification products. These products are then identified in the second-stage reactions. However, it is understood that first-stage multiplex and second-stage singleplex is illustrative only and that other configurations are possible. For example, the first-stage may amplify a variety of different related amplicons using a single pair of primers, and second-stage may be used to target differences between the amplicons, illustratively using melting curve analysis.

Figure 4:
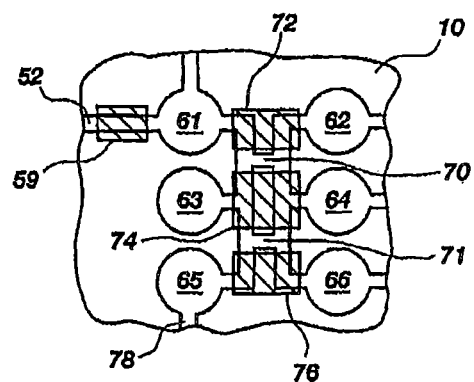
FIG. 4 shows an embodiment of the first-stage amplification zone of the flexible pouch according to FIG. 1.

Turning back to FIG. 1, the nucleic acid sample enters the first-stage amplification zone 60 via channel 52 and is delivered to blister 61. A PCR mixture, including a polymerase (illustratively a Taq polymerase), dNTPs, and primers, illustratively a plurality of pairs of primers for multiplex amplification, may be provided in blister 61 or may be introduced into blister 61 via various means, as discussed above. Alternatively, dried reagents may be spotted onto the location of blister 61 upon assembly of pouch 10, and water or buffer may be introduced to blister 61, illustratively via plunger 68, as shown in FIG. 1. As best seen in FIG. 4, the sample is now secured in blister 61 by pinch valves 59 and 72, and is thermocycled between two or more temperatures, illustratively by heat blocks or Peltier devices that are located in the instrument and configured to contact blister 61. However, it is understood that other means of heating and cooling the sample contained within blister 61, as are known in the art, are within the scope of this invention. Non-limiting examples of alternative heating/cooling devices for thermal cycling include having a air-cycled blister within the bladder, in which the air in the pneumatic blister adjacent blister 61 is cycled between two or more temperatures; or moving the sample to temperature zones within the blister 61, illustratively using a plurality of pneumatic presses, as in U.S. patent application Ser. No. 10/478,453, herein incorporated by reference, or by translating pouch 10 on an axis or providing pouch 10 with a rotary layout and spinning pouch 10 to move the contents between heat zones of fixed temperature.

Nucleic acids from pathogens are often co-isolated with considerable quantities of host nucleic acids. These host-derived nucleic acids often interact with primers, resulting in amplification of undesired products that then scavenge primers, dNTPs, and polymerase activity, potentially starving a desired product of resources. Nucleic acids from pathogenic organisms are generally of low abundance, and undesired product is a potential problem. The number of cycles in the first-stage reaction of zone 60 may be optimized to maximize specific products and minimize non-specific products. It is expected that the optimum number of cycles will be between about 10 to about 30 cycles, illustratively between about 15 to about 20 cycles, but it is understood that the number of cycles may vary depending on the particular target, host, and primer sequence.

Following the first-stage multiplex amplification, the first-stage amplification product is diluted, illustratively in incomplete PCR master mix, before fluidic transfer to secondary reaction sites.

FIG. 4 shows an illustrative embodiment for diluting the sample in three steps. In the first step, pinch valve 72 is opened and the sample undergoes a two-fold dilution by mixing the sample in blister 61 with an equal volume of water or buffer from blister 62, which is provided to blister 62, as well as blisters 64 and 66, as discussed above. Squeezing the volume back and forth between blisters 61, 62 provides thorough mixing. As above, mixing may be provided by pneumatic bladders provided in the bladder 710 and located adjacent blisters 61, 62. The pneumatic bladders may be alternately pressurized, forcing the liquid back and forth. During mixing, a pinch valve 74 prevents the flow of liquid into the adjacent blisters. At the conclusion of mixing, a volume of the diluted sample is captured in region 70, and pinch valve 72 is closed, sealing the diluted sample in region 70. Pinch valve 74 is opened and the sample is further diluted by water or buffer provided in either or both of blisters 63, 64. As above, squeezing the volume back and forth between blisters 63, 64 provides mixing. Subsequently, pinch valve 74 is closed, sealing a further diluted volume of sample in region 71. Final dilution takes place illustratively by using buffer or water provided in either or both of blisters 65, 66, with mixing as above. Illustratively this final dilution takes place using an incomplete PCR master mix (e.g., containing all PCR reagents except primers) as the fluid.

Optional heating of the contents of blister 66 prior to second-stage amplification can provide the benefits of hot-start amplification without the need for expensive antibodies or enzymes. It is understood, however, that water or other buffer may be used for the final dilution, with additional PCR components provided in second-stage amplification zone 80. While the illustrative embodiment uses three dilution stages, it is understood that any number of dilution stages may be used, to provide a suitable level of dilution. It is also understood that the amount of dilution can be controlled by adjusting the volume of the sample captured in regions 70 and 71, wherein the smaller the amount of sample captured in regions 70 and 71, the greater the amount of dilution or wherein additional aliquots captured in region 70 and/or region 71 by repeatedly opening and closing pinch valves 72 and 74 and/or pinch valves 74 and 76 may be used to decrease the amount of dilution. It is expected that about $10^{-2}$ to about $10^{-5}$ dilution would be suitable for many applications.

Success of the secondary PCR reactions is dependent upon template generated by the multiplex first-stage reaction. Typically, PCR is performed using DNA of high purity. Methods such as phenol extraction or commercial DNA extraction kits provide DNA of high purity. Samples processed through the pouch 10 may require accommodations be made to compensate for a less pure preparation. PCR may be inhibited by components of biological samples, which is a potential obstacle. Illustratively, hot-start PCR, higher concentration of taq polymerase enzyme, adjustments in $MgCl_2$ concentration, adjustments in primer concentration, and addition of adjuvants (such as DMSO, TMSO, or glycerol) optionally may be used to compensate for lower nucleic acid purity. While purity issues are likely to be more of a concern with first-stage amplification, it is understood that similar adjustments may be provided in the second-stage amplification as well.

While dilution and second-stage sample preparation are accomplished in the illustrative embodiment by retaining a small amount of amplified sample in the blisters and channels of the first-stage PCR portion of the pouch, it is understood that these processes may also be performed in other ways. In one such illustrative example, pre-amplified sample can be captured in a small cavity in a member, illustratively a translating or rotating member, able to move a fixed volume of sample from the first to the second-stage PCR reagent. A one microliter fraction of the pre-amplified sample, mixed with 100 microliters of fresh PCR reagent would yield a one-hundred-fold reduction in concentration. It is understood that this dilution is illustrative only, and that other volumes and dilution levels are possible. This approach could be accomplished by forcing the first-stage amplification product into the rigid fitment where it contacts one of the plungers 68 or 69 of FIG. 1. In such an embodiment, the plunger would be configured to carry a small fraction of the sample into contact with the adjacent dilution buffer or second-stage PCR buffer. Similarly a sliding element could be used to carry a small amount of the first-stage amplification product into contact with the second-stage reaction mix while maintaining a seal between the stages, and containing the amplified sample within the rigid fitment 90.

Subsequent to first-stage PCR and dilution, channel 78 transfers the sample to a plurality of low volume blisters 82 for secondary nested PCR. In one illustrative embodiment, dried primers provided in the second-stage blisters are resuspended by the incoming aqueous material to complete the reaction mixture. Optionally, fluorescent dyes such as LCGreen® Plus (Idaho Technology, Salt Lake City, Utah) used for detection of double-stranded nucleic acid may be provided in each blister or may be added to the incomplete PCR master mix provided at the end of the serial dilution, although it is understood that LCGreen® Plus is illustrative only and that other dyes are available, as are known in the art. In another optional embodiment, dried fluorescently labeled oligonucleotide probes configured for each specific amplicon may be provided in each respective second-stage blister, along with the respective dried primers. Further, while pouch 10 is designed to contain all reactions and manipulations within, to reduce contamination, in some circumstances it may be desirable to remove the amplification products from each blister 82 to do further analysis. Other means for detection of the second-stage amplicon, as are known in the art, are within the scope of this invention. Once the sample is transferred to blisters 82, pinch valves 84 and 86 are activated to close off blisters 82. Each blister 82 now contains all reagents needed for amplification of a particular target. Illustratively, each blister may contain a unique pair of primers, or a plurality of blisters 82 may contain the same primers to provide a number of replicate amplifications.

It is noted that the embodiments disclosed herein use blisters for the second-stage amplification, wherein the blisters are formed of the same or similar plastic film as the rest of the flexible portion. However, in many embodiments, the contents of the second-stage blisters are never removed from the second-stage blisters, and, therefore, there is no need for the second-stage reaction to take place in flexible blisters. It is understood that the second-stage reaction may take place in a plurality of rigid, semi-rigid, or flexible chambers that are fluidly connected to the blisters. The chambers could be sealed as in the present example by placing pressure on flexible channels that connect the chambers, or may be sealed in other ways, illustratively by heat sealing or use of one-way valves. Various embodiments discussed herein include blisters provided solely for the collection of waste. Since the waste may never be removed, waste could be collected in rigid, semi-rigid, or flexible chambers.

It is within the scope of this invention to do the second-stage amplification with the same primers used in the first-stage amplification (see U.S. Pat. No. 6,605,451). However, it is often advantageous to have primers in second-stage reactions that are internal to the first-stage product such that there is no or minimal overlap between the first- and second-stage primer binding sites. Dilution of first-stage product largely eliminates contribution of the original template DNA and first-stage reagents to the second-stage reaction. Furthermore, illustratively, second-stage primers with a Tm higher than those used in the first-stage may be used to potentiate nested amplification. Primers may be designed to avoid significant hairpins, hetero/homo-dimers and undesired hybridization. Because of the nested format, second-stage primers tolerate deleterious interactions far more so than primers used to amplify targets from genomic DNA in a single step. Optionally, hot-start is used on second-stage amplification.

If a fluorescent dye is included in second-stage amplification, illustratively as a dsDNA binding dye or as part of a fluorescent probe, as are known in the art, optics provided may be used to monitor amplification of one or more of the samples. Optionally, analysis of the shape of the amplification curve may be provided to call each sample positive or negative. Illustrative methods of calling the sample are discussed in U.S. Pat. No. 6,730,501, herein incorporated by reference. Alternatively, methods employing a crossing threshold may be used. A computer may be provided externally or within the instrument and may be configured to perform the methods and call the sample positive or negative based upon the presence or absence of second-stage amplification, and may provide quantitative information about the starting template concentration by comparing characteristic parameters of the amplification curve (such as crossing threshold) to standard curves, or relative to other amplification curves within the run. It is understood, however, that other methods, as are known in the art, may be used to call each sample. Other analyses may be performed on the fluorescent information. One such non-limiting example is the use of melting curve analysis to show proper melting characteristics (e.g. Tm, melt profile shape) of the amplicon. The optics provided may be configured to capture images of all blisters 82 at once, or individual optics may be provided for each individual blister. Other configurations are within the scope of this invention.

Figure 5A:
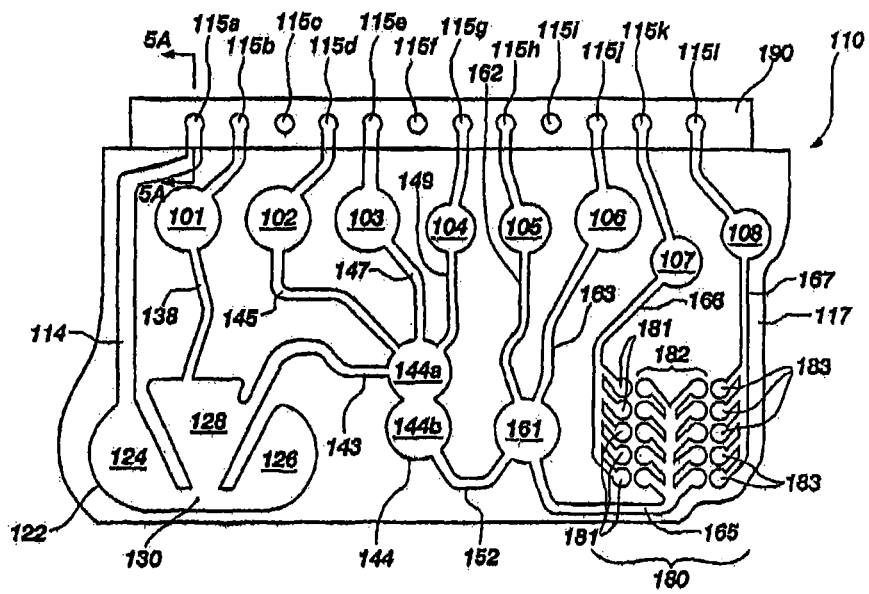
FIG. 5A is similar to FIG. 1, except showing an alternative embodiment of a pouch.
Figure 5B:
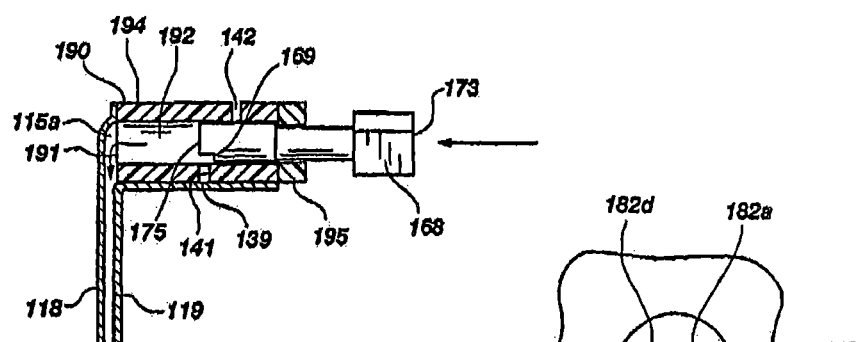
FIG. 5B is a cross-sectional view of the fitment of the pouch of FIG. 5A.

FIG. 5A shows an alternative pouch 110. In this embodiment, various reagents are loaded into pouch 110 via fitment 190. FIG. 5B shows a cross-section of fitment 190 with one of a plurality of plungers 168. It is understood that, while FIG. 5B shows a cross-section through entry channel 115a, as shown in the embodiment of FIG. 5A, there are 12 entry channels present (entry channel 115a through 115l), each of which may have its own plunger 168 for use in fitment 190, although in this particular configuration, entry channels 115c, 115f, and 115i are not used. It is understood that a configuration having 12 entry channels is illustrative only, and that any number of entry channels and associated plungers may be used. In the illustrative embodiment, an optional vacuum port 142 of fitment 190 is formed through a first surface 194 of fitment 190 to communicate with chamber 192. Optional vacuum port 142 may be provided for communication with a vacuum or vacuum chamber (not shown) to draw out the air from within pouch 110 to create a vacuum within chamber 192 and the various blisters and chambers of pouch 110. Plunger 168 is then inserted far enough into chamber 192 to seal off vacuum port 142. Chamber 192 is illustratively provided under a predetermined amount of vacuum to draw a desired volume of liquid into chamber 192 upon use. Additional information on preparing chamber 192 may be found in U.S. patent application Ser. No. 10/512,255, already incorporated by reference.

Illustrative fitment 19Q further includes an injection port 141 formed in the second surface 195 of fitment 190. Illustratively, injection port 141 is positioned closer to the plastic film portion of pouch 110 than vacuum port 142, as shown in FIG. 5B, such that the plunger 168 is inserted far enough to seal off vacuum port 142, while still allowing access to chamber 192 via injection port 141. As shown, second surface 119 of plastic film portion 117 provides a penetrable seal 139 to prevent communication between chamber 192 and the surrounding atmosphere via injection port 141. However, it is understood that second surface 119 optionally may not extend to injection port 141 and various other seals may be employed. Further, if another location for the seal is desired, for example on a first surface 194 of fitment 190, injection port 141 may include a channel to that location on fitment 190. U.S. patent application Ser. No. 10/512,255, already incorporated by reference, shows various configurations where the seal is located remotely from the injection port, and the seal is connected to the chamber via a channel. Also, U.S. patent application Ser. No. 10/512,255 discloses various configurations where channels connect a single seal to multiple chambers. Variations in seal location, as well as connection of a single injection port to multiple chambers, are within the scope of this invention. Optionally, seal 139 may be frangible and may be broken upon insertion of a cannula (not shown), to allow a fluid sample from within the cannula to be drawn into or forced into chamber 192.

The illustrative plunger 168 of the pouch assembly 110 is cylindrical in shape and has a diameter of approximately 5 mm to be press-fit into chamber 192. Plunger 168 includes a first end portion 173 and an opposite second end portion 175. As shown in FIG. 5B, a notch 169 of plunger 168 is formed in second end portion 175. In use, second end portion 175 is inserted part way into chamber 192, and notch 169 may be aligned with injection port 141 to allow a fluid sample to be drawn into or injected into chamber 192, even when plunger 168 is inserted far enough that plunger 168 would otherwise be blocking injection port 141.

Illustratively, a fluid is placed in a container (not shown) with a syringe having a cannulated tip that can be inserted into injection port 141 to puncture seal 139 therein. In using an air-evacuated pouch assembly 110, when seal 139 is punctured, the fluid is withdrawn from the container due to the negative pressure within chamber 192 relative to ambient air pressure. Fluid then passes through port 141 to fill chamber 192. At this point, the fluid usually does not flow into the plastic film portion 117 of pouch 110. Finally, the plunger 168 is inserted into chamber 192 such that second end portion 175 of plunger 168 approaches the bottom 191 of chamber 192, to push a measured amount of the reagent or sample into the plastic film portion 117. As shown, plunger 168 is configured such that upon full insertion, second end portion 175 does not quite meet bottom 191 of chamber 192. The remaining space is useful in trapping bubbles, thereby reducing the number of bubbles entering plastic film portion 117. However, in some embodiments it may be desirable for second end portion 175 to meet bottom 191 upon full insertion of plunger 168. In the embodiment shown in FIG. 5A, entry channels 115a, 115b, 115d, 115e, 115g, 115h, 115j, 115k, and 115l all lead to reaction zones or reservoir blisters. It is understood that full insertion of the plunger associated with entry channel 115a would force a sample into three-lobed blister 122, full insertion of the plunger associated with entry channel 115b would force a reagent into reservoir blister 101, full insertion of the plunger associated with entry channel 115d would force a reagent into reservoir blister 102, full insertion of the plunger associated with entry channel 115e would force a reagent into reservoir blister 103, full insertion of the plunger associated with entry channel 115g would force a reagent into reservoir blister 104, full insertion of the plunger associated with entry channel 115h would force a reagent into reservoir blister 105, full insertion of the plunger associated with entry channel 115j would force a reagent into reservoir blister 106, full insertion of the plunger associated with entry channel 115k would force a reagent into reservoir blister 107, and full insertion of the plunger associated with entry channel 115l would force a reagent into reservoir blister 108.

If a plunger design is used including notch 169 as illustrated in the embodiment shown in FIG. 5B, the plunger 168 may be rotated prior to being lowered, so as to offset notch 169 and to close off injection port 141 from communication with chamber 192, to seal the contents therein. This acts to minimize any potential backflow of fluid through injection port 141 to the surrounding atmosphere, which is particularly useful when it is desired to delay in full insertion of the plunger. Although notch 169 is shown and described above with respect to plunger 168, it is within the scope of this disclosure to close off injection port 141 soon after dispensing the fluid sample into the chamber 192 by other means, such as depressing plunger 168 toward the bottom of chamber 192, heat sealing, unidirectional valves, or self-sealing ports, for example. If heat sealing is used as the sealing method, a seal bar could be included in the instrument such that all chambers are heat sealed upon insertion of the pouch into the instrument.

Figure 6A:
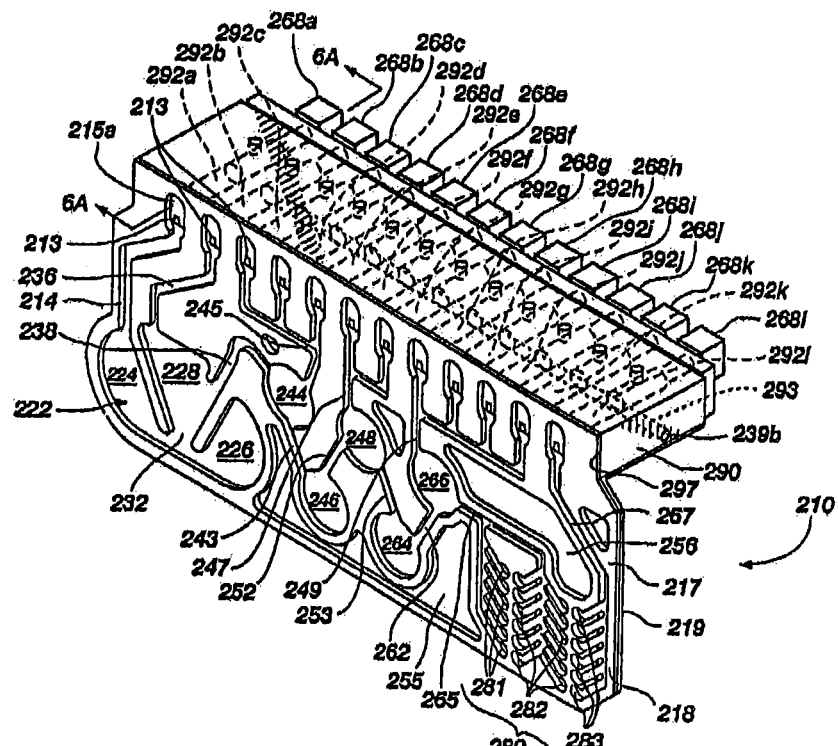
FIG. 6A is a perspective view of another alternative embodiment of a pouch.
Figure 6B:
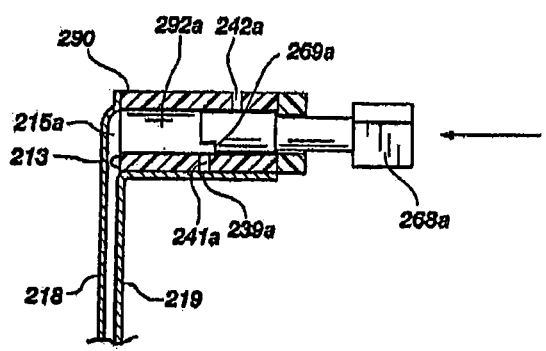
FIG. 6B is a cross-sectional view of the fitment of the pouch of FIG. 6A.

In the illustrative method, the user injects the sample into the injection port 141 associated with entry channel 115*a*, and water into the various other injection ports. The water rehydrates reagents that have been previously freeze-dried into chambers 192 associated with each of entry channels 115*b*, 115*d*, 115*e*, 115*g*, 115*h*, 115*j*, 115*k*, and 115*l*. The water may be injected through one single seal and then be distributed via a channel to each of the chambers, as shown in FIG. 6A below, or the water could be injected into each chamber independently. Alternatively, rather than injecting water to rehydrate dried reagents, wet reagents such as lysis reagents, nucleic acid extraction reagents, and PCR reagents may be injected into the appropriate chambers 192 of the fitment 190.

Figure 8:
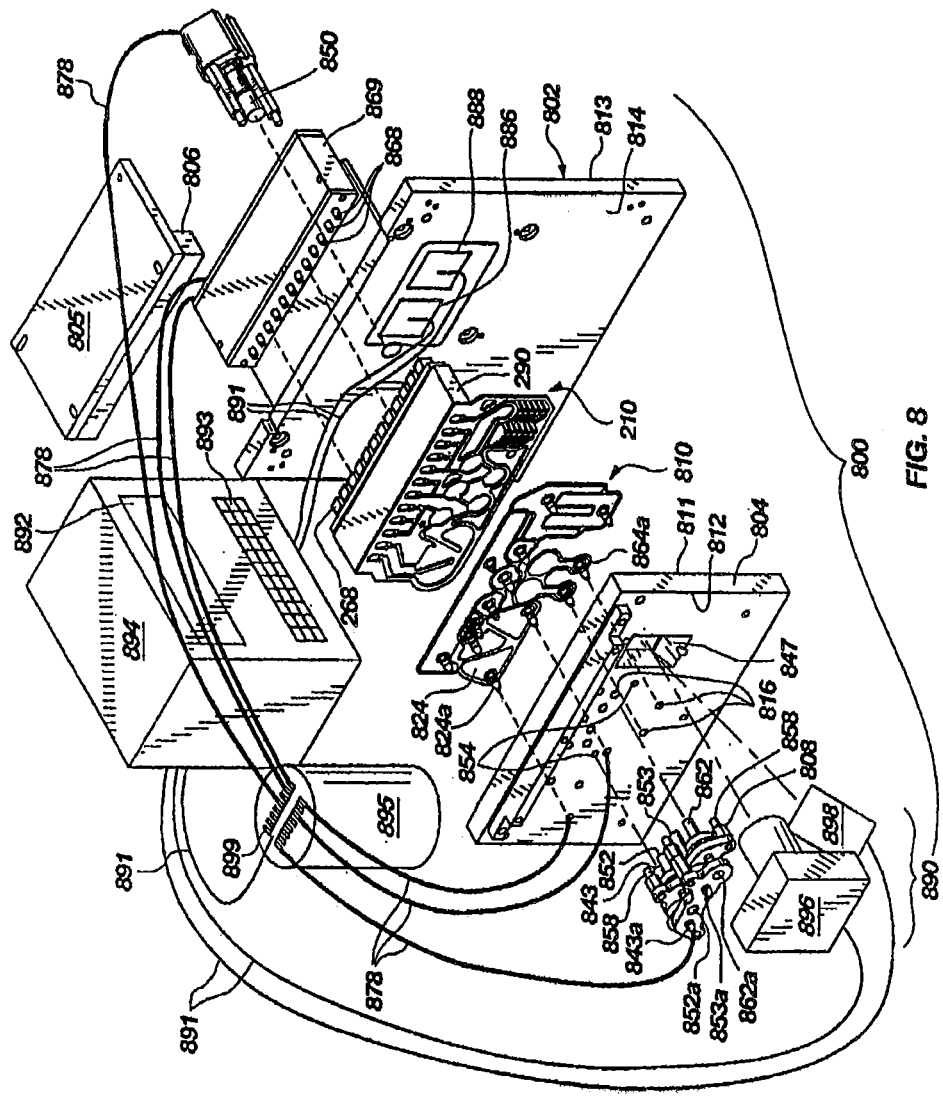
FIG. 8 is an exploded perspective view of an instrument for use with the pouch of FIG. 6A, including the pouch of FIG. 6A.

Upon activation of the plunger 168 associated with entry channel 115*a*, the sample is forced directly into three-lobed blister 122 via channel 114. The user also presses the remaining plungers 168, forcing the contents out of each of the chambers 192 in fitment 190 and into reservoir blisters 101 through 108. At this point, pouch 110 is loaded into an instrument for processing. While instrument 800, shown in FIG. 8, is configured for the pouch 210 of FIG. 6A, it is understood that modification of the configuration of the bladders of instrument 800 would render instrument 800 suitable for use with pouches 110 and 510, or with pouches of other configurations.

In one illustrative example, upon depression of the plungers 168, reservoir blister 101 now contains DNA-binding magnetic beads in isopropanol, reservoir blister 102 now contains a first wash solution, reservoir blister 103 now contains a second wash solution, reservoir blister 104 now contains a nucleic acid elution buffer, reservoir blister 105 now contains first-stage PCR reagents, including multiplexed first-stage primers, reservoir blister 106 now contains second-stage PCR reagents without primers, reservoir blister 107 now contains negative control PCR reagents without primers and without template, and reservoir blister 108 now contains positive control PCR reagents with template. However, it is understood that these reagents are illustrative only, and that other reagents may be used, depending upon the desired reactions and optimization conditions.

Once pouch 110 has been placed into instrument 800 and the sample has been moved to three-lobed blister 122, the sample may be subjected to disruption by agitating the sample with lysing particles such as ZS or ceramic beads. The lysing particles may be provided in three-lobed blister 122, or may be injected into three-lobed blister 122 along with the sample. The three-lobed blister 122 of FIG. 5A is operated in much the same way as three-lobed blister 22 of FIG. 1, with the two lower lobes 124, 126 pressurized together, and pressure is alternated between the upper lobe 128 and the two lower lobes 124, 126. However, as illustrated, lower lobes 124, 126 are much more rounded than lower lobes 24, 26, allowing for a smooth flow of beads to channel 130 and allowing for high-speed collisions, even without the triangular flow separator at nexus 32. As with three-lobed blister 22, three-lobed blister 122 of FIG. 5A allows for effective lysis or disruption of microorganisms, cells, and viral particles in the sample. It has been found that a channel 130 having a width of about 3-4 mm, and illustratively about 3.5 mm, remains relatively clear of beads during lysis and is effective in providing for high-velocity collisions.

After lysis, nucleic-acid-binding magnetic beads are injected into upper lobe 128 via channel 138 by pressurizing a bladder positioned over reservoir blister 101. The magnetic beads are mixed, illustratively more gently than with during lysis, with the contents of three-lobed blister 122, and the solution is incubated, illustratively for about 1 minute, to allow nucleic acids to bind to the beads.

The solution is then pumped into the "FIG. 8" blister 144 via channel 143, where the beads are captured by a retractable magnet housed in the instrument, which is illustratively pneumatically driven. The bead capture process begins by pressurizing all lobes 124, 126, and 128 of the bead milling apparatus 122. This forces much of the liquid contents of 122 through channel 143 and into blister 144. A magnet is brought into contact with the lower portion 144*b* of blister 144 and the sample is incubated for several seconds to allow the magnet to capture the beads from the solution, then the bladders adjacent to blister 122 are depressurized, the bladders adjacent blister portions 144*a* and 144*b* are pressurized, and the liquid is forced back into blister 122. Since not all of the beads are captured in a single pass, this process may be repeated up to 10 times to capture substantially all of the beads in blister 144. Then the liquid is forced out of blister 144, leaving behind only the magnetic beads and the captured nucleic acids, and wash reagents are introduced into blister 144 in two successive washes (from reservoir blisters 102 and 103 via channels 145 and 147, respectively). In each wash, the bladder positioned over the reservoir blister containing the wash reagent is pressurized, forcing the contents into blister 144. The magnet is withdrawn and the pellet containing the magnetic beads is disrupted by alternatively pressurizing each of two bladders covering each lobe 144*a* and 144*b* of blister 144. When the upper lobe 144*a* is compressed, the liquid contents are forced into the lower lobe 144*b*, and when the lower lobe 144*b* is compressed, the contents are forced into the upper lobe 144*a*. By agitating the solution in blister 144 between upper lobe 144*a* and lower lobe 144*b*, the magnetic beads are effectively washed of impurities. A balance is maintained between inadequate agitation, leaving the pellet of beads undisturbed, and excessive agitation, potentially washing the nucleic acids from the surface of the beads and losing them with the wash reagents. After each wash cycle, the magnetic beads are captured via the magnet in blister 144 and the wash reagents are illustratively forced into three-lobed blister 122, which now serves as a waste receptacle. However, it is understood that the used reservoir blisters may also serve as waste receptacles, or other blisters may be provided specifically as waste receptacles.

Nucleic acid elution buffer from reservoir blister 104 is then injected via channel 149 into blister 144, the sample is once again agitated, and the magnetic beads are recaptured by employment of the magnet. The fluid mixture in blister 144 now contains nucleic acids from the original sample. Pressure on blister 144 moves the nucleic acid sample to the first stage PCR blister 161 via channel 152, where the sample is mixed with first-stage PCR master mix containing multiple primer sets, the PCR master mix provided from reservoir blister 105 via channel 162. If desired, the sample and/or the first-stage PCR master mix may be heated prior to mixing, to provide advantages of hot start. Optionally, components for reverse transcription of RNA targets may be provided prior to first-stage PCR. Alternatively, an RT enzyme, illustratively a thermostable RT enzyme may be provided in the first-stage PCR master mix to allow for contemporaneous reverse transcription of RNA targets. It is understood that an RT enzyme may be present in the first-stage PCR mixture in any of the embodiments disclosed herein. As will be seen below, pouch 110 of FIG. 5A is configured for up to 10 primer sets, but it is understood that the configuration may be altered and any number of primer sets may be used. A bladder positioned over blister 161 is pressurized at low pressure, to force the contents of blister 161 into intimate contact with a heating/cooling element, illustratively a Peltier element, on the other side of blister 161. The pressure on blister 161 should be sufficient to assure good contact with the heating/cooling element, but should be gentle enough such that fluid is not forced from blister 161. The heating/cooling element is temperature cycled, illustratively between about 60° C. to about 95° C. Illustratively, temperature cycling is performed for about 15-20 cycles, resulting in amplification of one or more nucleic acid targets present. Also illustratively, temperature cycling ceases prior to plateau phase, and may cease in log phase or even prior to log phase. In one example, it may be desirable merely to enrich the sample with the desired amplicons, without reaching minimal levels of detection. See U.S. Pat. No. 6,605,451, herein incorporated by reference.

The amplified sample is optionally then diluted by forcing most the sample back into blister 144 via channel 152, leaving only a small amount (illustratively about 1 to 5%) of the amplified sample in blister 161, and second-stage PCR master mix is provided from reservoir blister 106 via channel 163. The sample is thoroughly mixed illustratively by moving it back and forth between blisters 106 and 161 via channel 163. If desired, the reaction mixture may be heated to above extension temperature, illustratively at least 60° C., prior to second-stage amplification. The sample is then forced through channel 165 into an array of low volume blisters 182 in the center of second-stage amplification zone 180. Each of the ten illustrative low volume blisters 182 may contain a different primer pair, either essentially the same as one of the primer pairs in the first-stage amplification, or "nested" within the first-stage primer pair to amplify a shortened amplicon. The primers, now hydrated by the sample, complete the amplification mixture. Positive and negative control samples are also introduced by pressurizing the contents of reservoir blisters 107 and 108, respectively, forcing PCR master mix either without target DNA from reservoir blister 107 via channel 166, or with control DNA from reservoir blister 108, via channel 167. As illustrated, there are five each of positive control blisters 183 and negative control blisters 181, which may be multiplexed 2-fold to provide the necessary controls for ten different second-stage amplification reactions. It is understood that this configuration is illustrative only and that any number of second-stage blisters may be provided.

Figure 5C:
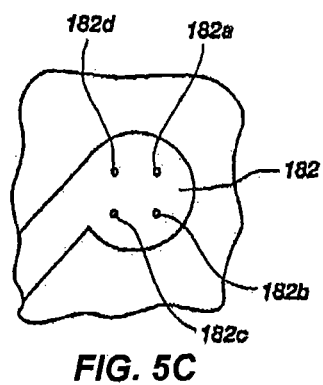
FIG. 5C is an enlargement of a portion of the pouch of FIG. 5A.

Illustratively, the PCR master mix used for second-stage amplification lacks the primers, but is otherwise complete. However, an "incomplete" PCR master mix may lack other PCR components as well. In one example, the second-stage PCR master mix is water or buffer only, which is then mixed with the optionally diluted first-stage PCR amplification product. This mixture is moved to the small-volume PCR reaction blisters, where all of the remaining components have been previously provided. If desired, all of the remaining components may be mixed together and spotted as a single mixture into the small-volume PCR reaction blisters. Alternatively, as illustrated in FIG. 5C, each of the components may be spotted onto a separate region of the small-volume PCR reaction blister 182. As shown in FIG. 5C, four regions are present, illustratively with dNTPs spotted at region 182a, primers spotted at 182b, polymerase spotted at 182c, and a magnesium compound spotted at 182d. By spotting the components separately and heating the sample mixture prior to rehydrating the components, nonspecific reactions can be minimized. It is understood that any combination of components can be spotted this way, and that this method of spotting components into one or more regions of the blisters may be used with any embodiment of the present invention.

The channels 165, 166, and 167 leading to the small-volume PCR reaction blisters 181, 182, and 183 are sealed, and a pneumatic bladder gently presses the array against a heating/cooling element, illustratively a Peltier element, for thermal cycling. The cycling parameters may be independently set for second-stage thermal cycling. Illustratively, the reactions are monitored by focusing an excitation source, illustratively a blue light (450-490 nm), onto the array, and imaging the resultant fluorescent emissions, illustratively fluorescent emissions above 510 nm.

In the above example, pinch valves are not discussed. However, it is understood that when it is desired to contain a sample in one of the blisters, pneumatic actuators positioned over channels leading to and from the particular blister are pressurized, creating pinch valves and closing off the channels. Conversely, when it is desired to move a sample from one of the blisters, the appropriate pneumatic actuator is depressurized, allowing the sample flow through the channel.

The pouch described above in FIG. 5A includes reagent reservoir blisters 101 through 108, in which the user injected reagents from the fitment 190 into the reagent reservoir blisters 101 through 108 in the plastic film portion 117 of the pouch 110, illustratively prior to insertion of pouch 110 into the instrument. While there are advantages to the use of the reagent reservoir blisters of FIG. 5A, including having the ability to maintain the contents of the various blisters at different temperatures, there are some disadvantages as well. Because the operator is responsible for moving the reagents from the fitment 190 to the reservoir blisters 101 through 108, and because this is often done outside of the machine and thus without activated pinch valves, reagents could occasionally leak from the reservoir blisters to the working blisters. The reagents in reservoir blisters are exposed during preparation and loading. If they are pressed, squeezed, or even lightly bumped, the reagents may leak through available channels. If the loss of reagents is substantial, the reaction may fail completely. Furthermore, during operation there may be some variability in the amount of reagent forced from the reservoir blisters 101 through 108, leading to inconsistent results. Automation of introduction of the reagents to fitment 190 and movement of the reagents from fitment 190 to reagent reservoir blisters 101 through 108 would solve many of these problems, and is within the scope of this invention.

The pouch 210 of FIG. 6A addresses many of these issues in a different way, by using a direct-injection approach wherein the instrument itself moves the plungers 268, illustratively via pneumatic pistons, and forces the reagents into the various working blisters as the reagents are needed. Rather than storing the reagents in reservoir blisters 101 through 108 of FIG. 5A, in the embodiment of FIG. 6A the reagents are introduced into various chambers 292 of fitment 290 and are maintained there until needed. Pneumatic operation of piston 268 at the appropriate time introduces a measured amount of the reagent to the appropriate reaction blister. In addition to addressing many of the above-mentioned issues, pouch 210 also has a much more compact shape, allowing for a smaller instrument design, and pouch 210 has shorter channels, permitting better fluid flow and minimizing reagent loss in channels.

In one illustrative embodiment of FIG. 6A, a 300 µl mixture comprising the sample to be tested (100 µl) and lysis buffer (200 µl) is injected into injection port 241a. Water is also injected into the fitment 290 via seal 239b, hydrating up to eleven different reagents, each of which were previously provided in dry form in chambers 292b through 292l via channel 293 (shown in shadow). These reagents illustratively may include freeze-dried PCR reagents, DNA extraction reagents, wash solutions, immunoassay reagents, or other chemical entities. For the example of FIG. 6A, the reagents are for nucleic acid extraction, first-stage multiplex PCR, dilution of the multiplex reaction, and preparation of second-stage PCR reagents, and control reactions. In the embodiment shown in FIG. 6A, all that need be injected is the sample in port 241a and water in port 241b.

As shown in FIG. 6A, water injected via seal 293b is distributed to various chambers via channel 293. In this embodiment, only the sample and water need be injected into pouch 210. It is understood, however, that water could be injected into each chamber 292 independently. Further, it is understood that, rather than providing dried reagents in the various chambers 292 and hydrating upon injection of the water, specific wet reagents could be injected into each chamber, as desired. Additionally, it is understood that one or more of chambers 292 could be provided with water only, and the necessary reagents may be provided dried in the appropriate reaction blisters. Various combinations of the above, as dictated by the needs of the particular reaction, are within the scope of this invention.

As seen in FIG. 6A, optional protrusions 213 are provided on bottom surface 297 of fitment 290. As shown, protrusions 213 are located within their respective entry channels 215. However, other configurations are possible. Protrusions 213 assist in opening entry channel 215 and prevent bottom surface 297 from engaging another flat surface in such a way to pinch off entry channels 215 when plungers 268 are depressed, which helps prevent back-flow upon activation of the plungers 268. Such protrusions may be used on any of the various pouches according to the present invention.

In embodiments wherein water is injected into the pouch to hydrate multiple dry reagents in multiple chambers in the fitment, a means of closing the channel between the injection port and the many chambers is desired. If the channel is not closed, activation of each plunger may force some of the contents of its respective chamber back out into the channel, potentially contaminating neighboring chambers and altering the volumes contained in and delivered from the chamber. Several ways of closing this channel have been used, including rotating a notched plunger 268 as discussed above, and heat-sealing the plastic film across the channel thereby closing the channel permanently, and applying pressure to the channel as a pinch valve. Other closures may also be used, such as valves built into the fitment, illustratively one-way valves.

Figure 7:
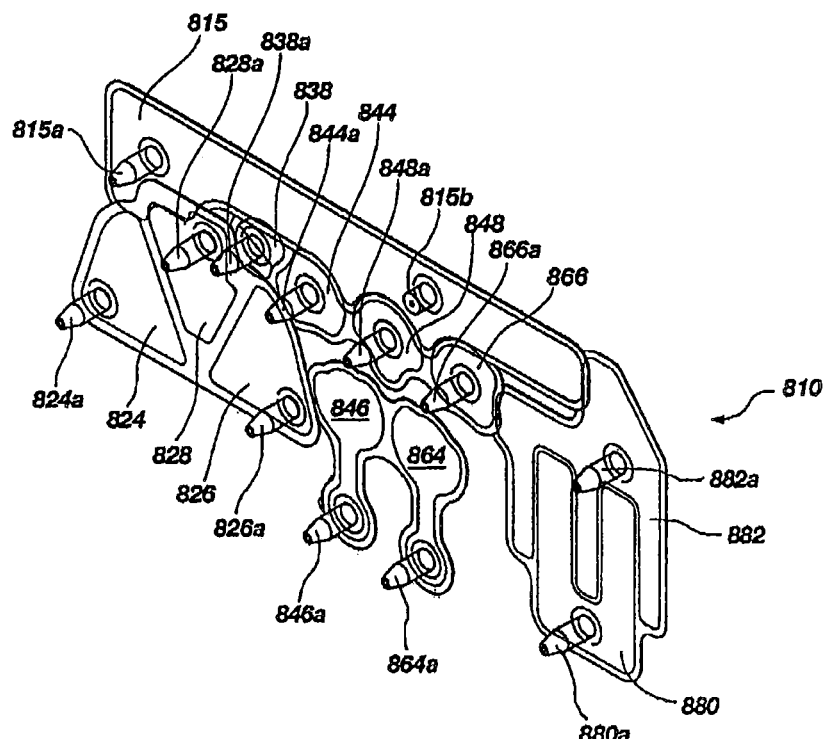
FIG. 7 shows illustrative bladder components for use with the pouch of FIG. 6A.

After the fluids are loaded into chambers 292 and pouch 210 is loaded into the instrument, plunger 268a is depressed illustratively via activation of a pneumatic piston, forcing the balance of the sample into three-lobed blister 220 via channel 214. As with the embodiments shown in FIGS. 1 and 5, the lobes 224, 226, and 228 of three-lobed blister 220 are sequentially compressed via action bladders 824, 826, and 828 of bladder assembly 810, shown in FIGS. 7-9, forcing the liquid through the narrow nexus 232 between the lobes, and driving high velocity collisions, shearing the sample and liberating nucleic acids, illustratively including nucleic acids from hard-to-open spores, bacteria, and fungi. Cell lysis continues for an appropriate length of time, illustratively 0.5 to 10 minutes.

Once the cells have been adequately lysed, plunger 268b is activated and nucleic acid binding magnetic beads stored in chamber 292b are injected via channel 236 into upper lobe 228 of three-lobed blister 220. The sample is mixed with the magnetic beads and the mixture is allowed to incubate for an appropriate length of time, illustratively approximately 10 seconds to 10 minutes.

The mixture of sample and beads are forced through channel 238 into blister 244 via action of bladder 826, then through channel 243 and into blister 246 via action of bladder 844, where a retractable magnet 850 located in instrument 800 adjacent blister 245, shown in FIG. 8, captures the magnetic beads from the solution, forming a pellet against the interior surface of blister 246. A pneumatic bladder 846, positioned over blister 246 then forces the liquid out of blister 246 and back through blister 244 and into blister 222, which is now used as a waste receptacle. However, as discussed above with respect to FIG. 5A, other waste receptacles are within the scope of this invention. One of plungers 268c, 268d, and 268e may be activated to provide a wash solution to blister 244 via channel 245, and then to blister 246 via channel 243. Optionally, the magnet 850 is retracted and the magnetic beads are washed by moving the beads back and forth from blisters 244 and 246 via channel 243, by alternatively pressurizing bladders 844 and 846. Once the magnetic beads are washed, the magnetic beads are recaptured in blister 246 by activation of magnet 850, and the wash solution is then moved to blister 222. This process may be repeated as necessary to wash the lysis buffer and sample debris from the nucleic acid-binding magnetic beads. Illustratively, three washes are done, one each using wash reagents in chambers 292c, 292d, and 292e. However, it is understood that more or fewer washes are within the scope of this invention. If more washes are desired, more chambers 292 may be provided. Alternatively, each chamber 292 may hold a larger volume of fluid and activation of the plungers may force only a fraction of the volume from the chamber upon each activation.

After washing, elution buffer stored in chamber 292f is moved via channel 247 to blister 248, and the magnet is retracted. The solution is cycled between blisters 246 and 248 via channel 252, breaking up the pellet of magnetic beads in blister 246 and allowing the captured nucleic acids to dissociate from the beads and come into solution. The magnet 850 is once again activated, capturing the magnetic beads in blister 246, and the eluted nucleic acid solution is forced into blister 248.

Plunger 268h is depressed and first-stage PCR master mix from chamber 292h is mixed with the nucleic acid sample in blister 248. Optionally, the mixture is mixed by alternative activation of bladders 848 and 864, forcing the mixture between 248 and 264 via channel 253. After several cycles of mixing, the solution is contained in blister 264, where first-stage multiplex PCR is performed. If desired, prior to mixing, the sample may be retained in blister 246 while the first-stage PCR master mix is pre-heated, illustratively by moving the first-stage PCR master mix into blister 264 or by providing a heater adjacent blister 248. As discussed above, this pre-heating may provide the benefits of hot start PCR.

The instrument 800 illustrated in FIG. 8 features Peltier-based thermal cyclers 886 and 888 which heat and cool the sample. However, it is understood that other heater/cooler devices may be used, as discussed above. Optionally, mixing between blisters 248 and 264 may continue during temperature cycling, with thermal cycler 886 positioned to heat and cool both blisters 248 and 264. It has been found that such mixing improves the first-stage PCR reaction in some embodiments. Also, thermal cycling can be accomplished by varying the temperatures in two or more different blisters, allowing minimal energy expenditure and maximizing thermal cycling speed. For example the temperature can be maintained at 95° C. in blister 248, and 65° C. blister 264, and moving the sample between these blisters effectively transfers heat into and out of the sample, allowing rapid and accurate thermal cycling. Temperature cycling is illustratively performed for 15-20 cycles, although other levels of amplification may be desirable, depending on the application, as discussed above. As will be seen below, the second-stage amplification zone 280 is configured to detect amplification in 18 second-stage reactions. Accordingly, 18 different primer-pairs may be included in the PCR reaction in blister 264.

In an alternative hot start method, pouch 210 is manufactured with the primers provided in one of the blisters, illustratively blister 264. In one embodiment, the primers are freeze dried separately and then introduced during manufacture into blister 264 as a friable pellet. Prior to first-stage PCR, illustratively the sample is eluted from blister 246 and pushed to blister 264 to rehydrate the primer pellet. Peltier 886, which is positioned adjacent blisters 248 and 264 is heated to 48° C., and PCR master mix is pushed to blister 248. After a hold, illustratively for 10 seconds, during which the two blisters reach 48° C., mixing between blisters 248 and 264 begins. Thus, the enzymes and dNTPs remain in blister 248 and most of the sample and the primers remain in blister 264 until the components separately have reached 48° C. It is understood, however, that the choice of 48° C. was made for use with concurrent first-stage amplification and RT using AMV, which is active up to 50° C. If RT is not needed or a more thermostable RT enzyme is used, then one or both of the two blisters 248 and 264 may be heated up to 58° C., or even higher, depending on the primer melting temperature or other factors in a particular first-stage amplification protocol. It is understood that this hot start method may be used with any embodiment of the present invention.

In an alternative embodiment, to reduce the complexity of the first-stage PCR reaction, blister 248 may be divided into two or more blisters. It is believed that the number of nonspecific products of a multiplex reaction goes up as the square (or possibly higher power) of the number of primers in the mixture, while the loss of sensitivity of an assay is a linear function of the amount of input sample. Thus, for example, splitting the first stage PCR into two reactions, each of half the volume of the single reaction of this embodiment, would reduce sensitivity by two-fold but the quantity and complexity of the nonspecific reactions would be ¼ as much. If blister 248 is divided into or more blisters, blister 264 may be divided into a number of blisters equal to the number of blisters 248. Each respective blister 248 would be connected to its respective blister 264 via a respective channel 253. Each blister 264 would be provided with a pellet comprising a subset of all primers. Sample from blister 246 would be divided across each blister 248, each blister 248 would be sealed from all others, and thermal cycling would proceed with each pair of blisters 248 and 264, as described above. After thermal cycling, the sample would be recombined into blister 266 or individually sent to separate sets of second-stage blisters.

After first-stage PCR has proceeded for the desired number of cycles, the sample may be diluted as discussed above with respect to the embodiment of FIG. 5A, by forcing most of the sample back into blister 248, leaving only a small amount, and adding second-stage PCR master mix from chamber 292*i*. Alternatively, a dilution buffer from 292*i* may be moved to blister 266 via channel 249 and then mixed with the amplified sample in blister 264 by moving the fluids back and forth between blisters 264 and 266. After mixing, a portion of the diluted sample remaining in blister 264 is forced away to three-lobed blister 222, now the waste receptacle. If desired, dilution may be repeated several times, using dilution buffer from chambers 292*j* and 292*k*, and then adding second-stage PCR master mix from chamber 292*g* to some or all of the diluted amplified sample. It is understood that the level of dilution may be adjusted by altering the number of dilution steps or by altering the percentage of the sample discarded prior to mixing with the dilution buffer or second-stage PCR master mix. If desired, this mixture of the sample and second-stage PCR master mix may be pre-heated in blister 264 prior to movement to second-stage blisters 282 for second-stage amplification. As discussed above, such preheating may obviate the need for a hot-start component (antibody, chemical, or otherwise) in the second-stage PCR mixture.

The illustrative second-stage PCR master mix is incomplete, lacking primer pairs, and each of the 18 second-stage blisters 282 is pre-loaded with a specific PCR primer pair. If desired, second-stage PCR master mix may lack other reaction components, and these components may then be pre-loaded in the second-stage blisters 282 as well. As discussed above with the prior examples, each primer pair may be identical to a first-stage PCR primer pair or may be nested within the first-stage primer pair. Movement of the sample from blister 264 to the second-stage blisters completes the PCR reaction mixture. Control samples from chamber 292*l* are also moved to control blisters 283 via channel 267. The control samples may be positive or negative controls, as desired. Illustratively, each pouch would contain control reactions that validate the operation of each step in the process and demonstrate that positive results are not the result of self-contamination with previously amplified nucleic acids. However, this is not practical in many protocols, particularly for a highly multiplexed reaction. One illustrative way of providing suitable controls involves spiking samples with a species such as baker's yeast. The nucleic acids are extracted from the yeast, alongside other nucleic acids. First- and second-stage PCR reactions amplify DNA and/or RNA targets from the yeast genome. Illustratively, an mRNA sequence derived from a spliced pre-mRNA can be used to generate an RNA-specific target sequence by arranging the primer sequences to span an intron. A quantitative analysis of the yeast copy number against reference standards allows substantial validation that each component of the system is working. Negative control reactions for each of the many second-stage assays are more problematic. It may be desirable to run control reactions either in parallel or in a separate run.

Activation of bladder 882 of bladder assembly 810 seals the samples into their respective second-stage blisters 282, 283, and activation of bladder 880 provides gentle pressure on second-stage blisters 282, 283, to force second-stage blisters 282, 283 into contact with a heater/cooler device. A window 847 positioned over the second-stage amplification zone 280 allows fluorescence monitoring of the array during PCR and during a DNA melting-curve analysis of the reaction products.

It is noted that the pouch 210 of FIG. 6A has several unsealed areas, such as unsealed area 255 and unsealed area 256. These unsealed areas form blisters that are not involved in any of the reactions in this illustrative embodiment. Rather, these unsealed areas are provided in space between the working blisters and channels. In some manufacturing processes, as compared to pouches that are sealed in all unused space, it has been found that fewer leaks sometimes result when unsealed areas such as 255 and 256 are provided, presumably by reducing problematic wrinkles in the film material. Such unsealed areas optionally may be provided on any pouch embodiment.

FIG. 8 shows an illustrative apparatus 800 that could be used with pouch 210. Instrument 800 includes a support member 802 that could form a wall of a casing or be mounted within a casing. Instrument 800 also includes a second support member 804 that is optionally movable with respect to support member 802, to allow insertion and withdrawal of pouch 210. Movable support member 804 may be mounted on a track or may be moved relative to support member 802 in any of a variety of ways. Illustratively, a lid 805 fits over pouch 210 once pouch 210 has been inserted into instrument 800. In another embodiment, both support members 802 and 804 may be fixed, with pouch 210 held into place by other mechanical means or by pneumatic pressure.

Illustratively, the bladder assembly 810 and pneumatic valve assembly 808 are mounted on movable member 802, while the heaters 886 and 888 are mounted on support member 802. However, it is understood that this arrangement is illustrative only and that other arrangements are possible. As bladder assembly 810 and pneumatic valve assembly 3Q 808 are mounted on movable support member 804, these pneumatic actuators may be moved toward pouch 210, such that the pneumatic actuators are placed in contact with pouch 210. When pouch 210 is inserted into instrument 800 and movable support member 804 is moved toward support member 802, the various blisters of pouch 210 are in a position adjacent to the various pneumatic bladders of bladder assembly 810 and the various pneumatic pistons of pneumatic valve assembly 808, such that activation of the pneumatic actuators may force liquid from one or more of the blisters of pouch 210 or may form pinch valves with one or more channels of pouch 210. The relationship between the blisters and channels of pouch 210 and the pneumatic actuators of bladder assembly 810 and pneumatic valve assembly 808 are discussed in more detail below with respect to FIGS. 9 and 10.

Each pneumatic actuator has one or more pneumatic fittings. For example, bladder 824 of bladder assembly 810 has pneumatic fitting 824a and pneumatic piston 843 has its associated pneumatic fitting 843a. In the illustrative embodiment, each of the pneumatic fittings of bladder assembly 810 extends through a passageway 816 in movable support member 804, where a hose 878 connects each pneumatic fitting to compressed air source 895 via valves 899. In the illustrative embodiment, the passageways 816 not only provide access to compressed air source 895, but the passageways also aid in aligning the various components of bladder assembly 810, so that the bladders align properly with the blisters of pouch 210.

Similarly, pneumatic valve assembly 808 is also mounted on movable support member 804, although it is understood that other configurations are possible. In the illustrative embodiment, pins 858 on pneumatic valve assembly 808 mount in mounting openings 859 on movable support member 804, and pneumatic pistons 843, 852, 853, and 862 extend through passageways 816 in movable support member 804, to contact pouch 210. As illustrated, bladder assembly is mounted on a first side 811 of movable support member 804 while pneumatic valve assembly 808 is mounted on a second side 812 of movable support member 804. However, because pneumatic pistons 843, 852, 853, and 862 extend through passageways 816, the pneumatic pistons of pneumatic valve assembly 808 and the pneumatic bladders of bladder assembly 810 work together to provide the necessary pneumatic actuators for pouch 210.

As discussed above, each of the pneumatic actuators of bladder assembly 810 and pneumatic valve assembly 808 has an associated pneumatic fitting. While only several hoses 878 are shown in FIG. 8, it is understood that each pneumatic fitting is connected via a hose 878 to the compressed gas source 895. Compressed gas source 895 may be a compressor, or, alternatively, compressed gas source 895 may be a compressed gas cylinder, such as a carbon dioxide cylinder. Compressed gas cylinders are particularly useful if portability is desired. Other sources of compressed gas are within the scope of this invention.

Several other components of instrument 810 are also connected to compressed gas source 895. Magnet 850, which is mounted on a first side 813 of support member 802, is illustratively deployed and retracted using gas from compressed gas source 895 via hose 878, although other methods of moving magnet 850 are known in the art. Magnet 850 sits in recess 851 in support member 802. It is understood that recess 851 can be a passageway through support member 802, so that magnet 850 can contact blister 246 of pouch 210. However, depending on the material of support member 802, it is understood that recess 851 need not extend all the way through support member 802, as long as when magnet 850 is deployed, magnet 850 is close enough to provide a sufficient magnetic field at blister 246, and when magnet 850 is retracted, magnet 850 does not significantly affect any magnetic beads present in blister 246. While reference is made to retracting magnet 850, it is understood that an electromagnet may be used and the electromagnet may be activated and inactivated by controlling flow of electricity through the electromagnet. Thus, while this specification discusses withdrawing or retracting the magnet, it is understood that these terms are broad enough to incorporate other ways of withdrawing the magnetic field. It is understood that the pneumatic connections may be pneumatic hoses or pneumatic air manifolds, thus reducing the number of hoses or valves required.

The various pneumatic pistons 868 of pneumatic piston array 869, which is mounted on support 802, are also connected to compressed gas source 895 via hoses 878. While only two hoses 878 are shown connecting pneumatic pistons 868 to compressed gas source 895, it is understood that each of the pneumatic pistons 868 are connected to compressed gas source 895. Twelve pneumatic pistons 868 are shown. When the pouch 210 is inserted into instrument 800, the twelve pneumatic pistons 868 are positioned to activate their respective twelve plungers 268 of pouch 210. When lid 805 is closed over pouch 210, a lip 806 on lid 805 provides a support for fitment 29Q, so that as the pneumatic pistons 868 are activated, lid 805 holds fitment 290 in place. It is understood that other supports for fitment 290 are within the scope of this invention.

A pair of heating/cooling devices, illustratively Peltier heaters, are mounted on a second side 814 of support 802.

First-stage heater 886 is positioned to heat and cool the contents of blister 264 for first-stage PCR. Second-stage heater 888 is positioned to heat and cool the contents of second-stage blisters 282 and 283 of pouch 210, for second-stage PCR. It is understood, however, that these heaters could also be used for other heating purposes, and that other heaters may be included, as appropriate for the particular application.

If desired, a feedback mechanism (not shown) may be included in instrument 800 for providing feedback regarding whether the sample has actually been forced into a particular blister. Illustrative feedback mechanisms include temperature or pressure sensors or optical detectors, particularly if a fluorescent or colored dye is included. Such feedback mechanisms illustratively may be mounted on either of support members 802 or 804. For example, a pressure sensor may be mounted on support 802 adjacent the location of blister 264. When the sample is supposedly moved to blister 264, if the pressure sensor is depressed, then sample processing is allowed to continue. However, if the pressure sensor is not depressed, then sample processing may be stopped, or an error message may be displayed on screen 892. Any combination or all of the blisters may have feedback mechanisms to provide feedback regarding proper movement of the sample through the pouch.

When fluorescent detection is desired, an optical array 890 may be provided. As shown in FIG. 8, optical array 890 includes a light source 898, illustratively a filtered LED light source, filtered white light, or laser illumination, and a camera 896. A window 847 through movable support 804 provides optical array 890 with access to second-stage amplification zone 280 of pouch 210. Camera 896 illustratively has a plurality of photodetectors each corresponding to a second-stage blister 282, 823 in pouch 210. Alternatively, camera 896 may take images that contain all of the second-stage blisters 282, 283, and the image may be divided into separate fields corresponding to each of the second-stage blisters 282, 283. Depending on the configuration, optical array 890 may be stationary, or optical array 890 may be placed on movers attached to one or more motors and moved to obtain signals from each individual second-stage blister 282, 283. It is understood that other arrangements are possible.

As shown, a computer 894 controls valves 899 of compressed air source 895, and thus controls all of the pneumatics of instrument 800. Computer 894 also controls heaters 886 and 888, and optical array 890. Each of these components is connected electrically, illustratively via cables 891, although other physical or wireless connections are within the scope of this invention. It is understood that computer 894 may be housed within instrument 890 or may be external to instrument 890. Further, computer 894 may include built-in circuit boards that control some or all of the components, and may also include an external computer, such as a desktop or laptop PC, to receive and display data from the optical array. An interface 893, illustratively a keyboard interface, may be provided including keys for inputting information and variables such as temperatures, cycle times, etc. Illustratively, a display 892 is also provided. Display 892 may be an LED, LCD, or other such display, for example.

Figure 9:
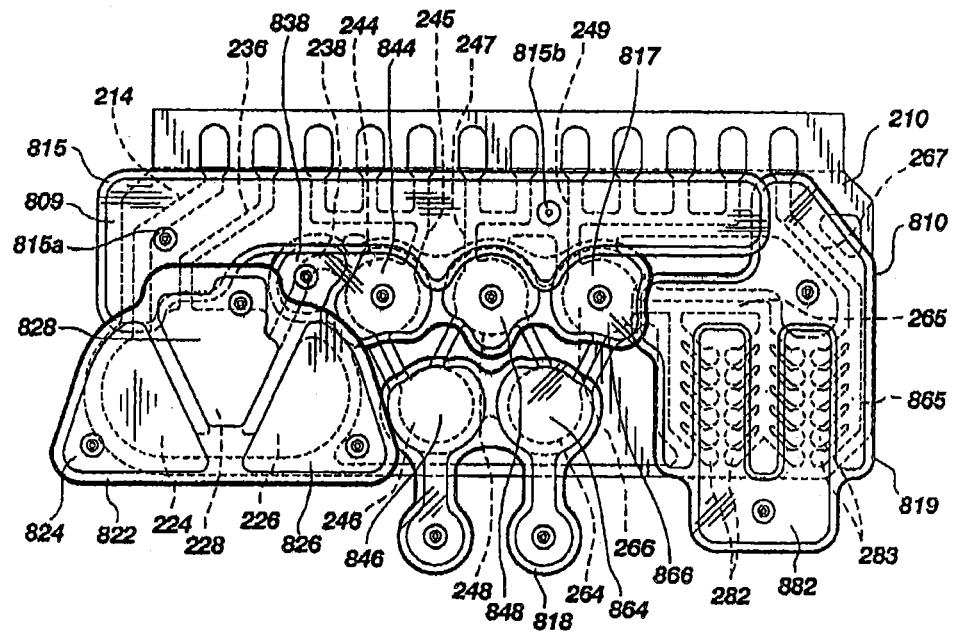
FIG. 9 shows a partial cross-sectional view of the instrument of FIG. 8, including the bladder components of FIG. 7, with the pouch of FIG. 6A shown in shadow.

FIG. 9 shows the relationship between bladder assembly 810 and pouch 210 during operation of instrument 800. Bladder assembly comprises sub-assemblies 815, 817, 818, 819, and 822. Because bladder 809 of bladder sub-assembly 815 is large, bladder sub-assembly 815 illustratively has two pneumatic fittings 815*a* and 815*b*. Bladder 809 is used to close off chambers 292 (as shown in FIG. 6A) from the plastic film portion 217 of pouch 210. When one of the plungers 268 is depressed, one or both of pneumatic fittings 815*a* and 815*b* permit bladder 809 to deflate. After the fluid from one of the chambers 292 passes through, bladder 809 is re-pressurized, sealing off channels 214, 236, 245, 247, and 249. While illustrative bladder sub-assembly 815 has only one bladder 809, it is understood that other configurations are possible, illustratively where each of channels 214, 236, 245, 247, and 249 has its own associated bladder or pneumatic piston. Bladder sub-assembly 822 illustratively comprises three bladders 824, 826, and 828. As discussed above, bladders 824, 824, and 828 drive the three-lobed blister 222 for cell lysis. As illustrated, bladders 824, 826, and 828 are slightly larger than their corresponding blisters 224, 226, 228. It has been found that, upon inflation, the surface of the bladders can become somewhat dome-shaped, and using slightly oversized bladders allows for good contact over the entire surface of the corresponding blister, enabling more uniform pressure and better evacuation of the blister. However, in some circumstances, complete evacuation of individual blisters may or may not be desired, and larger or smaller-sized bladders may be used to control the blister volume evacuated. Bladder sub-assembly 817 has four bladders. Bladder 836 functions as a pinch-valve for channel 236, while bladders 844, 848, and 866 are configured to provide pressure on blisters 244, 248, and 266, respectively. Bladder sub-assembly 818 has two bladders 846 and 864, which are configured to provide pressure on blisters 246 and 264, respectively. Finally, bladder sub-assembly 819 controls second-stage amplification zone 280. Bladder 865 acts as a pinch valve for channels 265 and 267, while bladder 882 provides gentle pressure to second-stage blisters 282 and 283, to force second-stage blisters into close contact with heater 888. While bladder assembly 810 is provided with five sub-assemblies, it is understood that this configuration is illustrative only and that any number of sub-assemblies could be used or that bladder assembly 810 could be provided as a single integral assembly.

Figure 10:
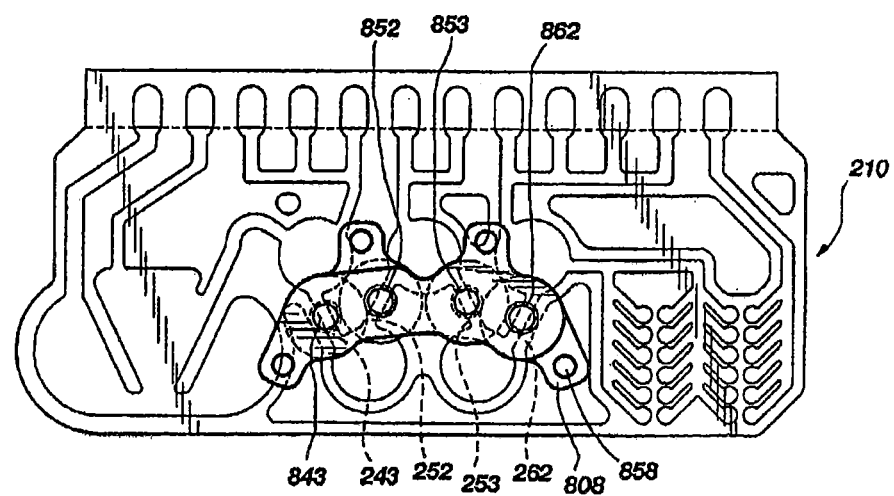
FIG. 10 shows a partial cross-sectional view of the instrument of FIG. 8, including various bladders for pinch valves and the pouch of FIG. 6A.

FIG. 10 similarly shows the relationship between pneumatic valve assembly 808 and pouch 210 during operation of instrument 800. Rather than bladders, pneumatic valve assembly 808 has four pneumatic pistons 842, 852, 853, and 862. These pneumatic pistons 842, 852, 853, and 862, each driven by compressed air, provide directed pressure on channels 242, 252, 253, and 262. Because the pistons are fairly narrow in diameter, they can fit between bladder sub-assembly 817 and bladder sub-assembly 818 to provide pinch valves for channels 242, 252, 253, and 262, allowing channels 242, 252, 253, and 262 to be fairly short. However, if desired, pneumatic pistons 842, 852, 853, and 862 could be replaced by bladders, which may be included in bladder assembly 810, obviating the need for pneumatic valve assembly 808. It is understood that any combination of bladders and pneumatic pistons are within the scope of this invention. It is also understood that other methods of providing pressure on the channels and blisters of pouch 210, as are known in the art, are within the scope of this invention.

FIG. 12A shows a pouch 510 that is similar to pouch 210 of FIG. 6A. Fitment 590, with entry channels 515*a* through 515*l*, is similar to fitment 290, with entry channels 215*a* through 215*l*. Blisters 544, 546, 548, 564, and 566, with their respective channels 538, 543, 552, 553, 562, and 565 are similar to blisters 244, 246, 248, 264, and 266, with their respective channels 238, 243, 252, 253, 262, and 265 of pouch 210. The channels 245, 247, and 249 of pouch 210 have been somewhat reconfigured as channels 545*a*-*c*, 547*a*- b, and 548a-c on pouch 510; the respective channels of 510 are somewhat shorter than their counterpart channels on pouch 210. However, it is understood that channel configurations are illustrative only, and that various channel configurations are within the scope of this invention.

Figure 2C:
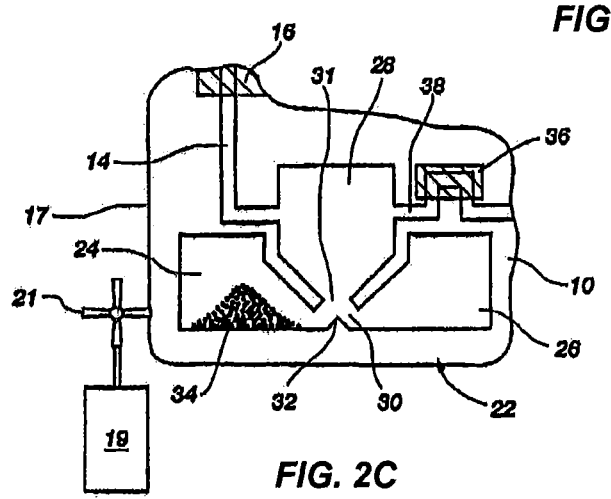
FIG. 2C shows an embodiment of the cell lysis zone of the flexible pouch according to FIG. 1 having an alternative vortexing mechanism.

There are two main differences between pouch 510 of FIG. 12A and pouch 210 of FIG. 6A. First, three-lobed blister 222 has been replaced by lysis blister 522. Lysis blister 522 is configured for vortexing via impaction using rotating blades or paddles 21 attached to electric motor 19, as shown in FIG. 2C. Since this method of lysing does not rely on alternating pressure of pneumatic pistons, only a single-lobed blister is shown. Because lysis blister 522 has only a single lobe, both channels 514 and 536 lead to the single lobe of lysis blister 522. It is understood that lysis blister 522 may be used in any of the pouch embodiments described herein. It is further understood that lysis assembly 810 illustratively may be modified to replace bladders 824, 826, and 828 of bladder sub-assembly 822 with a single bladder configured for blister 522. Conversely, a three-lobed blister, as described in various other embodiments above, may be used in pouch 510. Lysis blister 522 may be provided with an optional reinforcing patch 523, illustratively attached using adhesive or lamination to the exterior surface of lysis blister 522. Reinforcing patch 523 aids in minimizing tearing of pouch 510 due to repeated contact by paddles 21. FIG. 12B shows an electric motor, illustratively a Mabuchi RC-280SA-2865 DC Motor (Chiba, Japan), mounted on second support member 804. In one illustrative embodiment, the motor is turned at 5,000 to 25,000 rpm, more illustratively 10,000 to 20,000 rpm, and still more illustratively approximately 15,000 to 18,000 rpm. For the Mabuchi motor, it has been found that 7.2V provides sufficient rpm for lysis. It is understood, however, that the actual speed may be somewhat slower when the blades 21 are impacting pouch 510. Other voltages and speeds may be used for lysis depending on the motor and paddles used. Optionally, controlled small volumes of air may be provided into the bladder adjacent lysis blister 522. It has been found that in some embodiments, partially filling the adjacent bladder with one or more small volumes of air aids in positioning and supporting lysis blister during the lysis process. Alternatively, other structure, illustratively a rigid or compliant gasket or other retaining structure around lysis blister 522, can be used to restrain pouch 510 during lysis.

The second main difference between pouch 510 of FIG. 12A and pouch 210 of FIG. 6A is that the blisters 281, 282, and 283 of second-stage amplification zone 280 have been replaced by high density array 581 in second-stage amplification zone 580. High density array 581 comprises a plurality of second-stage wells 582, illustratively 50 or more wells, and even more illustratively 120 or more wells. Embodiments with more second-stage wells 582, illustratively about 200, about 400, or even about 500 or more are within the scope of this invention. Other configurations are within the scope of this invention as well. Additional second-stage wells 582 may be added by making wells 582 smaller, by making high density array 581 larger, or a combination thereof. For second-stage PCR, each of the wells may contain a pair of primers. It is understood that one or more wells may be used for positive or negative controls.

Cross-contamination between wells as the wells are filled with the diluted first-stage amplification product in blister 566 can be a major problem. Cross-contamination was controlled in pouch 210 by filling each second-stage blister through a separate branch of channel 265 and then sealing with bladder 882, illustrated in FIG. 9. With high density array 581, wherein fluid may fill some or all of blister 584, cross-contamination between wells must also be controlled. In one embodiment, the second-stage PCR primers may be bound covalently or non-covalently to the inside surface of each well, thus functioning much like a PCR chip. However, in many embodiments it is desirable to control cross-contamination between wells without tethering the PCR primers to the wells. Controlling cross-contamination between wells can be difficult in an embodiment wherein the fluid from blister 566 is moved to wells 582 by flowing across a first surface 581a of high density array 581.

There are several desirable features for successful loading of the second-stage amplification zone 580. First, it is desirable that the incoming fluid from blister 566 fill substantially all of the wells 582 to substantially the same level. An unfilled well would produce a false negative signal. Second, it is desirable that the process of filling the wells 582 should not cause the primers in the well to leak out. Loss of primers from one well can limit the efficiency of the PCR reaction in that well and can contaminate neighboring wells. Third, after the wells 582 have been filled and PCR started, it is desirable that the wells be completely sealed from each other. Amplicon leakage out of one well and into another well can lower signal in the first well and raise signal in the second well, potentially leading to a false negative in the first well and a false positive in the second well. Further, for certain kinds of controls, it is important that amplicon generated in one well not enter another well where it can be further amplified.

Solutions to this problem include use of a barrier layer. In one example, the barrier layer is a physical barrier that is provided to allow for rapid loading of the wells and for rapid sealing from the bulk fluid. In another example, combined chemical and physical barriers are used, wherein the physical barrier is used to seal the wells and then the chemical barrier conditionally releases the oligonucleotide primers into the well solution, for example by heating, slow release, or enzymatic digestion. Well depth or channel length to each well also may be used to control release of the reagents from the wells. Other means for loading high density array 581 are possible.

Figure 13:
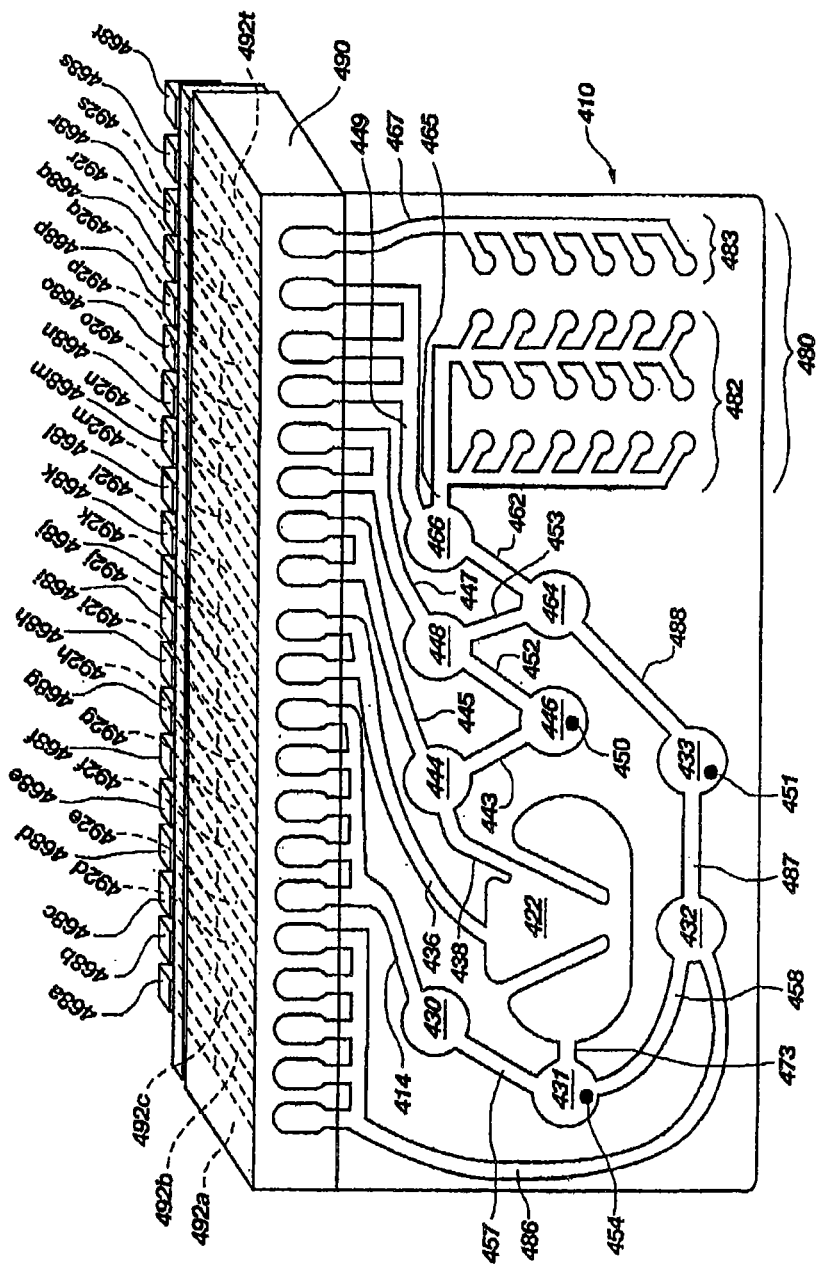
FIG. 13 is an exploded perspective view of the second-stage high density array of FIG. 12A.
Figure 14:
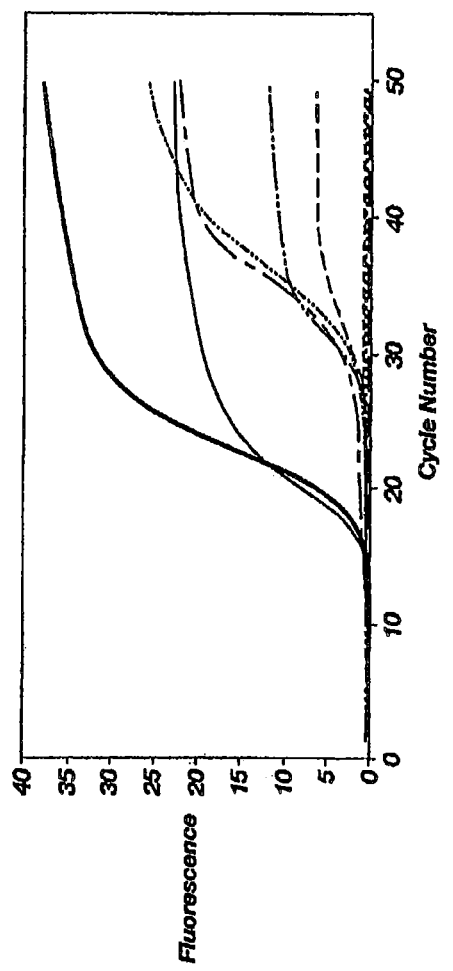
FIG. 14 is a bottom view of the second-stage high density array of FIG. 12A, shown during construction of the second-stage high density array.

FIGS. 12-14 show an illustrative embodiment of second-stage 580 using a physical barrier. Sandwiched between first layer 518 and second layer 519 of pouch 510 is high density array 581, with wells 582. As best seen in FIG. 13, pierced layer 585, with piercings 586, is provided on one side of high density array 581 to act as the physical barrier, and a second layer 587, is provided on the opposite side of high density array 581 to form the bottom of wells 582. Illustratively, pierced layer 585 and second layer 587 are plastic films that have been sealed to high density array 581, illustratively by heat sealing, although it is understood that other methods of sealing may be employed. It is also understood that the material used for high density array 581 and the material used for pierced layer 585 and second layer 587 should be compatible with each other, with the sealing method, and with the chemistry being used. When used for PCR, examples of compatible plastics that can used for high density array 581 and can be heat-sealed are PE, PP, Monprene®, and other block copolymer elastomers. If fluorescent dyes are used in the detection chemistry, it may be desirable for high density array 581 to be formed from black or other relatively fluorescently opaque materials, to minimize signal bleed from one well 582 to its neighboring wells and for at least one of layers 585 and 587 to be relatively fluorescently transparent. For pierced layer 585 and second layer 587, laminates of a strong engineering plastic such as Mylar® or PET with heat-sealable plastic layers such as PE, PP and Dupont Surlyn® may be used. For adhesive-based systems, rigid engineering plastics such as PET or polycarbonate may be used to form high density array 581 and films of PCR-compatible plastics are then used as pierced layer 585 and second layer 587. In one illustrative embodiment, high density array 581 is formed of black PE, a composite polyethylene/PET laminate (or Xerox® PN 104702 hot laminating pouch material) is used for pierced layer 585 and second layer 587 which are heat sealed to high density array 581, and composite polypropylene/PET is used for first and second layers 518, 519 of pouch 510.

It is understood that piercings 586 align with wells 582. It is also understood that piercings 586 are small enough that, absent some force, fluid does not readily flow through piercings 586. Illustrative piercings may be 0.001-0.1 mm, more illustratively 0.005-0.02 mm, and more illustratively about 0.01 mm. In the illustrative embodiment, second-stage amplification zone 580 is provided under vacuum, such that when fluid is received from blister 566, the vacuum draws fluid through piercings 586 into each well 582. Once the wells 582 are filled, a force is no longer present to force fluid into or out of the wells 582. A bladder adjacent second-stage amplification zone 580 (not shown, but similar in position to bladders 880/882) may then be activated to press first layer 518 against high density array 581 and seal fluid into the wells 582. While first layer 518 of pouch 510 is used to seal the wells 582, it is understood that an optional sealing layer may be provided between pierced layer 585 and first layer 510.

In one illustrative example, second-stage amplification zone 580 may be prepared as follows. High density array 581 may be prepared by first punching, molding, or otherwise forming an array of wells 582 in a plastic sheet (illustratively 0.1 to 1 mm thick). The wells may form any regular or irregular array that is desired, and may have a volume illustratively of 0.05 µl to 20 µl, and more illustratively of 0.1 µl to 4 µl. One of layers 585 or 587 is then laminated to a first surface 581a of high density array 581, illustratively by heat or adhesive. As shown in FIG. 14, pierced layer 585 is applied to first surface 581a. Reagents 589, illustratively elements of the chemistry of the array that are unique, such as PCR primer pairs, are then spotted into the wells either manually by pipetting, or automatically (illustratively using x/y positionable spotters such as pin-spotters, dot-matrix printers, small-volume automatic pipettes, or micro-fluidic micro-contact spotters). After the reagents 589 have been dried in each well 582, the second of layers 585 or 587 is applied to the second surface 581b of array 581. Layer 585 is pierced using an array of small diameter needles to form piercings 586. Piercings 586 may be formed either before or after layer 585 has been fixed to array 581. It is understood that spotting can be done on either layer 585 before or after piercing or on layer 587. Spotting an array with holes pre-pierced has not shown to leak substantially and offers the advantage that the needles used for piercing are not contaminated by touching the spotted reagents. Alternatively, to minimize the possibility of leakage, and to position the spotted reagents at the most distant location in the array, it may be desirable to spot the reagents 589 onto second layer 587, seal the array 581 with layer 585, and then pierce layer 585. In an illustrative example, reagents are spotted onto second layer 587 using a GeSiM A060-324 Nano-Plotter 2.1/E (Grosserkmannsdorf, Germany). Using such a spotter, multiple arrays may be spotted simultaneously.

Once spotted and pierced, array 581 is placed inside layers 518 and 519 of pouch 510 and sealed in place, illustratively by either heat sealing, using an adhesive, ultrasonically welding, mechanical closure, or other means of enclosing array 581 inside pouch 51Q within blister 584. It is understood that blister 584 is fluidly connected to blister 566 via channel 565, and that liquid can flow from channel 565 into blister 584 and over piercings 586. In one illustrative example, when blister 584 is formed, care is taken to allow a path for air to escape. This can be accomplished by "waffling" the inside surface of first layer 518 adjacent to second-stage amplification zone 580 to imprint the film material with a pattern of slightly raised texture. This allows air and liquid to pass along the surface of pierced layer 585, and better allows liquid to reach and fill all of wells 582. The pouch 510 is then placed inside a vacuum chamber and evacuated. Illustratively, when the pressure has reached approximately 0.3 millibars, a pneumatic cylinder inside the vacuum chamber is actuated, driving down a plunger into fitment 590 to seal channel 567, thereby cutting the path from the array inside the sealed pouch, and the vacuum chamber. A plurality of other plungers are also driven into fitment 590 to seal the various entry channels 515. The pouch is removed from the vacuum chamber and may be packaged for long-term storage in a vacuum-bag.

Pouch 510 may be used in a manner similar to pouch 210. Because array 581 is packaged in vacuum, when liquid is moved from blister 566 to second-stage amplification zone 580, the liquid sample is drawn through piercings 586 and into wells 582. Excess liquid is forced away by inflating a pneumatic bladder over the array and thermal cycling is accomplished as described above, illustratively by heating and cooling a Peltier element pressed against one side of the array.

As mentioned above, pierced layer 585 may be replaced by a variety of suitable physical or chemical barriers. In one illustrative embodiment using a chemical barrier, pierced layer 585 is omitted, and reagents 589 are spotted into wells 582 in a buffer that dissolves relatively slowly. Illustratively, reagents 589 that contain polymers such as PEG, Ficoll or polysorbate 20 or sugars such as sucrose, trehalose or mannitol in appropriate concentrations will be compatible with the second-stage PCR reaction and may dissolve more slowly than primers spotted solely in water or Tris/EDTA. The primers spotted in one of these buffers may be air dried into the wells 582, as described above (it is understood that in such an embodiment, second layer 587 is affixed to high density array 581 for spotting). These same polymers may be used in lyophilization of enzyme reagents (e.g. the enzymes and buffers used in PCR) to form an open matrix containing the stabilized enzymes. Thus, the primers spotted in these buffers can be lyophilized in place in the wells 582, leading to slower but potentially more complete rehydration than with air drying. When pouch 510 is used, the fluid from blister 566 is driven into the well by vacuum or pressure and starts to dissolve the primer mix. By selecting a buffer that dissolves suitably slowly, when the bladder adjacent second-stage amplification zone 580 is actuated, the contents of each well 582 is sealed therein prior to any substantial cross-contamination.

Another embodiment uses a matrix that does not dissolve until second-stage amplification zone 580 is heated above a predetermined temperature. One example of such a matrix is low melt agarose such as GenePure LowMelt Agarose (ISC Bioexpress). In one example, a 1.5% solution of this agarose melts at 65° C. and gels at 24-28° C. Prior to spotting, reagents 589 illustratively may be warmed to 50° C. and mixed with this agarose that had already been melted and then spotted into wells 582 in a small volume (illustratively 100 to 500 nl). To keep the mixture liquid during spotting, this may have to be done in a cabinet heated above the melting temperature of the agarose. Alternatively, it may be possible to pipette dilute solutions of the agarose without melting. After the agarose/reagent mixture is spotted, the high density array 581 is dried. This can be a simple air drying or the primer-agarose mixture can contain the sugars and polymers listed above so that the reagents can be freeze dried. When pouch 510 is used for PCR, second-stage amplification zone 580 may be heated, illustratively to 55° C., as the fluid from blister 566 is moved into high density array 581. At this temperature, the agarose does not melt so the primers are not released into solution. Once high density array 581 is filled, the corresponding bladder is inflated to seal the wells. When the temperature rises above 65° C. in the first denaturation step of the first PCR cycle, the agarose containing the primers melts, releasing the primers into the master mix. Illustratively, thermal cycling never goes below 60° C. (or other melting temperature for the agarose) so that the agarose does not gel during thermal cycling. Furthermore, in the illustrative instrument 800 of FIG. 8, the repeated temperature cycling is driven by heater 888, which is located on one side of the pouch. It is expected that there will often be a temperature gradient across the PCR solution in wells 582, which should facilitate mixing of the primers by convective fluid flow. Wax may also be used in a similar embodiment.

In a further embodiment, the primers may be conditionally bound to the wells 581, with subsequent releasing of the primers into solution after the wells 581 have been filled. Depending upon how the primers are attached to the plastic substrate, the primers may be cleaved using heat (illustratively during the first cycle of the PCR reaction), light (illustratively irradiating through window 847), chemicals (e.g. dithiothreitol together with heat will reduce disulfide bonds that may be used to link primers to the wells), or enzymes (e.g. site specific proteases such at Tissue Plasminogen Activator can be used to cleave the proper peptide linker attaching primers to the substrate).

In yet another embodiment, a DNase may be injected into second-stage amplification zone 580 subsequent to amplification, to minimize further any potential risk of contamination.

It is understood that second-stage amplification zone 580 has been described herein for use with PCR. However, other uses for pouch 510 and second-stage amplification zone 580 are within the scope of this invention. Further, it is understood that second-stage amplification zone 580 may be used with or without nucleic acid extraction and a first stage PCR amplification zone. Finally, it is understood that second-stage amplification zone 580 may be used with any of the pouch embodiments described herein.

EXAMPLE 1: NESTED MULTIPLEX PCR

A set of reactions was run in a pouch 110 of FIG. 5A, on an instrument similar to instrument 800 but configured for pouch 110. To show cell lysis and effectiveness of the two-stage nucleic acid amplification, 50 µL each of a live culture of S. cerevisaie and S. pombe at log phase was mixed with 100 µL of a nasopharyngeal aspirate sample from a healthy donor to form the sample, then mixed with 200 µL lysis buffer (6M guanidine-HCl, 15% TritonX 100, 3M sodium acetate. 300 µL of the 400 µL sample in lysis buffer was then injected into chamber 192a of pouch 110.

The pouch 110 was manufactured with 0.25 g ZS beads sealed in three-lobed blister 122. Second-stage primers, as discussed below, were also spotted in blisters 181 and 182 during manufacture of pouch 110. The pouch 110 was loaded as follows:
115a sample and lysis buffer, as described above,
115b magnetic beads in the lysis buffer,
115d-e wash buffer (10 mM sodium citrate),
115g elution buffer (10 mM Tris, 0.1 mM EDTA)
115h first-stage PCR buffer:
0.2 mM dNTPs
0.3 µM each primer:
  Sc1: primers configured for amplifying a portion of the YRA1 nuclear protein that binds to RNA and to MEX67p of S. cerevisaie. The primers are configured to amplify across an intron such that amplification of cDNA (mRNA reverse-transcribed via M-MLV) yields a 180 bp amplicon.
  Sc2: primers configured for amplifying a 121 bp region of the cDNA of MRK1 glycogen synthase kinase 3 (GSK-3) homolog of S. cerevisaie.
  Sc3: primers configured for amplifying a 213 bp region of the cDNA of RUB1 ubiquitin-like protein of S. cerevisaie.
  Sp1: primers configured for amplifying a 200 bp region of the cDNA of suc1-cyclin-dependent protein kinase regulatory subunit of S. pombe.
  Sp2: primers configured for amplifying a 180 bp region of the cDNA of sec14-cytosolic factor family of S. pombe.
PCR buffer with 3 mM $MgCl_2$ (without BSA)
50 units M-MLV
4.5 units Taq:Antibody
100 units RNAseQut
115j-k second-stage PCR buffer
0.2 mM dNTPs
1×LC Green® Plus (Idaho Technology)
PCR buffer with 2 mM $MgCl_2$ (with BSA),
4.5 units Taq
115l second-stage PCR buffer with a sample of the first-stage amplicons.

During manufacture, second-stage blisters 181 and 182 were spotted with nested second-stage primers. Each blister was spotted with one primer pair in an amount to result in a final concentration of about 0.3 µM once rehydrated with the second-stage PCR buffer. The second-stage nested primers are as follows:
  Sc1: primers configured for amplifying an 80 bp fragment of the Sc1 cDNA first-stage amplicon.
  Sc2: primers configured for amplifying a 121 bp fragment of the Sc1 cDNA first-stage amplicon.
  Sc3: primers configured for amplifying a 93 bp portion of the Sc1 cDNA first-stage amplicon.
  Sp1: primers configured for amplifying a 99 bp portion of the Sc1 cDNA first-stage amplicon.
  Sp2: primers configured for amplifying a 96 bp portion of the Sc1 cDNA first-stage amplicon.
There is no overlap between the first-stage and second stage primer pairs for any of the targets. Each pair of primers was spotted into one negative control blister 181 and two second-stage blisters 182, so that each second-stage amplification would be run in duplicate, each duplicate with a negative control.

After loading, activation of the plunger associated with entry channel 115a moved the sample to three-lobed blister 122, activation of the plunger associated with entry channel 115b moved the magnetic beads to reservoir 101, activation of the plungers associated with entry channels 115*d-e* moved wash buffer to reservoirs 102 and 103, activation of the plunger associated with entry channel 115*g* moved elution buffer to reservoir 104, activation of the plunger associated with entry channel 115*h* moved first-stage PCR buffer to reservoir 105, activation of the plungers associated with entry channels 115*j-k* moved second stage PCR buffer to reservoirs 106 and 107, and activation of the plunger associated with entry channel 115*l* moved the positive control (second-stage PCR buffer with a sample of previously prepared first-stage amplicon) to reservoir 108. In this present example, the plungers associated with entry channels 115*a* and 115*b* were depressed prior to loading the pouch 110 into the instrument. All other plungers were depressed sequentially in the instrument during the run, and fluids were moved to reservoirs 102 through 108 as needed.

Once pouch 110 was placed into the instrument, and beating took place for ten minutes in the presence of ZS beads, as described above. Once cell lysis was complete, reservoir 101 was compressed and nucleic acid binding magnetic beads from reservoir 101 were forced into three-lobed blister 122, where the beads were mixed gently and allowed to incubate for 5 minutes.

The sample-bead mixture was then moved to blister 144, where the magnetic beads were captured via activation of the magnet. Once the magnet was deployed, bladders adjacent blister 144 were pressurized to force fluids back to three-lobed blister 122. The captured beads were then washed as described above, using the wash solution from reservoirs 102 and 103. Following washing, the beads were once again captured in blister 144 via activation of the magnet, and the elution buffer stored in reservoir 104 is moved to blister 144, where, after a 2 minute incubation, the nucleic acids eluted from the beads are then moved to blister 161, as discussed above.

In blister 161, the nucleic acid sample is mixed with first-stage PCR master mix from reservoir 105. The sample is then held at 40° C. for 10 minutes (during which time M-MLV converts mRNA to cDNA), then 94° C. for 2 minutes (to inactivate the M-MLV and remove antibody from taq). Thermal cycling is then 20 cycles of 94° C. for 10 second and 65° C. for 20 seconds.

Subsequent to first-stage amplification, the sample is diluted approximately 100-fold using the second-stage PCR master mix from reservoir 106. The sample is then moved to blisters 182, which were previously spotted with the second-stage primers, as discussed above. Second-stage PCR buffer was moved from reservoir 181 to negative control blisters 181, and the positive control mixture was moved to blisters 183 from reservoir 108. The samples were denatured for 30 seconds at 94° C., then amplified for 45 cycles of 94° C. for 5 seconds and 69° C. for 20 seconds.

Figure 11:
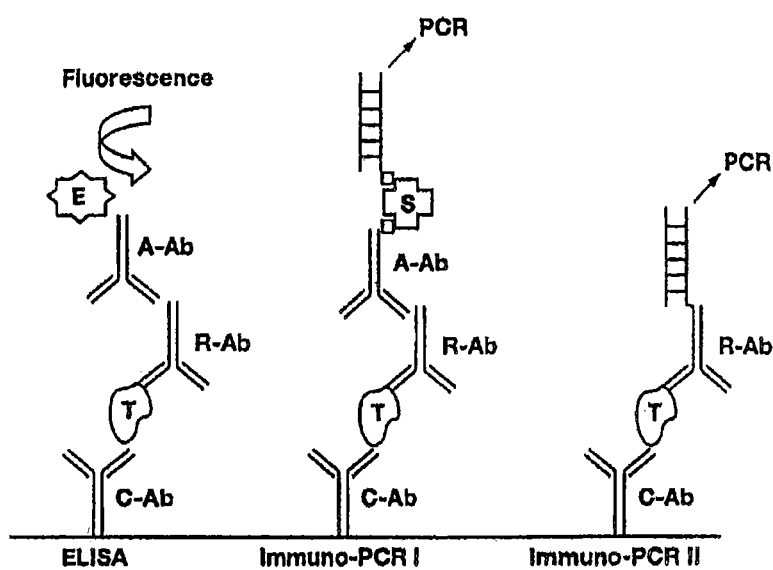
FIG. 11 shows amplification curves from second-stage amplification of a sample that was lysed and amplified in a pouch of FIG. 5A (– – – positive control; – – – S. cerevisaie target 1; ——— S. cerevisaie target 2; ——— S. cerevisaie target 3; – – – – – – S. pombe target 1; ——— – – – S. pombe target 2; - - - - negative controls).

As can be seen in FIG. 11, all target amplicons and the positive control showed amplification, while none of the negative controls showed amplification. Each sample was run in replicates. The replicates each showed similar amplification (data not shown).

It is understood that the *S. cerevisaie* and *S. pombe* targets are illustrative only and that other targets are within the scope of this invention.

EXAMPLE 2: HIGH DENSITY PCR

The above example uses pouch 110 of FIG. 5A. Pouch 110 has five negative control blisters 181, five positive control blisters 183, and ten low volume sample blisters 182. Pouch 210 of FIG. 6A increased the number of low volume sample blisters 282 to 18. However, high density array 581 of pouch 510, shown in FIG. 12A can have 120 or more second-stage wells 582. This increase in the number of second-stage reactions enables a wide set of potential diagnostic and human identification applications without the need to increase the size of the pouch and its instrument. Various examples are described herein.

In one example, it is known that standard commercial immunofluorescence assays for the common respiratory viruses can detect seven viruses: Adenovirus, PIV1, PIV2, PIV3, RSV, Influenza A, and Influenza B. A more complete panel illustratively would include assays for additional five viruses: coronavirus, human metapneumovirus, BOCAvirus, Rhinovirus and non-HRV Enterovirus. For highly variable viruses such as Adenovirus or HRV, it is desirable to use multiple primers to target all of the branches of the virus' lineage (illustratively 4 outer and 4 inner primer sets respectively). For other viruses such as coronavirus, there are 4 distinct lineages (229E, NL63, OC43, HKU1) that do not vary from one season to another, but they have diverged sufficiently enough that separate primer sets are required. The illustrative complete respiratory virus panel would also target the SARS coronavirus, possibly the avian influenza HA and N subtypes, and possibly others. Finally, some of the respiratory viruses show such a high rate of sequence variation that it would be beneficial to create more than one nested PCR assay for each such virus, thereby minimizing the chance of false negative results due to sequence variation under the primers. When all of the primer sets described herein are included, such a respiratory virus panel could have 80 or more specific amplicons in the second-stage amplification. The high density array 581 could easily accommodate such a panel in a single pouch 510.

A second application of the high density array 581 of pouch 510 would be to determine the identity and the antibiotic resistance spectrum of the multi-drug resistant bacteria isolated from infected patients. Current methods require several days to culture the organism and empirically test individual drug resistance profiles. During the time it takes to receive the results, physicians will often administer broad-spectrum antibiotics, which leads to an increase in multi-drug resistant bacteria. PCR primers have been developed to detect the genetic determinants of antibiotic resistance (the antibiotic resistance genes themselves). However because of the large number of variants of some of these genes, a large number of amplicons is required for a complete determination of the resistance profile. Hujer et. al. describe a panel of 62 PCR assays to identify the resistance genes present in *Acinetobacter* isolates. Again, the high density array 581 could easily accommodate such a panel in a single pouch.

A third example of the utility of the high density array is in the field of human identification, illustratively for forensic identification of human remains and for paternity testing. Most of the market in human identification is dominated by systems that analyze short tandem repeat sequences (STRs). This analysis has generally required separating the repeats by size, using e.g. capillary electrophoresis. The specialized laboratory equipment used for this purpose has generally not been field portable. There is growing interest in using Single Nucleotide Polymorphisms (SNPs) for identity testing, as there are a large set of techniques for identifying SNPs and some of these are amenable to field use. Sanchez et al. have published a set of 52 well-characterized SNPs that collectively give a very low probability of matching two individuals by chance (a mean match probability of at least $5.0 \times 10^{-19}$). In practice, it may take two amplicons for each SNP to accurately type each locus (see, e.g., Zhou et al.). Thus one pouch 510 with 104 second-stage wells 582 could completely type an individual at all of the 52 SNP loci.

It is understood that there are cost and workflow advantages gained by combining assays from different diagnostic applications into one pouch. For example the complete respiratory virus panel could be combined with the bacterial identification panel. These combinations could simplify manufacturing, since there are fewer types of pouches to assemble. They could also simplify the work of the end user, as there are fewer specific types of pouches that need to be stocked in a clinic, and also reducing the chance of using the wrong pouch for a particular clinical sample. For some applications, these advantages could offset an increase cost of manufacturing the pouch having a greater number of primer pairs. Thus one pouch 510 with 100 or more second-stage wells 582 could be used to accommodate multiple panels of assays.

EXAMPLE 3: PROCESS CONTROLS

Controls for highly multiplexed assays can be problematic, especially in clinical diagnostic settings where quality must compete with cost per test. The high-density array 582 of pouch 510 potentially increases this problem because of the increased number of diagnostic targets that can be assayed in a single run. Various types of controls are discussed herein.

Illustrative process controls include mixing an intact organism, for example an organism containing an RNA target, into the patient sample before injecting the sample into the pouch. Such a target could be an intact RNA bacteriophage (MS2 or Qβ) or an intact plant RNA virus (Tobacco Mosaic Virus) or an mRNA present in an intact yeast. Outer primers specific for the RNA target would be present in the first-stage PCR and a well 582 containing the inner primers would be present in the high density array. Detection of amplification product in this well 582 confirms that all of the steps of the process are working correctly. A post-second-stage amplification melt curve could also be used to verify that the correct specific product was made. The crossing point ("Cp") determined from an amplification curve could be used to give a quantitative measure of the integrity of the reagents. For example the Cp can be compared to that of other pouches from the same lot run at a different time. While an intact organism is used, it is understood that purified or isolated nucleic acids may be used if it is not important to test for lysis. In other situations, it may be desirable to use the control to test only the later steps of the analysis. For example, spiking a natural or synthetic nucleic acid template into a well in the high density array along with the cognate primers could be used to test the second-stage PCR reaction, and spiking a nucleic acid template into the first-stage PCR with the appropriate primers in the first-stage PCR amplification mixture and in a well 582 of the second-stage amplification zone will test both the first- and second-stage PCR reactions.

Process controls such as described above do not test the integrity of the primers specific to the target amplicons. One example of a positive control that tests the integrity of the specific primers uses a mixture of nucleic acids, illustratively synthetic RNAs, as stability and variability often can be better controlled and these sequences cannot be present due to environmental contamination, wherein the mixture contains a nucleic acid for each of the primers present in the particular pouch. In a diagnostic setting, this positive control could be used at the end of a run of pouches used to test patient samples. The mixture is injected into a pouch, illustratively from the same lot as those used for the patient samples, and success is defined by all of the target amplicons providing a positive result. Negative controls can be done in the same way; at the end of a run of pouches used to test patient samples, water or buffer could be injected into a pouch and success defined by all of the target amplicons providing a negative result.

Individual workflow and protocols in a diagnostic lab may be used to determine the number of patient sample pouches run before the control pouches described above are run. Regardless of how frequently or infrequently the control pouches are run, these controls add to the time and cost of the total system. For this reason, it would be useful to make the controls internal to the pouch. The structure of the high density array 581 allows for the following novel approach to negative controls. In this example, a nucleic acid, illustratively a synthetic amplicon, is spiked into one of the wells 582a of the high density array 581. Primers to amplify this sequence are spiked into this well 582a and into two other wells 582b and 582c spaced across the array. Illustratively, the amplicon sequence and primers are artificial and designed so that none of the primers used will amplify another target by chance.

When a clean, uncontaminated pouch 510 is run in instrument 800, the well 582a containing the synthetic target will generate amplicon and therefore be called positive. The two other wells 582a, 582b that contain the corresponding primers should not amplify anything in the sample and thus be called negative. Pouch 510 may be treated further, for additional controls. Illustratively, bladder 880/882 holding the high density array against heater 888 is then depressurized and the contents of the wells 582 are mixed. In one illustrative method, the contents of the wells 582 are mixed as follows: heater 888 is used to cycle the temperature of the high density array above and below the boiling point of the buffer for a short time (for example three cycles of 85° C. for 10 sec then 105° C. for to 20 sec). Bubbles of steam generated in the wells 582 of high density array 581 should force the contents of wells 582 out into the second-stage amplification zone blister 580. Optionally, the contents of the second-stage amplification zone 580 may be mixed with the contents of rest of the pouch 510 by using the bladders to move liquid from one end of the pouch 510 to the other. The purpose of these steps is to mix the specific contamination control amplicon, along with any specific target amplicons throughout the pouch.

If the user accidentally opens a pouch after it has been run in this fashion, then both specific target amplicons and the contamination control amplicon will be released. If trace amounts of these nucleic acids contaminate a later pouch run, the instrument may detect the contamination event, as the wells 582b, 582c that contained only the primers specific for the synthetic amplicon will score positive. Software in the instrument will alert the user and the results of the run will be flagged as suspect.

In another method to control contamination, at the end of a run, a DNA degrading chemical or enzyme may be added to destroy substantially all of the DNA products of the first- and second-stage PCR reactions. Illustratively, this can be done in a way similar to the contamination detection method described above, by heating the contents of the second-stage array to above the local boiling temperature, thus drawing the amplified sample out of the wells 582 of the array 851, mixing the heated liquid with the diluted contents of the 1$^{st}$ stage reaction, adding an aliquot of a DNA degrading substance, illustratively through entry channel 515k, either with or without cooling the mixture, and allowing the DNA degrading reaction to incubate until substantially all of the DNA produced in the PCR reaction has been destroyed. This can be accomplished using DNAses, acids, or oxidants, as are known in the art.

It is understood that any of the contamination controls described herein may be used independently or in any combination thereof.

EXAMPLE 4: BACTERIAL IDENTIFICATION PANEL

The above instruments and pouches allow for a large number of reactions in a single, sealed environment. This is particularly true of pouch 510, which may optionally have 100 or more second-stage reaction wells 582. The large number of second-stage reactions available in pouch 510 allows a robust identification strategy for organisms, illustratively bacteria, by allowing the interrogation of a number of genes for each species (illustratively housekeeping genes are used, as described below). The genes may be amplified in a first-stage multiplex reaction using outer first-stage primers targeting conserved sequences, and then subsequently amplified in individual second-stage reactions using inner second-stage primers targeted more specifically to the individual species. This strategy allows for the detection and identification of an unknown (and unspecified) pathogenic bacterium using a single set of assays performed in a closed system, with results available in real time. By combining tests for a wide range of bacteria into a single assay, the problems a clinician faces when having to order individual assays for each bacterial species can be reduced or avoided. This strategy may also reduce or eliminate the need for sequencing of the PCR amplicon for organism identification.

One illustrative application of this method is the identification of bacteria infecting infants in the first 90 days of life. Pediatric guidelines recommend aggressive evaluation of infants ≤28 days old for serious bacterial infection, including cultures for bacterial pathogens from blood, urine and, cerebral spinal fluid. While awaiting results of these cultures, which can take from 24-48 hours, infants are often hospitalized and placed on broad-spectrum antibiotics.

When an organism is identified, antibiotic susceptibility testing is often required, and can be complex, particularly for organisms showing resistance to certain classes of antibiotics. For example, for Gram-negative organisms showing resistance to third-generation cephalosporins, guidelines have been developed for detection of the extended-spectrum β-lactamase (ESBL) phenotype (18). However, from a laboratory standpoint, ESBL testing is labor-intensive (19), and from a clinical standpoint, such testing can be misleading, as sometimes susceptible isolates in vitro are resistant under treatment conditions (18-20). Delays in testing or misreporting of susceptibility data often results in prolonged use of broad-spectrum agents or the risk of inadequate therapy.

PCR-based detection of antibiotic resistance is becoming more common. In particular, detection of methicillin-resistance in *S. aureus* by identification of the mecA gene has become widely accepted and is common in clinical settings. However, despite the identification of these genetic determinants of antibiotic resistance, molecular testing for other resistance genes has not been widely used. This likely is due to the complexity of the genetics. For example, over 200 ESBL genotypes have been characterized, reflecting multiple mutations in seven or more plasmid-encoded genes. Diagnostic strategies such as those illustrated here, capable of high-order multiplex analysis and the flexibility to change as the resistance landscape evolves, will aid in the development of rapid testing for these resistance determinants.

Currently, molecular testing is not routinely available for any of the bacterial pathogens common in young infants. Even limiting the list of bacteria tested to that of those most likely found in these infants, this list would include 8-10 organisms, and if molecular testing were available, traditional PCR methods would require a minimum of 8-10 separate tests. Alternately, using currently described broad-range PCR strategies, a sequencing step, taking almost as long as culture, would be necessary for identification. A strategy such as that presented in this Example could allow for interrogation of blood or CSF or other sterile body fluid for multiple pathogens in a single assay with results potentially available at the point-of-care. By way of example, 27 pathogens (4 genes*27 pathogens=108 wells+12 control wells=120 total second-stage reaction wells 582 in the high-density array) may be tested in a single pouch 510.

It is known that different groups of patients have different likelihoods of infection with particular organisms based on their age, presenting location (for example, inside or outside the hospital), and underlying immunity. By designing broad-range outer primer sets for conserved genes for first-stage PCR, the present strategy allows for the modification of second-stage inner primer sets to target different populations of patients. In the example described above with respect to infants, inner second-stage PCR targets illustratively would include (but not be limited to) *Neisseria meningitidis, Haemophilus influenzae, Escherichia coli, Klebsiella pneumoniae, Streptococcus pneumoniae, Streptococcus agalactiae, Staphylococcus aureus* and *Listeria monocytogenes*. It is understood that this list is exemplary only and that the list of second-stage targets may be adjusted due to a wide variety of factors. Other populations that could be targeted include: patients in the intensive care unit, (ICU panel illustratively including *Pseudomonas aeruginosa, Enterobacter cloacae, Klebsiella oxytoca* and *Serratia marscescens*), and patients with malignancy and immunity suppressed by chemotherapy (illustratively febrile neutropenic panel, including opportunistic pathogens such as *Staphylococcus epidermidis, Pseudomonas aeruginosa*, and Viridans group Streptococci). Illustratively, in each case the optimized first-stage outer primer set may remain unchanged, but the panel of second-stage inner primers would be modified for the target population.

This strategy could also be used for identification of organisms from culture, particularly in cases where a patient is not responding to antibiotics, and rapid organism identification might direct antibiotic therapy more appropriately, or in situations, such as possible infection with *Neisseria meningitidis* (meningococcemia) where rapid species confirmation is crucial to the initiation of prophylaxis for contacts.

In addition, it is possible that this strategy may allow the identification of novel strains of bacteria causing disease by identifying bacteria based on a Cp and/or post-second-stage amplification melting curve "fingerprint." Due to the broad-range design of first-stage outer primers, which are likely to amplify targets from even unknown bacteria, along with expected cross-reactivity of inner second-stage primers with non-target organisms, a novel bacterium may have a "fingerprint" not previously encountered. It is also possible that different strains of the same species of bacteria might generate unique "fingerprints" (either by Cp pattern or post-second-stage amplification melting curves) and thus this technique may allow epidemiologic tracing of bacteria and outbreaks of infection. Currently, multi locus sequence typing (MLST) can be used for this purpose, but this technique takes a significant period of time to perform. The present strategy would allow for rapid identification of an outbreak, illustratively by coding instrument 800 to detect when unique Cp patterns are seen at a high frequency over a short period of time.

Theoretical Support for the Strategy:

With the advent of genomic sequencing, systematic bacteriology has worked to come up with a definition of "species" based on genomic sequencing (Gupta. Micro and Mol Biol Rev. 1998; 62: 1435, Gupta et al. Theoretical Pop Biol. 2002; 61: 423). The "Report of the Ad Hoc Committee for the Re-Evaluation of the Species Definition in Bacteriology" (Stackebrandt et al. Int J Systemic and Evol Microbial. 2002; 52: 1043) recommends evaluation of "protein-coding genes under stabilizing selection" (housekeeping genes) for their use in phylogenetic studies to differentiate bacterial species from one another. The present strategy uses similar genes applied to the identification of known and well-described pathogenic species, illustratively with results in real-time. The use of the particular genes in the present example is further supported by other studies in which the utility of a range of housekeeping genes in identifying and classifying species has been compared to previously accepted methods such as DNA:DNA reassociation, absolute nucleotide identity and 16S rRNA gene sequencing (Stackebrandt et al. Int J Systemic and Evol Microbiol. 2002; 52: 1043, Konstantinos et al. Appl Environ Micro. 2006; 72: 7286 (multiple genes), Mollet et al. Mol Micro. 1997; 26: 1005 (rpoB), Kwok et al Int J Systemic and Evol Microbiol. 1999; 49: 1181 (hsp60)). Although the present strategy bases gene selection on these types of studies, it is understood that other genes may be used as well.

Primer Design:

The illustrative strategy employs broad-range outer first-stage PCR primers targeting multiple conserved protein-encoding genes and conserved non-protein-encoding sequences such as ribosomal genes. Identification of specific bacterial species is done in individual second-stage wells 582 of a 120 well high-density array, using specific inner second-stage PCR primers for pathogens of interest. The illustrative broad-range outer first-stage primer sets amplify conserved genes in phylogenetically distant bacterial pathogens. It is anticipated that 4-7 genes may need to be interrogated to generate a robust and specific method for bacterial identification; it is possible that, despite directing the assays at conserved genes, a particular strain or isolate may undergo an unanticipated nucleotide sequence change in the region of one assay, which could be rescued by a positive assay for another gene. Illustrative initial gene targets include rpoB (RNA polymerase beta subunit), gyrB (DNA gyrase subunit B), ftsH (conserved membrane protease), ompA (outer membrane protein A), secY (conserved membrane translocon), recA (DNA recombination protein), groEL (hsp60 heat shock protein) and the 16S rRNA gene. Primer design and initial testing is presently underway for rpoB and gyrB.

Due to the fact that the target species come from distant arms of the bacterial phylogenetic tree, the ability to perform simple nucleotide alignment to interrogate for conserved regions is unlikely. By aligning the genes based on their amino acid sequences, it is possible to identify protein domains conserved across species, and it is to the nucleotide sequences of these domains that the outer first-stage primers of the nested assay are designed. By using degenerate primers, it has been found that rpoB and gyrB require only 2 outer first-stage primer sets (one for Gram-positive and one for Gram-negative organisms; 2-4 primers per set, although it is understood that other numbers of primer sets or primers per set could be used, as desired for the particular application) per gene to amplify all target organisms tested (14 species to date). It is possible that other gene targets will require a larger number of outer first-stage primers. By limiting the number of first-stage primer sets in the outer reaction, the multiplex of the first-stage PCR amplification is simplified, thus increasing the chances of a successful assay. Further, the outer multiplex, which is often more sensitive to changes in primer number and sequence, can remain undisturbed if the panel changes, and does not need to be re-validated for all pathogens if one or more pathogen is added or removed. While it is desired to have a single set of first-stage primers and only change the second-stage primers for specific panels, it is also possible that some panels may require unique first-stage primer sets. In the present example, degeneracies in the illustrative outer first-stage primer sets for rpoB and gyrB range from 6 to 32 fold.

Illustratively, desired locations for outer first-stage primers are locations in which two conserved regions, separated by no more than about 500 nucleotide base pairs, bracket a variable region with enough sequence variability to design inner primers specific to particular bacterial species. Such locations were identified in both rpoB and gyrB, and multiple inner primer sets have been designed to the variable regions, each, for the most part, targeting a specific bacterial species. Where possible, the 3'-end of the primer has been designed to lie on a sequence that encodes a "signature" amino acid or acids which is unique to the species being targeted, but different from other bacteria. This diminishes or prevents second-stage amplification unless that species is present. This was not possible in all cases, and some cross-amplification is seen. Illustrative primers developed to date for rpoB and gyrB are shown in Tables 1-3.

Figure 19A:
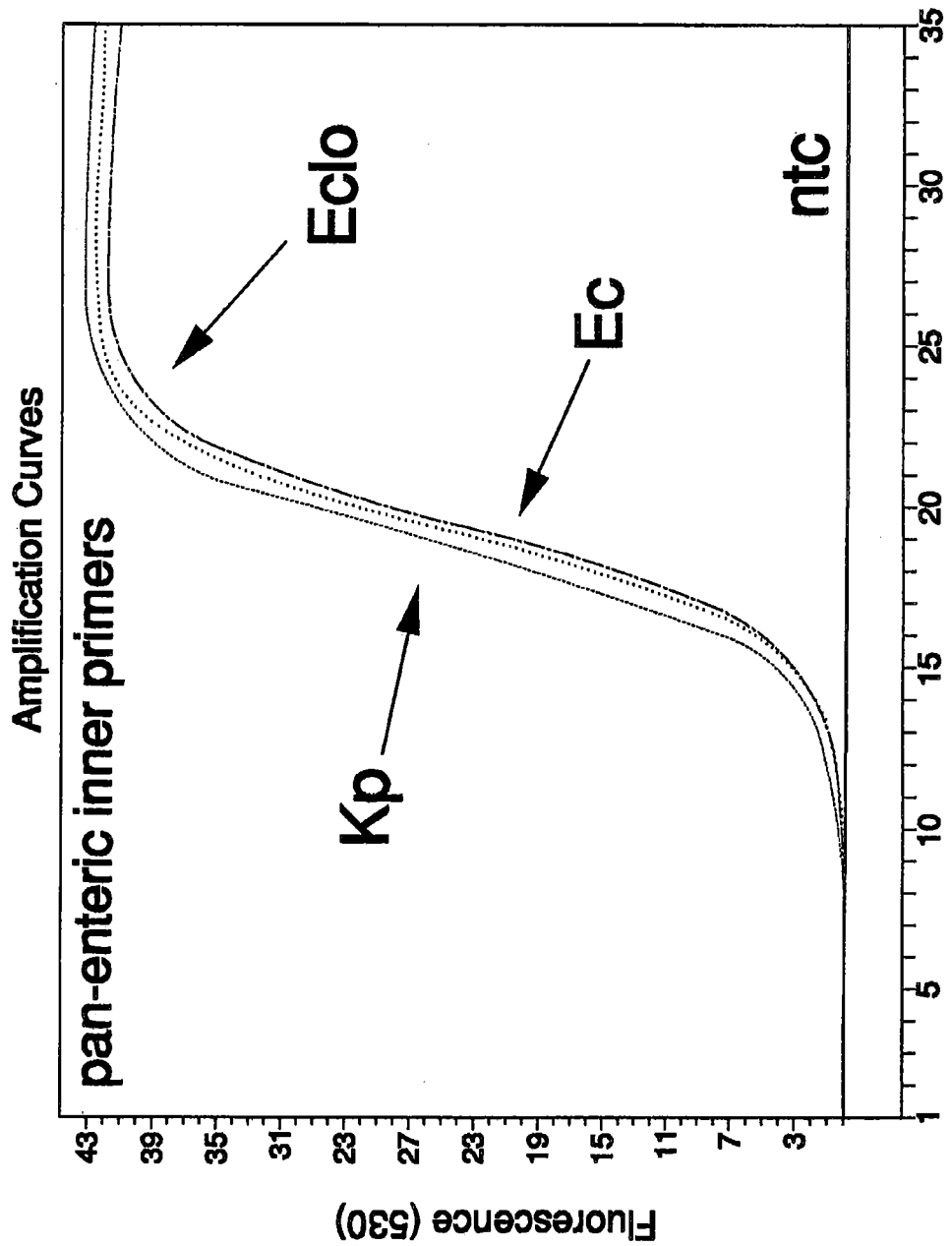
FIGS. 19A-19D show differentiation of enteric organisms using preferential primers in rpoB amplification.
Figure 19B:
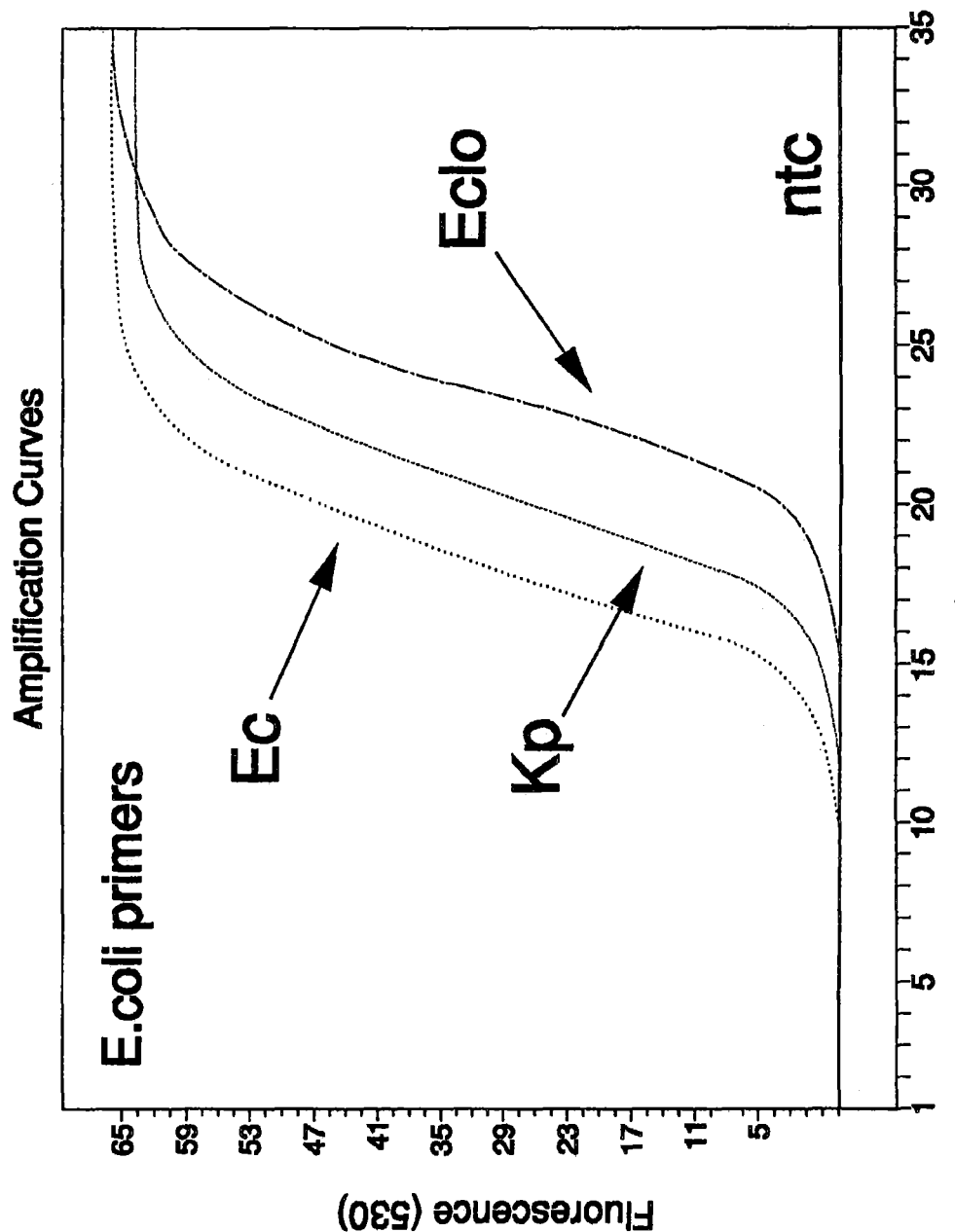
Figure 19C:
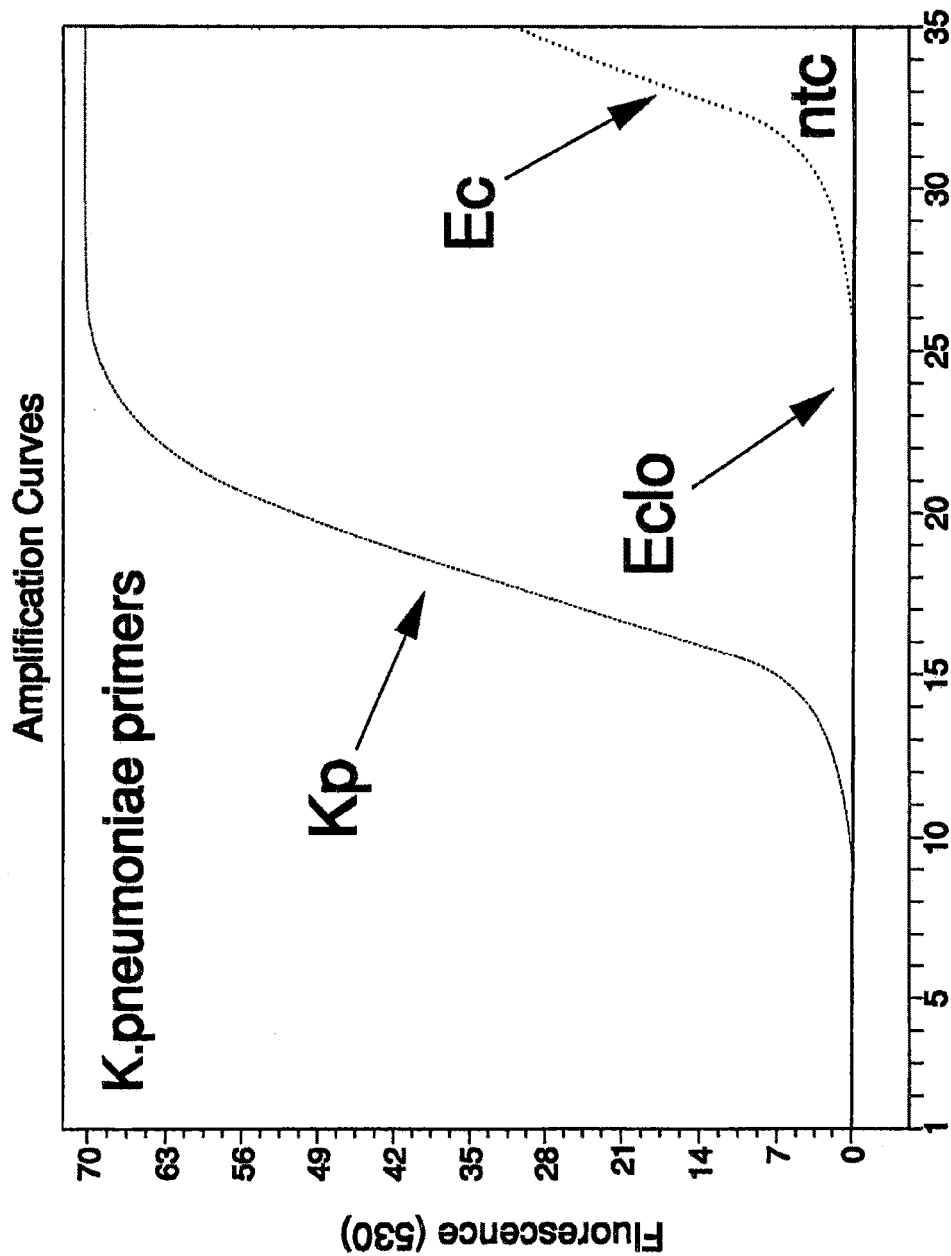
Figure 19D:
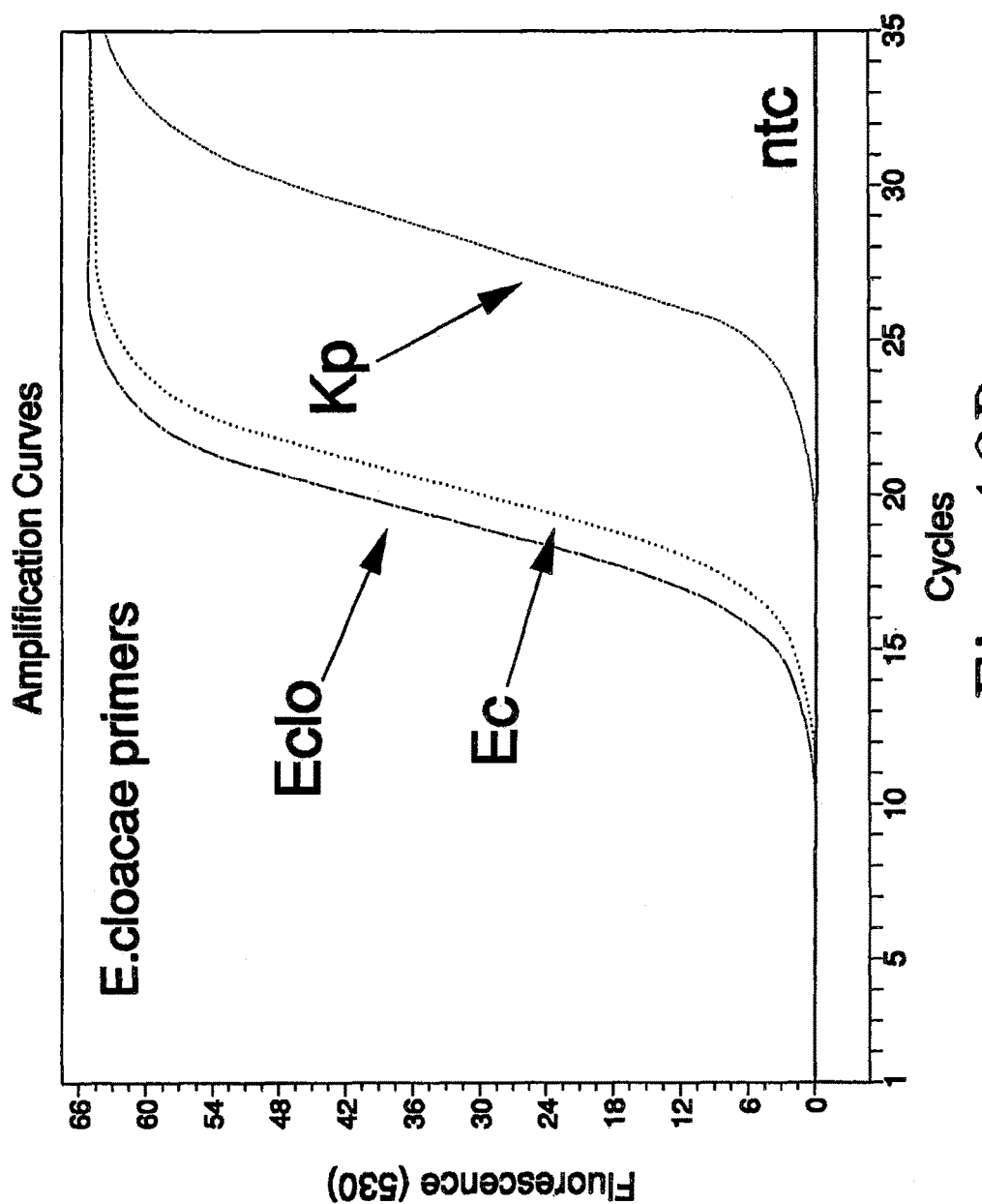
Figures 20A, 20B:
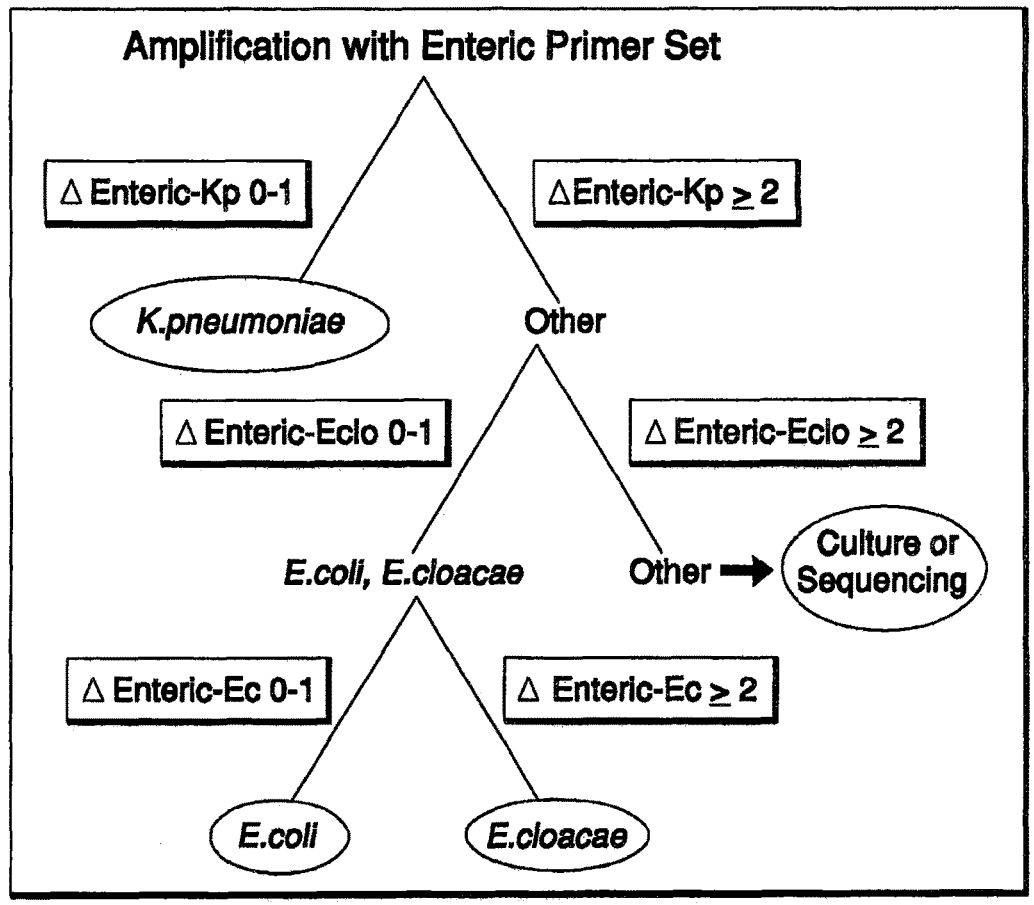
FIGS. 20A and 20B show a decision tree for enteric identification based on Cp fingerprint.

When bacterial species are genetically too similar to be amplified exclusively by a unique set of primers, a "fingerprinting" technique based on the amplification characteristics of a set of primers can be used for species identification. An illustrative example is "enteric" organisms (e.g. *E. coli, K. pneumoniae, K. oxytoca* and *E. cloacae*) in the rpoB gene. These enteric organisms have too much sequence similarity within rpoB, and designing specific inner second-stage primers has proven difficult. Therefore, a "pan-enteric" inner second-stage primer was designed, as well as "preferential" primers, as shown in Table 3. An example of how these primers would be used to generate a fingerprint is shown in FIGS. 19-20. When the preferential inner primers are used, each enteric bacterial template shows a different pattern of crossing points, and each organism amplifies best with its own preferential inner primer set, FIG. 19A shows second-stage amplification with the pan-enteric primers. All three organisms amplified with essentially the same Cp. FIGS. 19A-19D show amplification using the preferential primers for *E. coli, K. pneumoniae*, and *K. oxytoca* and *E. cloacae*, respectively. In this illustrative example, the inner primers for *K. pneumoniae* have the most sequence difference, and, thus, are the most selective, with *K. pneumoniae* having a much earlier Cp (FIG. 19C). FIGS. 20A and 20B show a chart (FIG. 20A) and decision tree (FIG. 20B) that may be used for identification using the Cp fingerprint. As illustrated in Table 3, the bases in bold provide primer specificity. In this illustrative example, the specificity is provided by the forward primers; the reverse primer for the *E. coli, K. pneumoniae* and *E. cloacae* assays is the same.

Enteric organisms can be differentiated from each other in the gyrB assay, as well as potentially by the melting temperature of the rpoB amplicon, depending on sequence variation. An additional strategy for distinguishing closely-related species, for example the enteric organisms already discussed, would be to target a gene which is present within that group, but less-conserved than other housekeeping genes, and not present in other groups of bacteria. Illustratively, an outer membrane protein gene such as ompA (outer membrane protein A), present in the outer membrane of Gram-negative bacteria, but not present in Gram-positive bacteria, could be used. Outer primers would target regions conserved within the closely-related group of organisms, and inner primers would be used to distinguish them. An illustrative set of primers for ompA is shown in Table 4. Thus, it is understood that various combinations of first- and second-stage reactions can be used, including those identifying a particular group of organisms and others specific for a particular target species, for example specific bacterial species.

While the rpoB (RNA polymerase beta subunit), gyrB (DNA gyrase subunit B), and ompA (outer membrane protein A) genes are used in this example, it is understood that other genes may be used as well, including ftsH (conserved membrane protease), secY (conserved membrane protein translocon), recA (DNA recombination protein), groEL (hsp60 heat shock protein) and the 16S rRNA gene. It is understood that these genes are illustrative only, and any combination of these and/or other genes is within the scope of this invention. While variability in the target sequence at the 3'-end may be used to limit cross-amplification, it is anticipated that cross-amplification by the inner primers will occur, possibly in several genes even for the same species. This may lead to a "positive call" for more than one organism-specific assay. Identification of each organism may be made by its "fingerprint" or pattern of amplification (whether amplification occurs and Cp) over all inner primer sets.

TABLE 1

Outer First-Stage Primers: rpoB and gyrB

| Gene | Primer | Sequence |
|---|---|---|
| rpoB | forward Gram-negatives | GGCTTYGARGTDCGDGACG (SEQ ID NO. 1) |
| rpoB | reverse Gram-negatives | RCCCATBARTGCRCGGTT (SEQ ID NO. 2) |
| rpoB | forward Gram-positives | BCACTAYGGBCGYATGTGTCC (SEQ ID NO. 3) |
| rpoB | reverse Gram-positives | AAHGGAATACATGCYGTYGC (SEQ ID NO. 4) |
| gyrB | forward Gram-negatives-1 | TCCGGYGGYYTRCAYGG (SEQ ID NO. 5) |
| gyrB | forward Gram-negatives-2 | TCBGTNGTWAACGCCCTGTC (SEQ ID NO. 6) |
| gyrB | reverse Gram-negatives | RCGYTGHGGRATGTTRTTGGT (SEQ ID NO. 7) |
| gyrB | forward Gram-positives-1 | GGYGGWGGYGGMTAYAAGGTTTC (SEQ ID NO. 8) |
| gyrB | forward Gram-positives-2 | GGMGGYGGCGGMTAYAAAGTATC (SEQ ID NO. 9) |
| gyrB | reverse Gram-positives-1 | TTCRTGMGTHCCDCCTTC (SEQ ID NO. 82) |
| gyrB | reverse Gram-positives-2 | TTCATGCGTACCACCCTC (SEQ ID NO. 10) |

TABLE 2

Inner Second-Stage Primers: rpoB and gyrB

| Gene | Primer Name | Sequence | Target |
|---|---|---|---|
| rpoB | rpoB1Ents.iF04 | CCGTAGYAAAGGCGAATCC (SEQ ID NO. 11) | Enteric organisms |
| rpoB | rpoB1Ents.iR03 | GGTWACGTCCATGTAGTCAAC (SEQ ID NO. 12) | Enteric organisms |
| rpoB | rpoB1Hinf.iF01 | ACTTTCTGCTTTTGCACGT (SEQ ID NO. 13) | H. influenzae |
| rpoB | rpoB1Hinf.iR01 | CTTCAGTAACTTGACCATCAAC (SEQ ID NO. 14) | H. influenzae |
| rpoB | rpoB1Nmen.iF01 | CTCATTGTCCGTTTATGCG (SEQ ID NO. 15) | N. meningitidis |
| rpoB | rpoB1Nmen.iR02 | TCGATTTCCTCGGTTACTTTG (SEQ ID NO. 16) | N. meningitidis |
| rpoB | rpoB1Paer.iF01 | TCAACTCCCTGGCGACC (SEQ ID NO. 17) | P. aeruginosa |
| rPoB | rpoB1Paer.iR01 | CYACGCGGTACGGGC (SEQ ID NO. 18) | P. aeruginosa |
| rpoB | rpoB1Spne.iF03 | AGGTTGACCGTGAAACAGG (SEQ ID NO. 19) | S. pneumoniae |
| rpoB | rpoB1Spne.iF04 | AGGTTGACCGTGCAACTGG (SEQ ID NO. 20) | S. pneumoniae |

TABLE 2 -continued

Inner Second-Stage Primers: rpoB and gyrB

| Gene | Primer Name | Sequence | Target |
|------|-------------|----------|--------|
| rpoB | rpoB1Spne.iR03 | GCTGGATACTCTTGGTTGACC (SEQ ID NO. 21) | S. pneumoniae |
| rpoB | rpoB1Spne.iR04 | GCTGGATATTCTTGGTTAACC (SEQ ID NO. 22) | S. pneumoniae |
| rpoB | rpoB1Spyo.iF01 | YGAAGAAGACGARTACACAGTT (SEQ ID NO. 23) | S. pyogenes |
| rpoB | rpoB1Spyo.iR01 | CGTCAACGAAATCAACAACAC (SEQ ID NO. 24) | S. pyogenes |
| rpoB | rpoB1Saga.iF01 | TGAAGAAGATGAATTTACAGTT (SEQ ID NO. 25) | S. agalactiae |
| rpoB | rpoB1Saga.iR01 | CGTCAACAAAGTCAACAATGC (SEQ ID NO. 26) | S. agalactiae |
| rpoB | rpoB1Saur.iF02 | GTAAAGTTGATTTAGATACACATGC (SEQ ID NO. 27) | S. aureus |
| rpoB | rpoB1Saur.iR01 | CGACATACAACTTCATCATCCAT (SEQ ID NO. 28) | S. aureus |
| rpoB | rpoB1Sepi.iF01 | YTWGATGAAAATGGTCGTTTCYTAG (SEQ ID NO. 29) | S. epidermidis |
| rpoB | rpoB1Sepi.iR01 | GTTTWGGWGATACRTCCATGT (SEQ ID NO. 30) | S. epidermidis |
| rpoB | rpoB1Lmon.iF01 | CKAACTCGAAATTAGACGAACAA (SEQ ID NO. 31) | L. monocytogenes |
| rpoB | rpoB1Lmon.iR01 | TTTTCTACCGCTAAGTTTTCTGA (SEQ ID NO. 32) | L. monocytogenes |
| rpoB | rpoB1Efas.iF01 | ACAGCYGAYATCGAAGACCA (SEQ ID NO. 33) | E. faecalis |
| rpoB | rpoB1Efas.iR01 | ACTTCTAAGTTTTCACTTTGHGC (SEQ ID NO. 34) | E. faecalis |
| rpoB | rpoB1Efas.iI02 | ACTTCTAAGTTTTCACTTTGTAG (SEQ ID NO. 35) | E. faecalis |
| gyrB | gyrB1Hinf.iF01 | ATTCGTCGTCAAGGTCAC (SEQ ID NO. 36) | H. influenzae |
| gyrB | gyrB1Hinf.iR01 | CGATTGAGGCTCCCCTAAA (SEQ ID NO. 37) | H. influenzae |
| gyrB | gyrB1Ecol.iF01 | GTTATCCAGCGCGAGGGTA (SEQ ID NO. 38) | E. coli |
| gyrB | gyrB1Ecol.iR01 | GTGCCGGTTTTTTCAGTCT (SEQ ID NO. 39) | E. coli |
| gyrB | gyrB1Kpne.iF01 | GATAACAAAGTTCACAAGCAGATG (SEQ ID NO. 40) | K. pneumoniae |
| gyrB | gyrB1Kpne.iR01 | GTCGGTTTCGCCAGTCA (SEQ ID NO. 41) | K. pneumoniae |
| gyrB | gyrB1Koxy.iF02 | GTTTCTGGCCGAGCTAYGA (SEQ ID NO. 42) | K. oxytoca |
| gyrB | gyrB1Koxy.iR02 | CGTTTTGCCAGRATYTCGTAT (SEQ ID NO. 43) | K. oxytoca |
| gyrB | gyrB1Eclo.iF01 | TATCCAGCGCGAAGGCA (SEQ ID NO. 44) | E. cloacae |

TABLE 2 -continued

Inner Second-Stage Primers: rpoB and gyrB

| Gene | Primer Name | Sequence | Target |
|---|---|---|---|
| gyrB | gyrB1Eclo.iR01 | GGCCAGAAACGCACCAT (SEQ ID NO. 45) | E. cloacae |
| gyrB | gyrB1Nmen.iF01 | AACACTTCGTCCGCTTCGT (SEQ ID NO. 46) | N. meningitidis |
| gyrB | gyrB1Nmen.iR01 | GCGAGGAAGCGCACGGT (SEQ ID NO. 47) | N. meningitidis |
| gyrB | gyrB1Paer.iF01 | TCGCCACAACAAGGTCTG (SEQ ID NO. 48) | P. aeruginosa |
| gyrB | gyrB1Paer.iR01 | GGCCAGGATGTCCCARCT (SEQ ID NO. 49) | P. aeruginosa |
| gyrB | gyrB1Saur.iF01 | GTCATTCGTTTTAAAGCAGATGGA (SEQ ID NO. 50) | S. aureus |
| gyrB | gyrB1Saur.iR01 | GTGATAGGAGTCTTCTCTAACGT (SEQ ID NO. 51) | S. aureus |
| gyrB | gyrB1Spne.iF01 | AGAATACCGTCGTGGTCAT (SEQ ID NO. 52) | S. pneumoniae |
| gyrB | gyrB1Spne.iR01 | ACCTTGGCGCTTATCTGT (SEQ ID NO. 53) | S. pneumoniae |
| gyrB | gyrB1Spyo.iF01 | AACGACTCAGTTTGATTACAGTG (SEQ ID NO. 54) | S. pyogenes |
| gyrB | gyrB1Spyo.iR01 | AAATGTTCTTCTTGTTCCATACCT (SEQ ID NO. 55) | S. pyogenes |
| gyrB | gyrB1Saga.iF01 | GYAAGGTTCATTATCAAGAATAYCAA (SEQ ID NO. 56) | S. agalactiae |
| gyrB | gyrB1Saga.iR01 | AAGTGAACTGTTGTTCCTGATAAG (SEQ ID NO. 57) | S. agalactiae |
| gyrB | gyrB1Sepi.iF01 | GCTATTCGATTCAAAGCCGATAA (SEQ ID NO. 58) | S. epidermidis |
| gyrB | gyrB1Sepi.iR01 | TCTAACTTCCTCTTCTCTTTCATCTTT (SEQ ID NO. 59) | S. epidermidis |
| gyrB | gyrB1Efas.iF01 | CGTCGTGAAGGACAAGAAGATAAA (SEQ ID NO. 60) | E. faecalis |
| gyrB | gyrB1Efas.iR01 | CTTGTTGCTCTCCTTCAATG (SEQ ID NO. 61) | E. faecalis |
| gyrB | gyrB1Lmon.iF03 | CCAATTTATTTGGAAGGTGAACG (SEQ ID NO. 62) | L. monocytogenes |
| gyrB | gyrB1Lmon.iR05 | GCGAATGAAATGATRTTGCTTGAGA (SEQ ID NO. 63) | L. monocytogenes |

TABLE 3

Inner Primers for Enteric Organisms in rpoB

| Preferential Target | Primer | Sequence |
|---|---|---|
| "pan-enteric" | rpoB1Ents.iF04 | CCGTAGYAAAGGCGAATCC (SEQ ID NO. 11) |
| | rpoB1Ents.iR03 | GGTWACGTCCATGTAGTCAAC (SEQ ID NO. 12) |
| E. coli | rpoB1Ecol.iF01 | ACTCCAACCTGGATGAAGA (SEQ ID NO. 64) |
| | rpoB1Ents.iR02 | ACGTCCATGTAGTCAACC (SEQ ID NO. 65) |
| K. pneumoniae | rpoB1Kpne.iF01 | GAACTCCAACCTGGATGAAAA C (SEQ ID NO. 66) |
| | rpoB1Ents.iR02 | ACGTCCATGTAGTCAACC (SEQ ID NO. 65) |
| E. cloacae/ K. oxytoca | rpoB1Eclo.iF01 | ACTC CAACCTGGATGACGA (SEQ ID NO. 67) |
| | rpoB1Ents.iR02 | ACGTCCATGTAGTCAACC (SEQ ID NO. 65) |

TABLE 4

Outer and Inner Primers for Enteric Organisms in ompA

| Target | Primer | Sequence |
|---|---|---|
| Outer primers | | |
| Enterics | ompA1Ents.oF_a | TCGCYACCCGTCTGGAATA (SEQ ID NO. 68) |
| | ompA1Ents.oR_a | CGTCTTTMGGRTCCAKGTTG (SEQ ID NO. 69) |
| Inner primers | | |
| E. coli | ompA1Ecol.iF_a | GTCTGGAATACCAGTGGACC (SEQ ID NO. 70) |
| | ompA1Ecol.iR_a | CTGATCCAGAGCAGCCT (SEQ ID NO. 71) |
| K. pneumoniae | ompA1Kpne.iF_a | CGGTCAGGAAQATGCTGC (SEQ ID NO. 72) |
| | ompA1Kpne.iR_a | GGTGAAGTGCTTGGTAGCC (SEQ ID NO. 73) |
| K. oxytoca | ompA1Koxy.iF_a | CGGTCAGGAAGATGTTGCT (SEQ ID NO. 74) |
| | ompA1Koxy.iR_a | TGACCTTCTGGTTTCAGAGT AGAT (SEQ ID NO. 75) |
| E. cloacae | ompA1Eclo.iF_a | AACATCGGCGACGGCAA (SEQ ID NO. 76) |
| | ompA1Eclo.iR_a | GCTGGAGCAACGATTGGC (SEQ ID NO. 77) |

As discussed above, while ideally each organism would be amplified exclusively by its appropriate inner second-stage primer set, cross amplification can occur. Due to expectations that organisms will show multiple, but predictable, amplification curves in a single conserved gene (see the example with K. oxytoca and H. influenzae rpoB primers in FIGS. 15A-15C described below), use of supervised learning is anticipated for the instrument 800 software, based on the pattern of amplification curves generated by the panel of conserved gene assays. For each bacterial species, clinical isolates whose identity has been confirmed by biochemical identification and, where appropriate, gene specific DNA sequencing, will form the basis for training data set for the predication software. Depending on the characteristics of the data, it is anticipated that either a nearest-neighbor algorithm or a Principle Component Analysis based ranking system will be used to generate an identity "fingerprint" for each target bacteria.

Given the complexity of a nested multiplex amplification reaction, considerable optimization may be required. In one illustrative method, outer and inner primer sets are initially tested separately in simple PCR reactions (one primer set, one template) to demonstrate whether each primer set will generate a template-dependent real-time amplification curve, with a resultant PCR product of the expected size. Illustratively, size may be demonstrated by agarose gel electrophoresis, although other methods are known in the art and are within the scope of this disclosure. Further assay optimization illustratively takes place using nested PCR and real-time detection (for example, amplified products may be detected using a fluorescent double-stranded DNA binding dye).

The fluorescence crossing point (Cp), of the nested reaction provides relative quantitation of the initial target, and can also be used as a measure of the efficiency of the PCR reactions. Comparison of Cps allows evaluation of assays run under different conditions. Both inner and outer primer sets may be optimized to generate early nested Cps, representing efficient PCR. Other parameters examined in optimization may be the Cp of the reaction when no template is added and the Cp of the reaction when human genomic DNA is used as a template. Products formed in the no-template reaction are non-specific and likely represent primer dimers. Products in the human genomic reaction that are not present in the no-template reaction represent cross-reaction with human sequences, and may interfere with specificity when the assay is performed directly from clinical specimens. In both cases, the amplification curves are false-positives, and primer sets with Cps of, illustratively, less than 32 cycles in these reactions are redesigned. While 32 cycles is chosen as the Cp cut-off point, it is understood that other crossing points could be chosen, depending on the desired specificity and sensitivity.

In the illustrative example, once assays have been optimized in singleplex format, assays may then be multiplexed and tested for limit of detection and specificity (amplification of only the intended target), with comparison to the singleplex assays. Assays may be redesigned as necessary. During multiplex optimization, assays may be moved to instrument 800, so that optimization may occur under the conditions of the final assay.

Figure 15A:
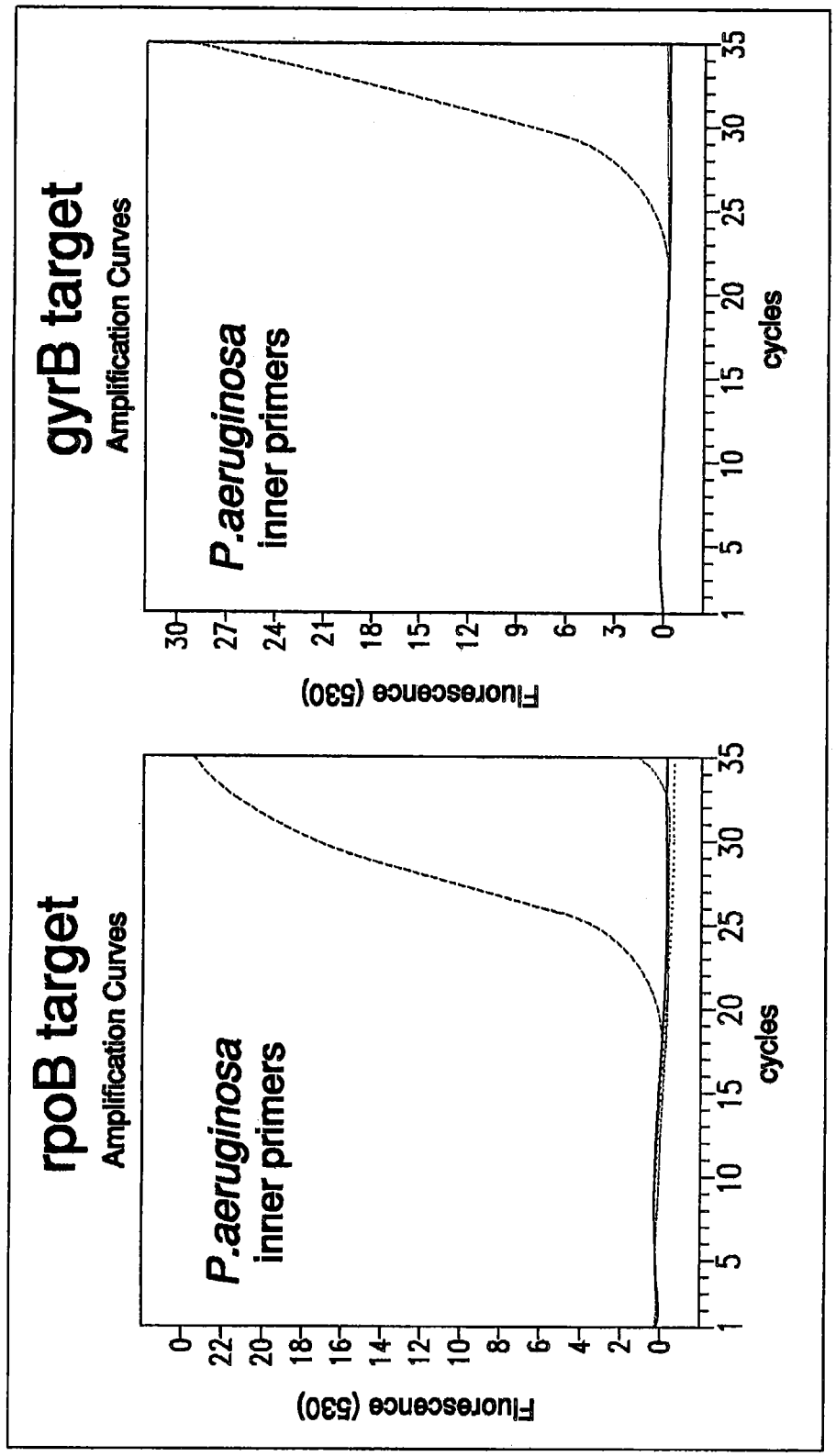
FIGS. 15A-15C show identification of Gram-negative organisms using rpoB and gyrB. Outer first-stage amplicons were generated from 5 organisms (*P. aeruginosa* (Pa, (– – – )), *E. coli* (Ec, (- - - - )), *K. pneumoniae* (Kp, –·–·– )), *K. oxytoca* (Ko, –··–·· )) and *H. influenzae* (Hi, ······) with degenerate outer primers targeting the rpoB and gyrB genes. Outer first-stage amplicons were nested into a set of organism-specific inner second-stage primers with the resulting real time amplification curves shown.
Figure 15B:
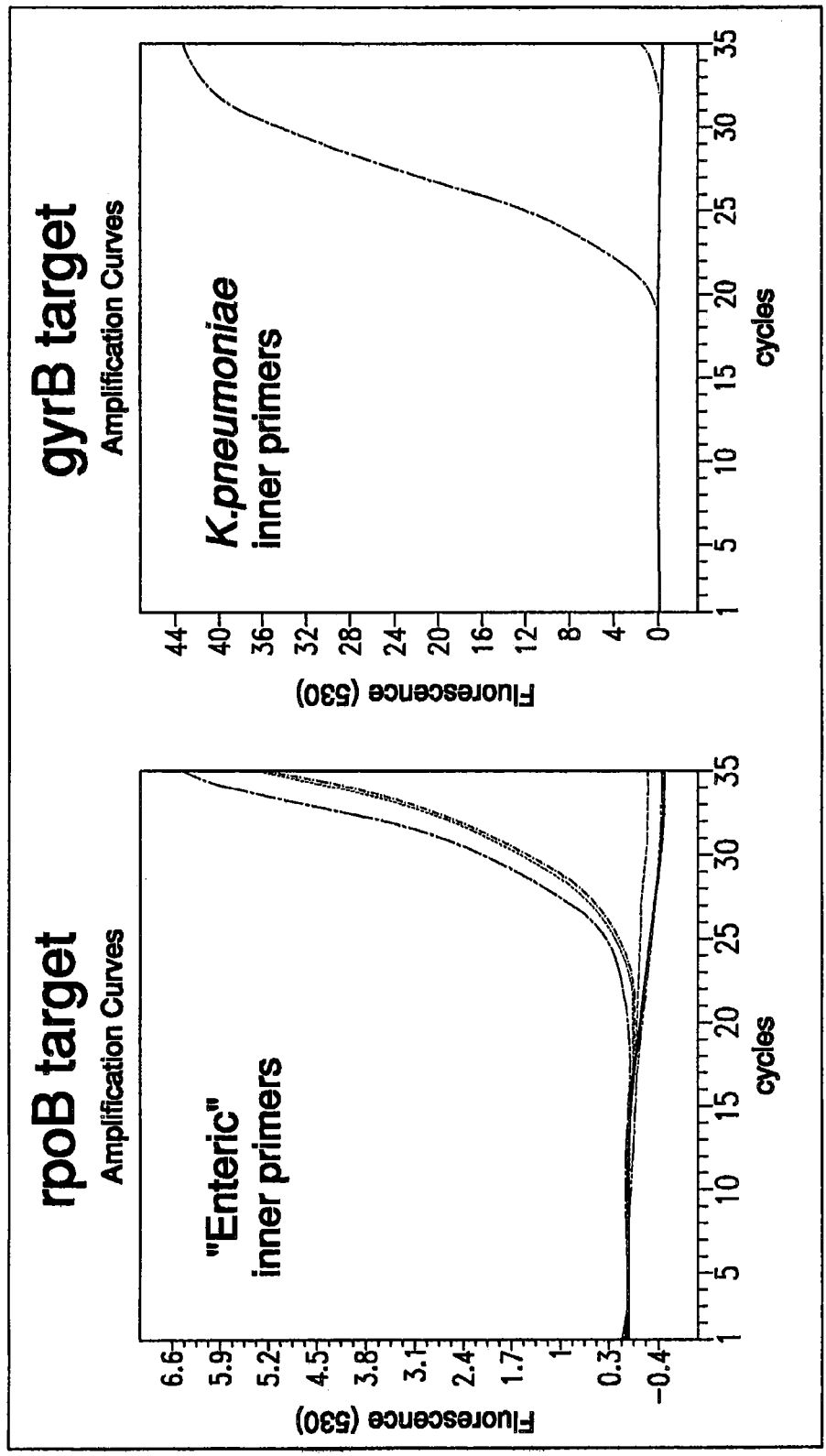
Figure 15C:
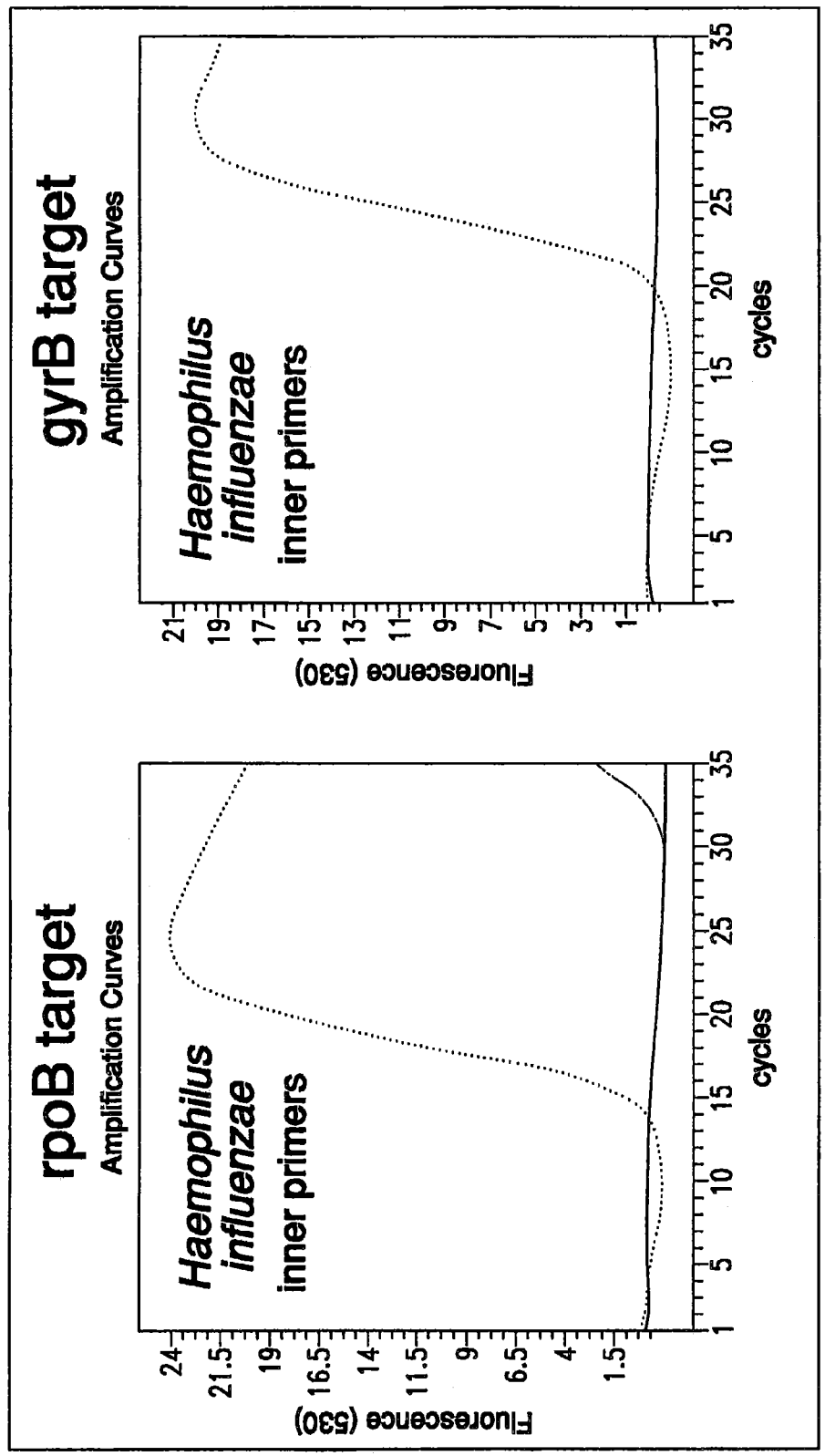
Figure 16A:
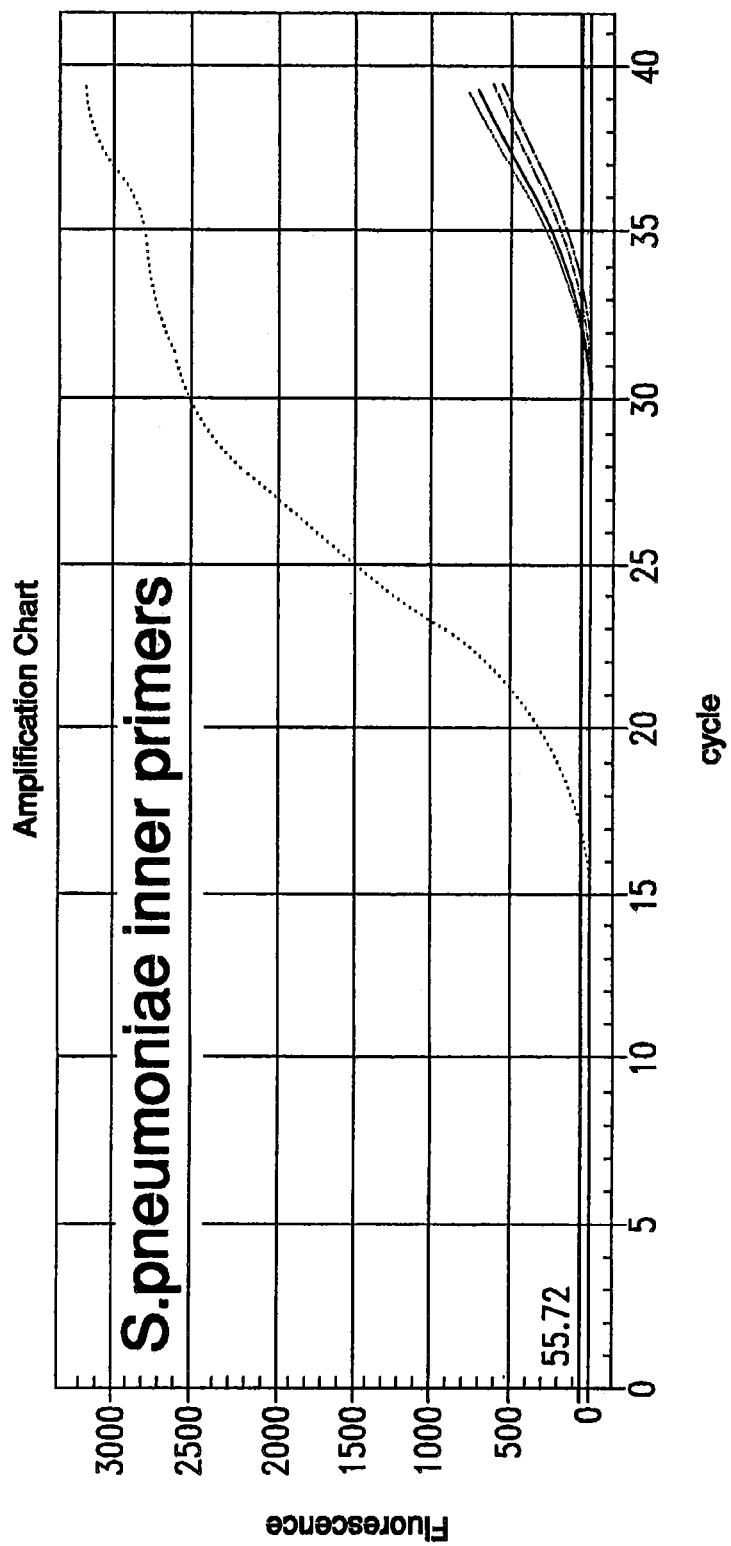
FIGS. 16A-16D show Identification of Gram-positive organisms using rpoB, with baseline subtracted amplification curves. Outer first-stage amplicons were generated from 4 organisms (*S. pneumoniae*), *S. agalactiae, S. aureus*, and *L. monocytogenes*) with degenerate outer first-stage primers targeting the rpoB gene. Outer first-stage amplicons were nested into a set of organism-specific inner primers with the resulting real time amplification curves shown. Second-stage primers specific for the rpoB gene of Sp (FIG. 16A), Sag (FIG. 16B), Sa (FIG. 16C), or Lm (FIG. 16D) have significant amplification curves only from the appropriate templates. Minor amplification curves with other templates are under investigation and likely result from the formation of "primer dimers" (especially in the case of the *S. aureus* primers) or possibly cross-amplification.
Figure 16B:
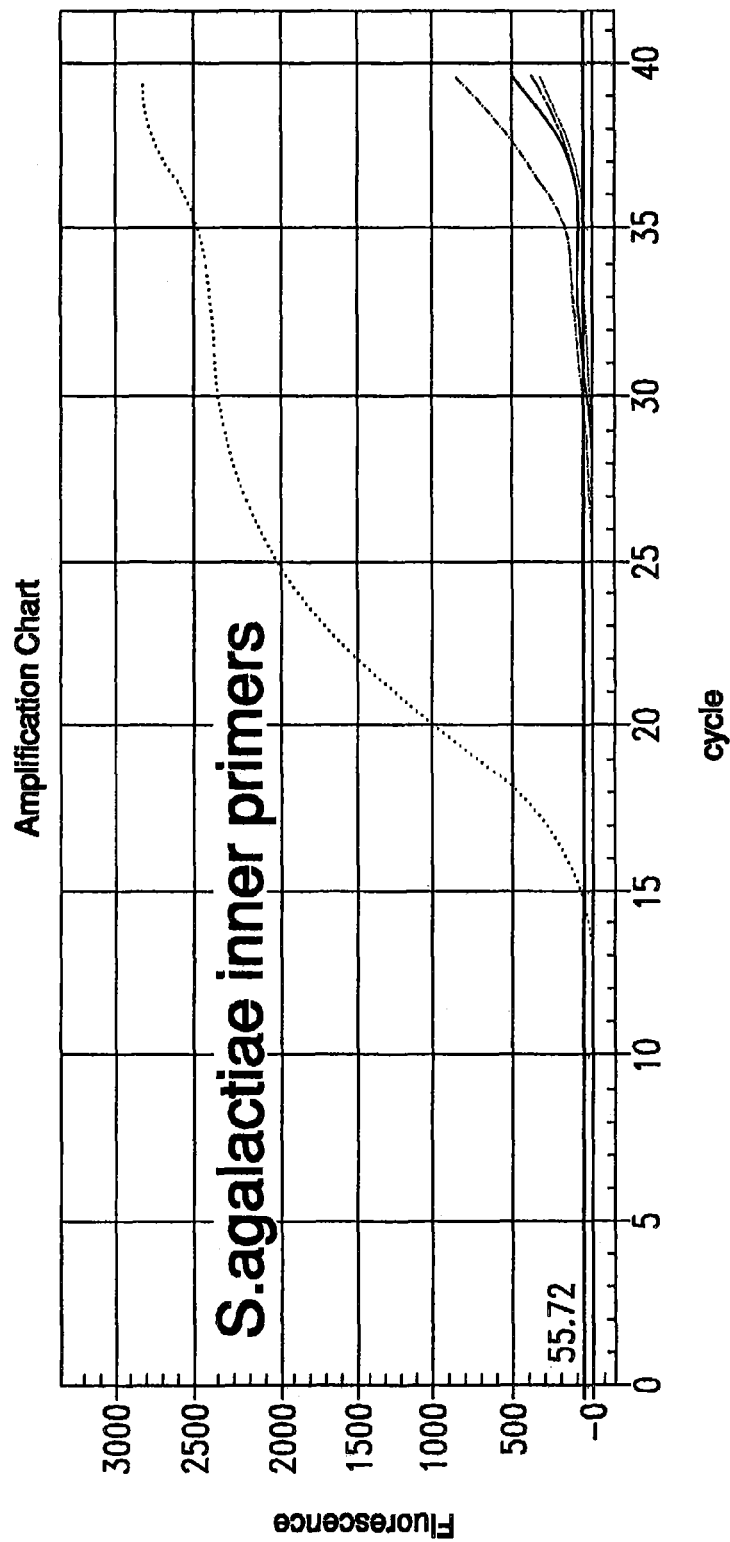
Figure 16C:
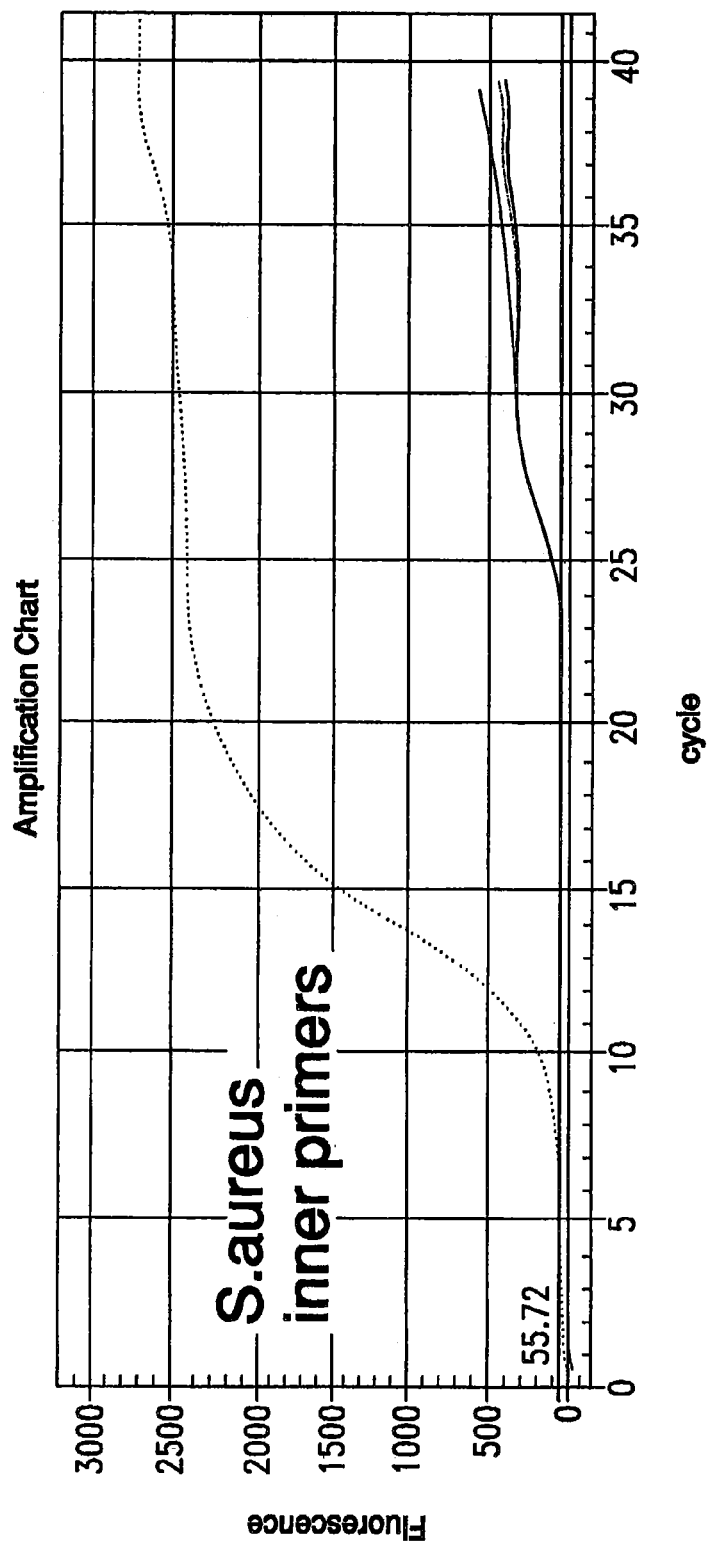
Figure 16D:
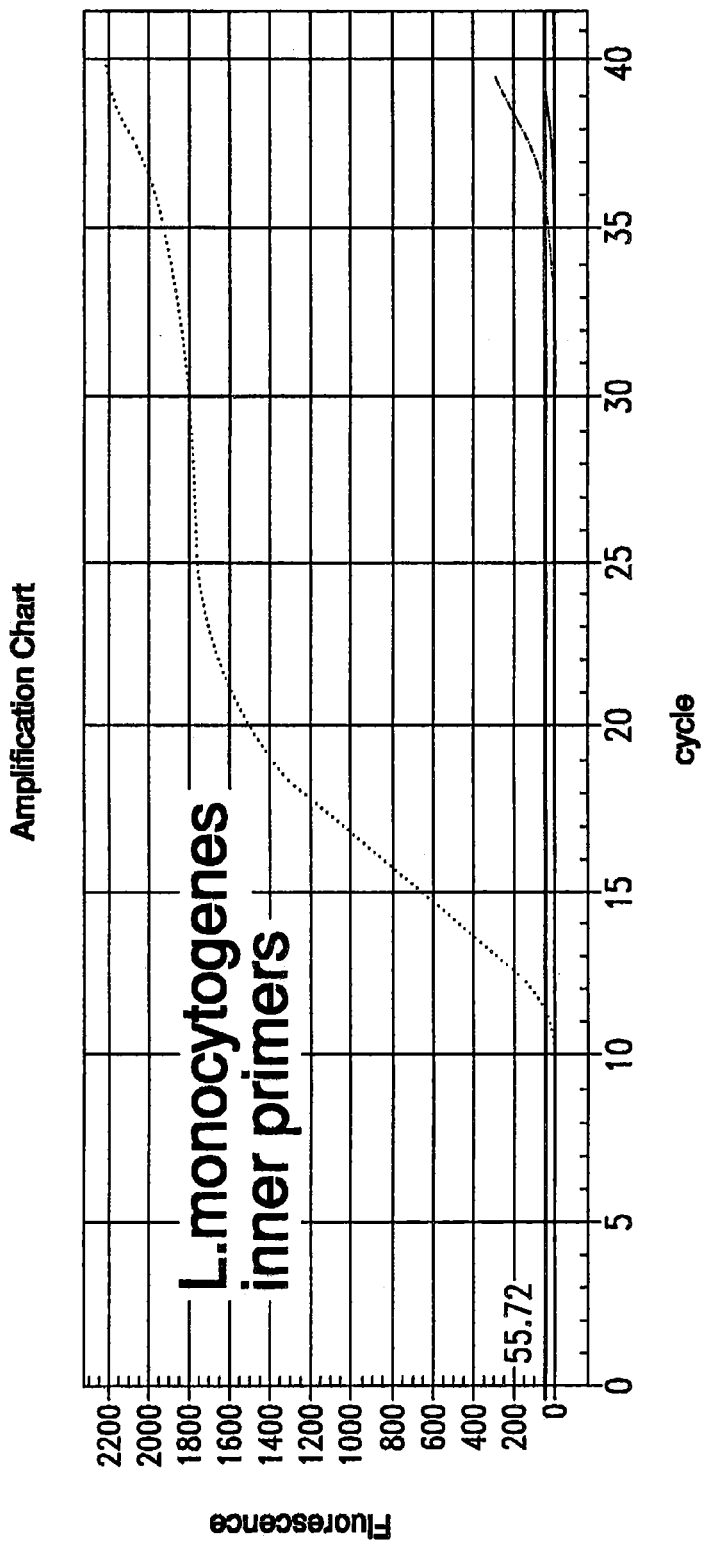
Figure 17A:
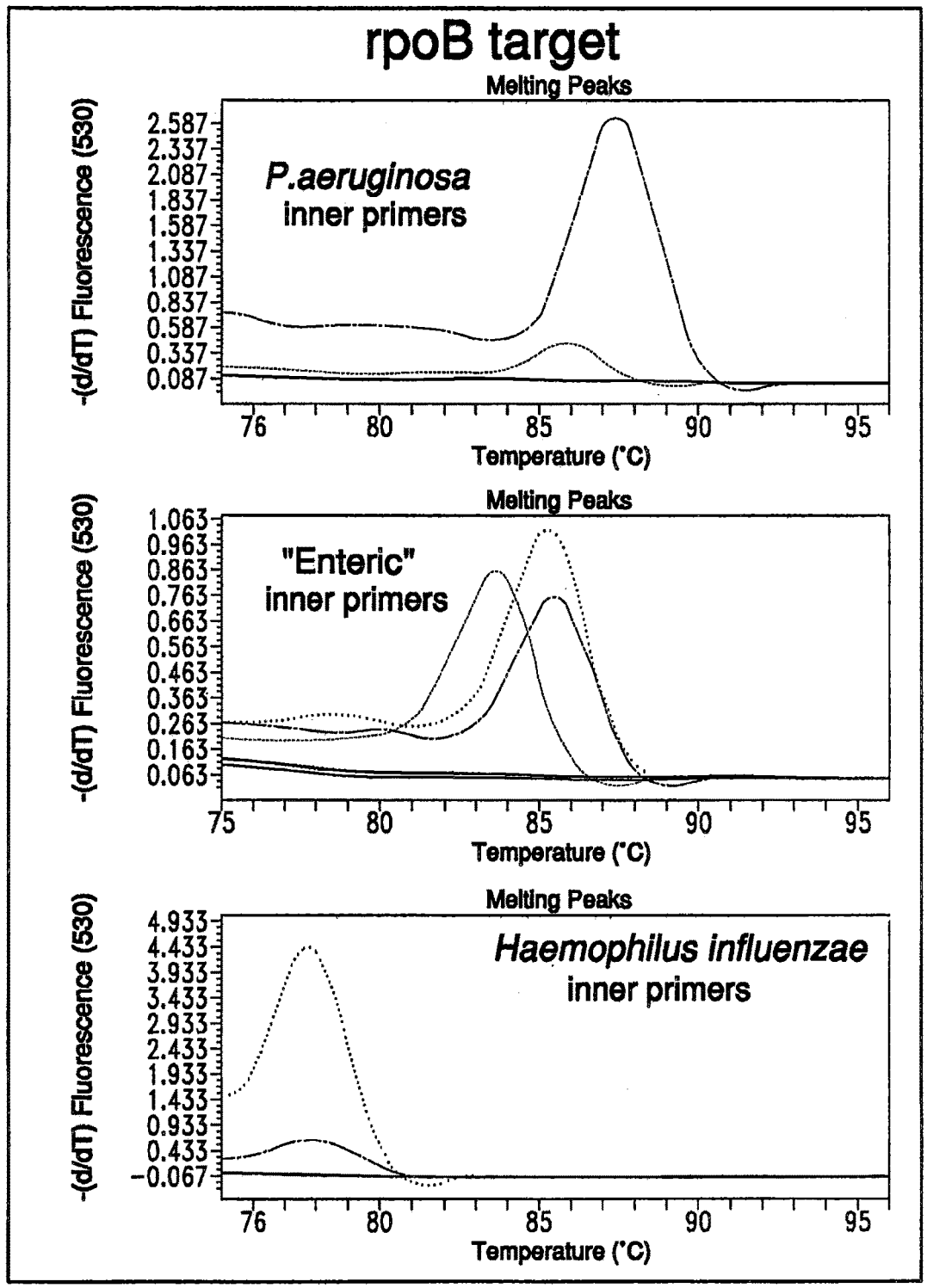
FIGS. 17A and 17B show melting profiles of amplicons from the amplification reactions shown in FIGS. 15A and 15B. The melting profile of each amplicon was generated using the dye LCGreen® Plus. Amplicons melted with characteristic Tms that ranged from 78° C. for *H. influenzae* to 90° C. for *P. aeruginosa*.
Figure 17B:
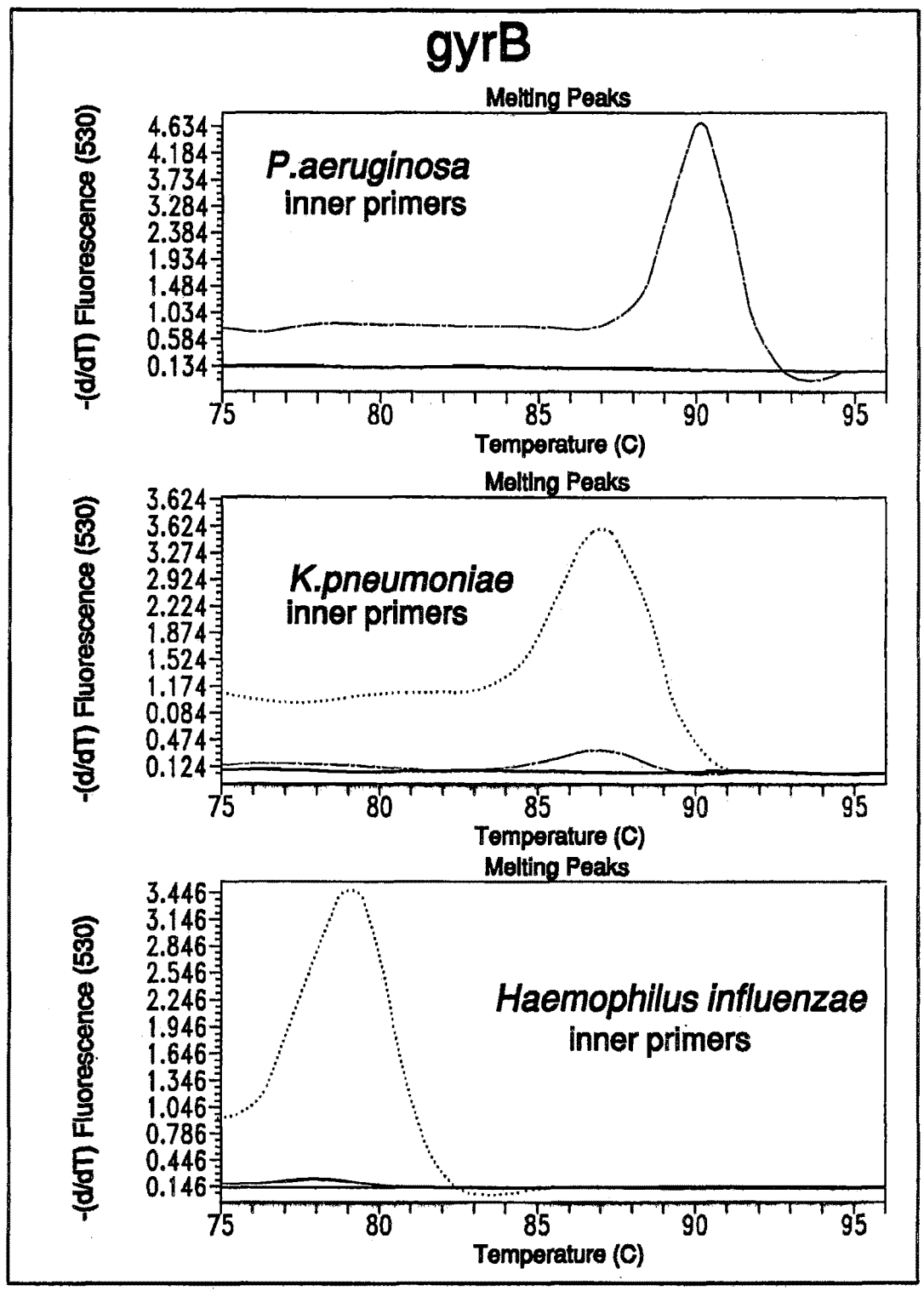

Two sets of experiments demonstrating the illustrative bacterial identification strategy are shown. FIGS. 15A-15C show an experiment in which both rpoB and gyrB are used for identification and differentiation of Gram-negative organisms. Bacteria from different phyla have been included to help display the broad range of the outer first-stage primers, and because they are important antibiotic-resistant Gram-negative pathogens that could be targeted in an illustrative assay according to the methods discussed herein. In the experiment shown in FIGS. 15A-15C, DNA was extracted from clinical isolates of the selected organisms. Total bacterial nucleic acid was amplified in a multiplex outer first-stage PCR reaction containing primer sets targeting both the rpoB and gyrB genes of Gram-negative organisms (one degenerate primer pair per gene). All first-stage amplicons were then nested into all inner second-stage PCR reactions each containing a primer set specific for a particular organism and amplified in the presence of LC Green® Plus, although other detection means may be used, as described above. As shown in FIGS. 15A-15C, although first-stage amplicons for each bacterium are tested with all inner second-stage primer sets, the only inner primer sets showing significant amplification are those directed at the target organism. This demonstrates the specificity of the inner second-stage assay. FIGS. 16A-16D show an experiment looking at the rpoB gene, in this case with Gram-positive targets. As was seen in FIGS. 15A-C, the only inner second-stage primer set showing significant amplification is that directed at the target organism. FIGS. 17A and 17B show amplicon melting profiles for the second-stage amplicons generated in the experiment shown in FIGS. 15A-15C. As can be seen in FIGS. 17A and 17B, the amplicons melt with characteristic profiles, which could be used for further specificity in organism identification. Subsequently, second stage primers have been developed for S. epidermidis, K. oxytoca, and E. faecalis for use with the same first-stage primers.

Figure 18A:
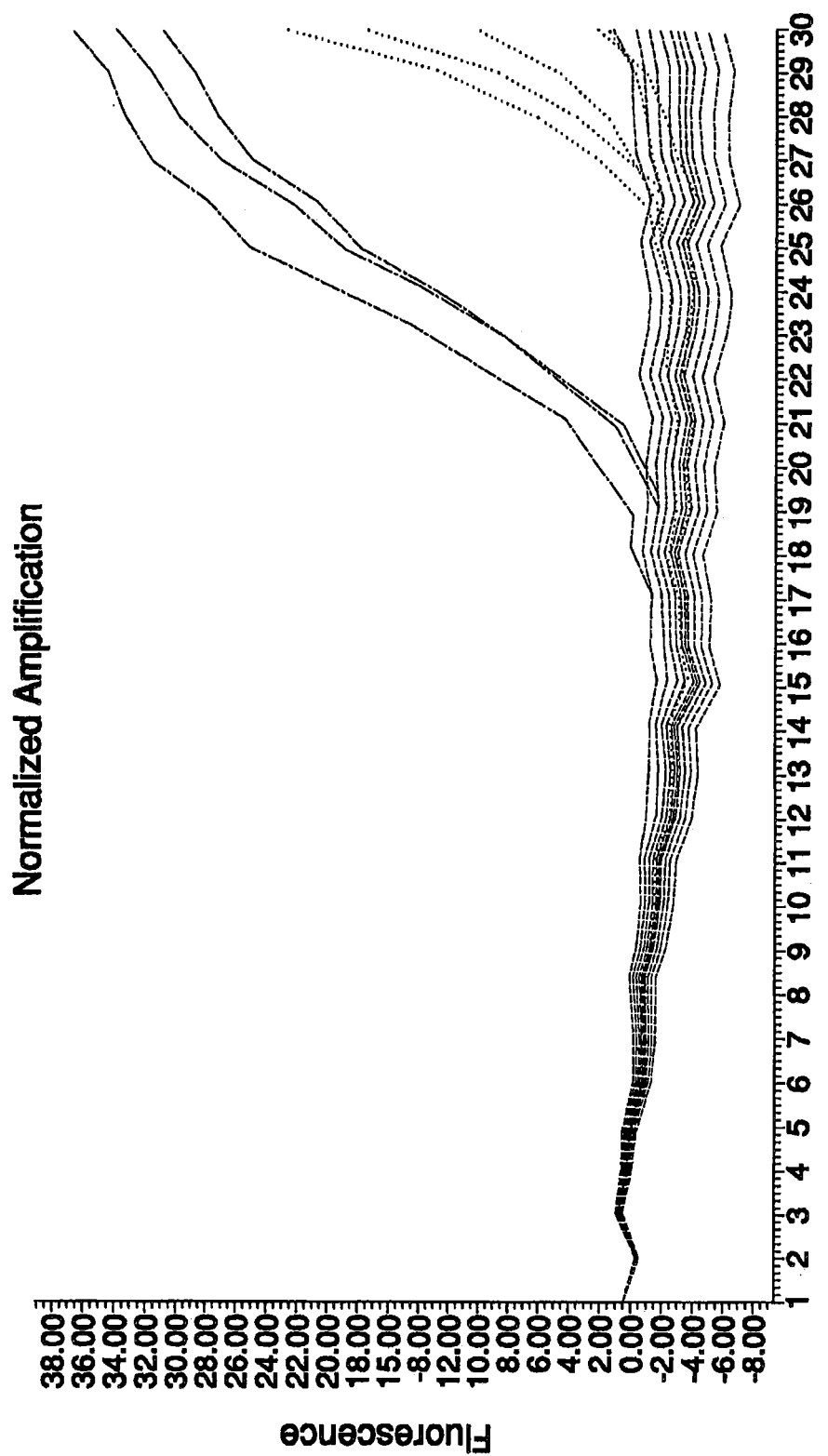
FIGS. 18A and 18B show results for *N. meningitidis*.
Figure 18B:
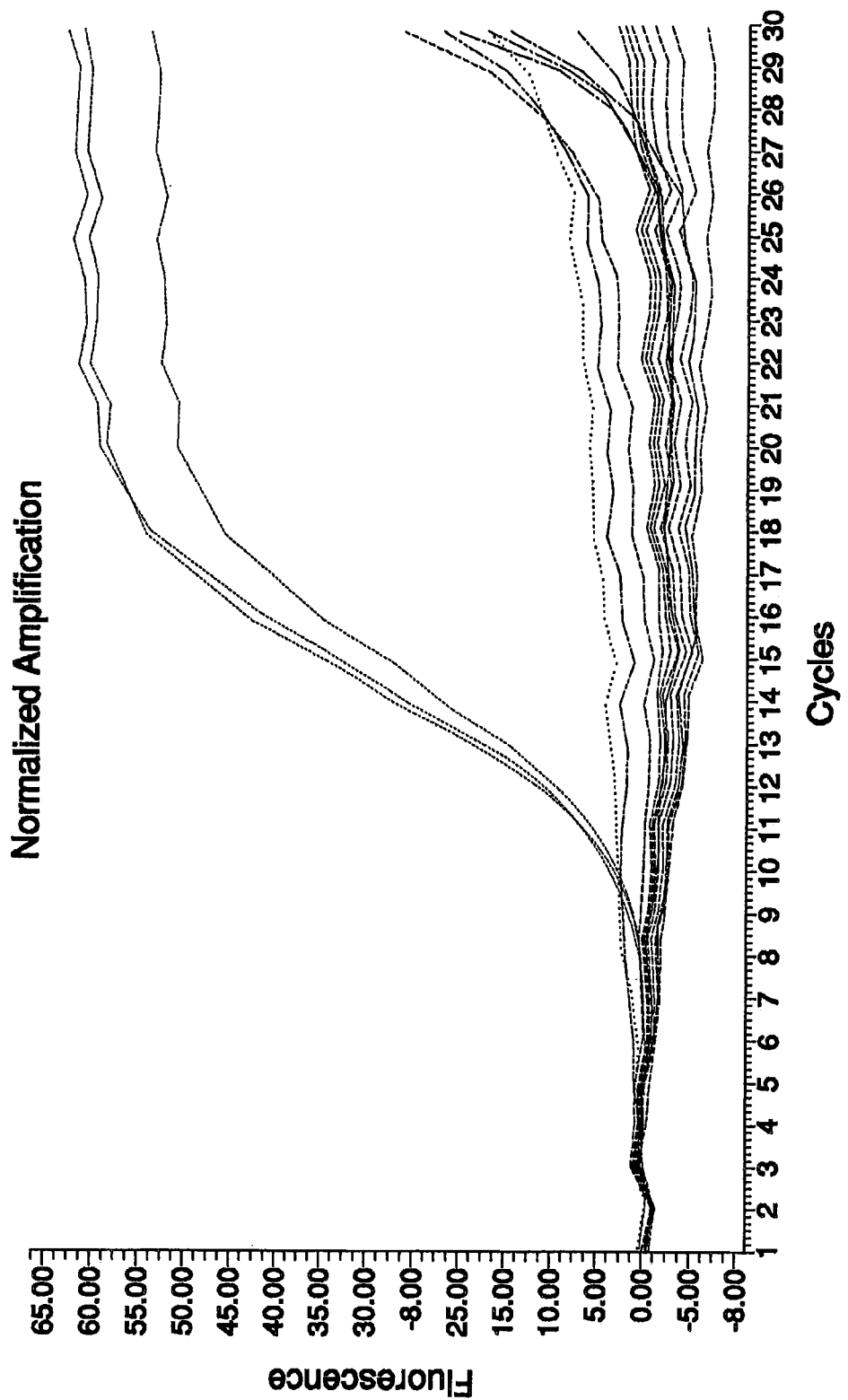

The above examples were done as individual reactions, for the purposes of optimizing. FIGS. 18a-b show amplification with a first-stage amplification and second-stage amplification done in an instrument 800. Inner second-stage primers were spotted in triplicate in second-stage 581. The replicates were spotted in locations remote from each other, to minimize positional effects. The results shown in FIG. 18A are for the *N. meningitidis* gyrB assay. The three amplification curves with the lowest Cp (about 18-20) are the *neisseria* amplification curves, while those coming up later (Cp>25) show primer-dimers or other non-specific amplification. FIG. 18B shows the results for the *N. meningitidis* rpoB assay, confirming the results from the gyrB gene, with even greater separation between the target amplification and the non-specific amplification. In addition to Cp, the results may be confirmed using melting curve analysis. Similar results have been obtained with other targets. Clinical samples have been run on this panel, resulting in 0-4 positive targets per sample.

It is understood that while the above examples are used for identifying bacterial species, the method could be applicable to identification of unknown bacteria. Illustratively, second stage inner primers could be designed more generally, and spread throughout the "sequence space" of the variable inner region. Bacterial identification would then be based on the Cp "fingerprint" across the second stage PCR array. The bacterial training set described above would be used to determine fingerprints for known bacterial species, and additional species/novel fingerprints encountered over time could be added to the data.

Additionally, while the above examples focus on identifying bacterial species, a similar method could be used to identify antibiotic resistance, with or without species identification. Many antibiotic resistance genes are found on plasmids, and for treatment purposes, the presence or absence of the gene or gene mutation may be more important than identification of the pathogen. As an illustrative example, one could test for one or more of the TEM, SHV, and CTX-M β-lactamase genes found on plasmids in Gram-negative enteric pathogens. In this example, outer primers would target conserved portions of the plasmid; inner primers could also target conserved regions when the presence or absence of the plasmid confers resistance (e.g. ampicillin resistance), or alternatively could target regions in which mutations conferring different resistance properties (e.g. the extended-spectrum β-lactamase phenotype) are found. If point mutations lead to a change in the resistance pattern, probes can be included in the second stage reaction to identify the mutation, illustratively by probe melting. The probes may be labeled, or the second-stage reaction may include a dsDNA binding dye, illustratively a saturation dye (see, e.g., U.S. patent application Ser. No. 11/485,851, herein incorporated by reference). Table 5 shows illustrative probes targeting several mutations in the TEM β-lactamase gene.

TABLE 5

| Probe | | WT codon | Mutant codon |
|---|---|---|---|
| TEM (104) wt | ACTTGGTTgAGTACTCACCAGTC ACAGAA (SEQ ID NO. 78 | GAG | |
| TEM (104) EK | ACTTGGTTaAGTACTCACCAGTC ACAGAA (SEQ ID NO. 79) | GAG | aAG |

TABLE 5-continued

| Probe | | WT codon | Mutant codon |
|---|---|---|---|
| TEM (164) wt | CCTTGATcGTTGGGAACCGGAGC TGAAT (SEQ ID NO. 80) | CGT | |
| TEM (164) RS | CCTTGATaGTTGGGAACCGGAGC TGAAT (SEQ ID NO. 81) | CGT | aGT |

Further, it is understood that the methods described herein could be used for the identification of other, non-bacterial species. As described above, the outer first-stage primers may be targeted to generally conserved regions of target genes, while the inner section-stage primers would be targeted to sequences specific for the species or genus. In one example, the methods described herein could be applied to fungal identification. Such an application of the present invention could significantly reduce the time to diagnosis, as sporulation, which can take several days to several weeks, is currently used to identify a fungal species. In some cases, a fungus may not sporulate at all in the clinical laboratory, and would only be identifiable by molecular methods. If four conserved genes are required for the outer first-stage amplification, twenty-five or more inner second-stage targets may be tested per gene, assuming approximately 100 second-stage wells 582. Other non-limiting potential combinations are as follows:

8 genes×12 inner primers=96 reactions 7 genes×14 inner primers=98 reactions 6 genes×16 inner primers=96 reactions 5 genes×20 inner primers=100 reactions It is understood that these combinations are illustrative only, and that other combinations are possible. For example, if there are more second stage wells 582 in high density array 581, then additional genes and/or more inner primer sets may be used. Alternatively, if the first-stage amplicon is large, it may be desirable to amplify several regions of the first-stage amplicon, illustratively for better identification of strains of the same organism. If desired, amplicon melting temperatures and/or probes may be used for further identification or for confirmation of results. Illustratively, the second-stage amplicons include sufficient information for identifying at least 50% of the species or strains, and more illustratively 90% of the species or strains.

EXAMPLE 5: RAPID EPIDEMIOLOGIC TYPING OF BACTERIA

In this example, high-order multiplex PCR testing for identification and characterization of bacteria, illustratively MRSA is described. While reference is made to bacteria generally and MRSA specifically, it is understood that these examples are illustrative only, and the methods described herein have other applications. In the course of developing the nmPCR assays for the bacterial identification panel described above, a protocol has been established for designing the primer sets, testing them, revising as needed and testing in singleplex and multiplex formats.

Currently, it is anticipated that 68 primers may be used for the identification and characterization of MRSA isolates in the illustrative example (Table 6).

TABLE 6

Proposed Targets for the MRSA panel

| Application | Gene | Full Name or function | #Outer primers in multiplex |
| --- | --- | --- | --- |
| Identification of | rpoB | RNA polymerase beta subunit | 2 |
| S. aureus, | gyrB | DNA gyrase subunit b | 2 |
| Detection of coagulase- | rpoB | RNA polymerase beta subunit | 2 |
| negative staph | gyrB | DNA gyrase subunit b | 2 |
| Methicillin resistance | mecA | Encodes PBP2A | 2 |
|  | mecA/orfX | links mecA to S. aureus | 2 |
| Other drug | ermA, ermB, | Macrolide resistance | 6 |
| susceptibility | ermC | (inducible clinda resistance) |  |
|  | msrA | Macrolide resistance | 2 |
|  |  | (clinda sensitive phenotype) |  |
|  | dfrA | Trimethoprim-sulfa resistance | 2 |
|  | tetK, tetM | Tetracycline resistance | 4 |
|  | mupR | Mupirocin resistance | 2 |
|  | vanA, vanB, vanZ | Vancomycin resistance | 6 |
| PVL | lukF, lukS | Panton-Valentine leukocidin | 2 |
| SCCmec typing |  | I-J1 region | 2 |
|  |  | V-ccr complex | 2 |
|  |  | III-J3 region | 2 |
|  |  | V-J1 region | 2 |
|  |  | I, II, IV, VI-J3 region | 2 |
|  |  | II, IV-ccr complex | 2 |
|  |  | II-J1 region | 2 |
|  |  | III-J1 region | 2 |
|  |  | II, III-mec complex | 2 |
| MLST | arcC | Carbamate kinase | 2 |
|  | aroE | Shikimate dehydrogenase | 2 |
|  | glpF | Glycerol kinase | 2 |
|  | gmk | Guanylate kinase | 2 |
|  | pta | Phosphateacetyl transferase | 2 |
|  | tpi | Triosephosphate isomerase | 2 |
|  | yqiL | Acetyle coenzyme A acetyltransferase | 2 |

Total Outer Primers: 68

For initial design and testing, cultured bacterial isolates of known genotype will be used as targets. To prepare the assay for clinical use, limit of detection studies will be performed, as well testing of samples with other organisms to demonstrate sufficient sensitivity and specificity for direct-from-specimen testing. Anticipated clinical specimen types include sputum, a nasal swab, a nasal aspirate, a tracheal aspirate, another respiratory specimen, a wound culture, and a sterile site culture (illustratively blood, spinal fluid, joint fluid, pleural fluid, etc.), although other specimen types may be used.

In the illustrative S. aureus-specific testing proposed herein, outer primers will be designed to be specific for S. aureus, decreasing the possibility of amplifying other bacteria. In addition, assays for S. epidermidis and other coagulase-negative staphylococci ("CONS") may be included, to detect these as potential contributors to mecA amplification. mecA identification by PCR is well-established (23-26), and nmPCR assays may be based on published primers or may be designed anew. Published assays target various regions of mecA, with a range of amplicon sizes. It is understood, however, that certain assays may need to be re-designed, particularly if pairs of primers interfere during first-stage PCR or are not compatible with the amplification conditions. Illustratively, assays will be chosen that best fit with the amplification conditions of instrument 800.

Assays have been published and at least one has been FDA approved for the direct identification of MRSA from clinical specimens, using an S. aureus-specific sequence from orfX, an open reading frame of unknown function at the chromosomal right junction where SCCmec integrates into the S. aureus genome (23, 24). Sequences within this gene illustratively may be used for the reverse PCR primer, as mecA is reliably linked to the S. aureus-specific orfX sequence. Thus, by providing one primer in the mecA sequence and the other primer in the orfX sequence, misclassification due to the presence of mecA-containing CONS within a sample may be avoided. Since the amplicons illustratively will be S. aureus-specific, nesting the second-stage primers is optional. However, nesting may be desired, particularly when generating shorter second-stage amplicons for the melting analysis discussed below.

It is known that S. aureus contains numerous virulence factors that enhance its pathogenicity. Many virulence factors are present in most isolates. However, there are some factors for which an association with pathogenicity is assumed, but not definitive (27, 28). A specific example is the Panton-Valentine leukocidin, present in the most virulent CA-MRSA strains and thought to lead to the highly invasive nature of this pathogen (27, 29, 30). Routine and unbiased testing could establish the role of PVL in clinical disease, and thus PVL testing may be included in the illustrative assay. The initial illustrative design will be based on well-characterized assays targeting the lukS-PV and lukF-PV genes (31, 32).

In addition, nmPCR assays may be included for the detection of known genes conferring resistance to anti-staphylococcal agents such as tetracyclines, macrolides and lincosamides (see Table 6). vanA, vanB and vanZ are targets for detecting vancomycin resistance (VRSA) (33, 34). An important advantage of the instrument 800 is its flexibility; new tests can be added to the first-stage multiplex assay, and inner primers may be modified as new resistance genes emerge. It is anticipated that the susceptibility portion of the assay will evolve as new mechanisms are detected, to include resistance determinants for VISA (vancomycin intermediate S. aureus), as well as newer agents such as linezolid and daptomycin.

SCCmec typing is integral to MRSA clone identification (35, 36). There are currently 5 major SCCmec types described, as defined by mec complex class and ccr allotype; SCCmec subtypes are defined by variations in the J region (J1-J3) (35, 37). A number of PCR-based SCCmec typing methods have been described, including multiplex strategies which can differentiate the major types (38-41). A widely used multiplex is that of Oliveira and Lancaster (40) herein incorporated by reference, recently updated to include assays for SCCmec types IV and V (42). It is expected that a version of this assay will be adapted for instrument 800. This illustrative multiplex, using 20 primers to amplify 10 regions, identifies SCCmec type based on the presence of specific bands on a gel, corresponding to the presence or absence of amplification within a specific well 582. The genetic organization of SCCmec and similarities between the 5 types may pose difficulties for the design of nested primers. Accordingly, sequence alignments will be used to determine appropriate unique sites either inside or outside the published primers. Additionally, the ccr region is not interrogated in this illustrative multiplex. Primers for this region may need to be added to define novel SCCmec types. Other multiplex methods have been published (38-41), including a recent paper describing a multiplex SCCmec PCR, using only eight primers to amplify and distinguish the five major SCCmec types (38). These assays could be substituted or added in a later embodiment.

Current culture-based bacterial detection strategies take several days, and do not provide data regarding the clonality of isolates. Identifying clonality is an important step in outbreak identification and tracking. The ability to conduct rapid diagnostic testing—with the power to provide simultaneous typing of bacterial clones—would significantly improve patient care and infection control, and improve our understanding of both hospital and community risks. Common methods for outbreak detection and clone-typing of bacterial isolates are pulsed-field gel electrophoresis (PFGE) and multi-locus sequence typing (MLST). As currently performed, however, both PFGE and MLST are costly, time-consuming, and available primarily for research purposes. Both methods are primarily performed when an outbreak is already suspected, and essentially provide confirmatory data, rather than true detection. Development of the assays described herein, which illustratively use high-resolution melting, along with heteroduplex analysis, would allow rapid, modest cost, real-time isolate typing that could become standard for every bacterial isolate.

Conventional MLST requires sequencing of multiple amplicons (43). Even with automation, this introduces expense, delay and complexity. Second-stage amplification, in conjunction with high-resolution melting, as described in U.S. Patent Publication Nos. 2005-0233335 and 2006-0019253, herein incorporated by reference, along with heteroduplex analysis (described below) may be used for typing strains, illustratively of S. aureus isolates. A recent paper described a method for MLST analysis of S. aureus using a microchip, supports the feasibility of performing such typing without sequencing (21).

Figure 21B:
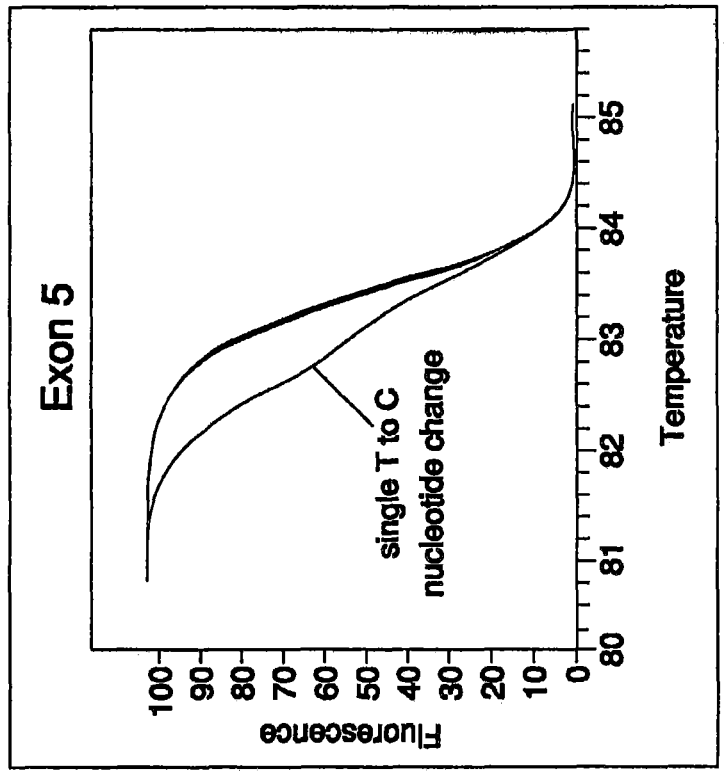
FIGS. 21A and 21B show superimposed melting curves from 13 patients was analyzed for heterozygous changes in the MCAD gene using the LightScanner® (Idaho Technology). Results at two exons are shown to demonstrate how single base-pair changes are analyzed by heteroduplex melting.
Figure 21A:
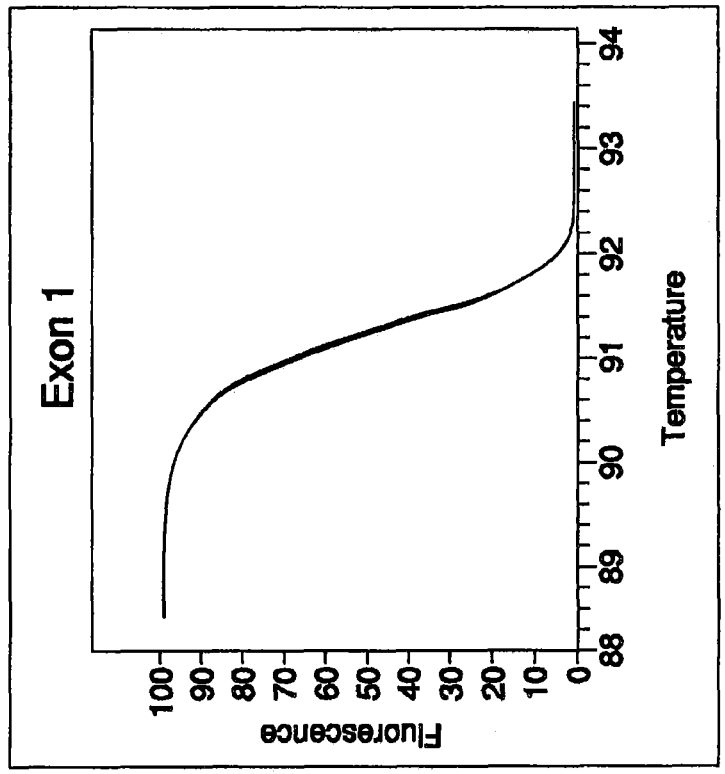

Melting curve analysis may be used to characterize products that are amplified. A double-stranded DNA binding dye, added to the PCR reaction to monitor amplification, can also be used to determine the characteristic temperature at which 50% of the DNA product denatures (the amplicon "Tm"). High-resolution melting, as described in U.S. Patent Publication Nos. 2005-0233335 and 2006-0019253, is extremely sensitive to changes in nucleotide sequence, and allows mutation scanning and genotyping (44, 45). Properties of the specialized dye used in high resolution melting, such as LC Green® Plus (Idaho Technology), instrumentation, and software allow even single base-pair changes in PCR products to be detected by changes in the shape of the melting curve (46). In a diploid genome, homozygous changes in nucleotide composition can be difficult to detect in a PCR amplicon, even using high-resolution melting. Simpler to identify are heterozygous changes, in which DNA "heteroduplexes" are formed during melting (47). In such analysis, amplicons from the two different alleles are allowed to pair, with mismatches at the heterogeneous sites. This leads to destabilization of the duplex, and an early melt transition when compared to controls. This method is used frequently in human genetics for detection of single nucleotide polymorphisms (SNPs) (44, 47, 48). An example of such melting curve analysis is shown in FIGS. 21A and 21B.

Figure 22:
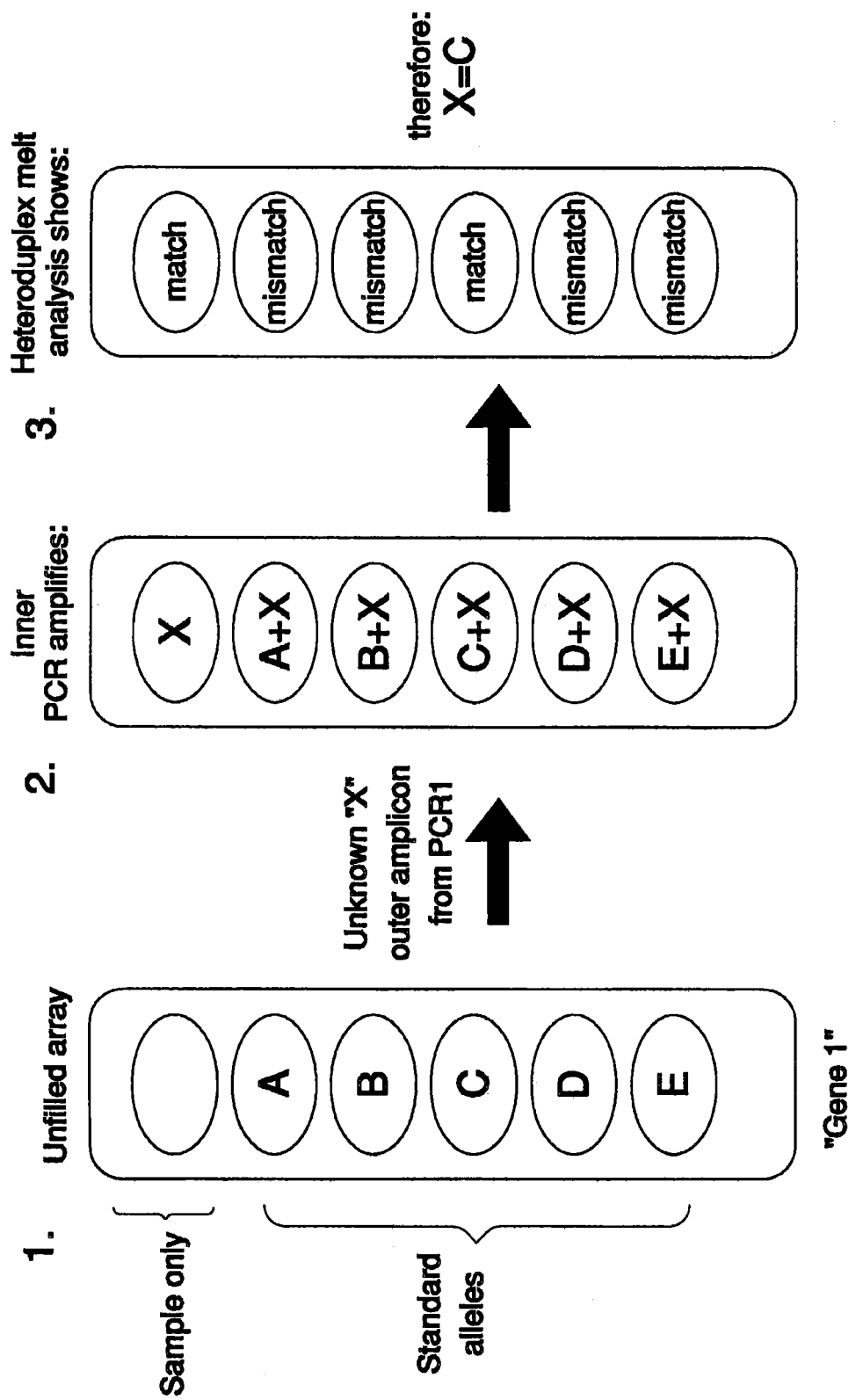
FIG. 22 is a simplified schematic of how the second-stage for strain typing. The top well does not have a standard so that the unknown is represented alone. In the second panel, the outer amplicon from unknown "X" enters the array and is distributed to all wells. In the uppermost well, X alone is amplified; in the lower wells, X and a standard allele are amplified together. After PCR, the amplicons undergo high-resolution melt analysis, with curves normalized to the melting curve of X. Where X and the standard allele are different, heteroduplexes form, and the melt does not match that of X. Where X and the standard are the same, the melting curves match, and the allele is identified.

For the detection of changes in a haploid bacterial genome, heteroduplex analysis can also be used. Illustratively, a control or standard DNA of known sequence is added to the PCR reaction prior to amplification. Both control and unknown samples are amplified and analyzed by melt. Any changes in the unknown sample relative to the control are detectable by the formation of heteroduplexes, and the presence of early-melting amplicons. In the illustrative embodiment, high resolution melting and heteroduplex analysis is used for typing analysis of S. aureus. Amplification of seven published MLST genes (arcc, aroe, glpf, gmk, pta, tpi, yquil) will be performed by nmPCR, illustratively with the published primers (49) used in the outer reaction, and two sets of inner primers will span the amplicon so that all potential polymorphic sites are interrogated. A schematic of the inner PCR is shown in FIG. 22. Standards, consisting of known sequenced alleles for each gene (up to 33 alleles/per gene have been described to date), will be added to single wells 582 with appropriate primers. "Sample-only" wells (no standard) will be present to characterize the unknown sample. During PCR, sample-only wells will amplify only the DNA of the unknown, while the wells with standards will amplify both. Where the unknown differs from the standard allele, heteroduplex DNA will be formed, and melt differences will be detectable when compared to the sample-only well. Where the unknown and the standard allele are the same the melts will be identical, thus identifying the allele. It is understood that strains having differences from all alleles represented in the array will be identified only as "different" and may require sequencing to define.

Figure 23A:
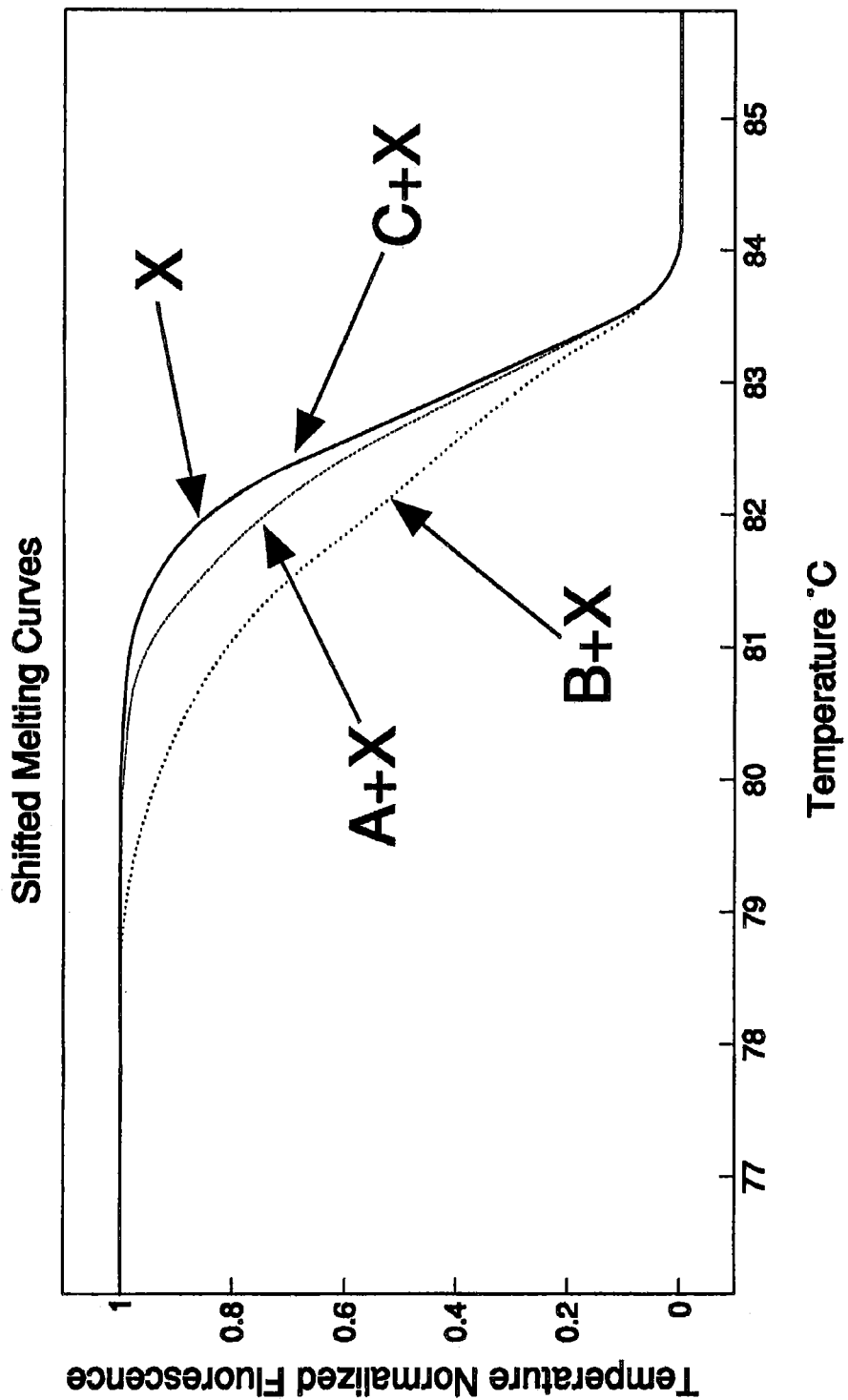
FIGS. 23A and 23B show results for four *S. aureus* clinical isolates (3 MRSA and 1 MSSA), identified by melt to represent 3 different alleles of aroE, which were used to demonstrate the feasibility of using high resolution melting and heteroduplex analysis for MLST. One MRSA isolate was designated as the unknown (X). Two other MRSA isolates (A and C) and one MSSA isolate (B) represent the "standard" alleles.
Figure 23B:
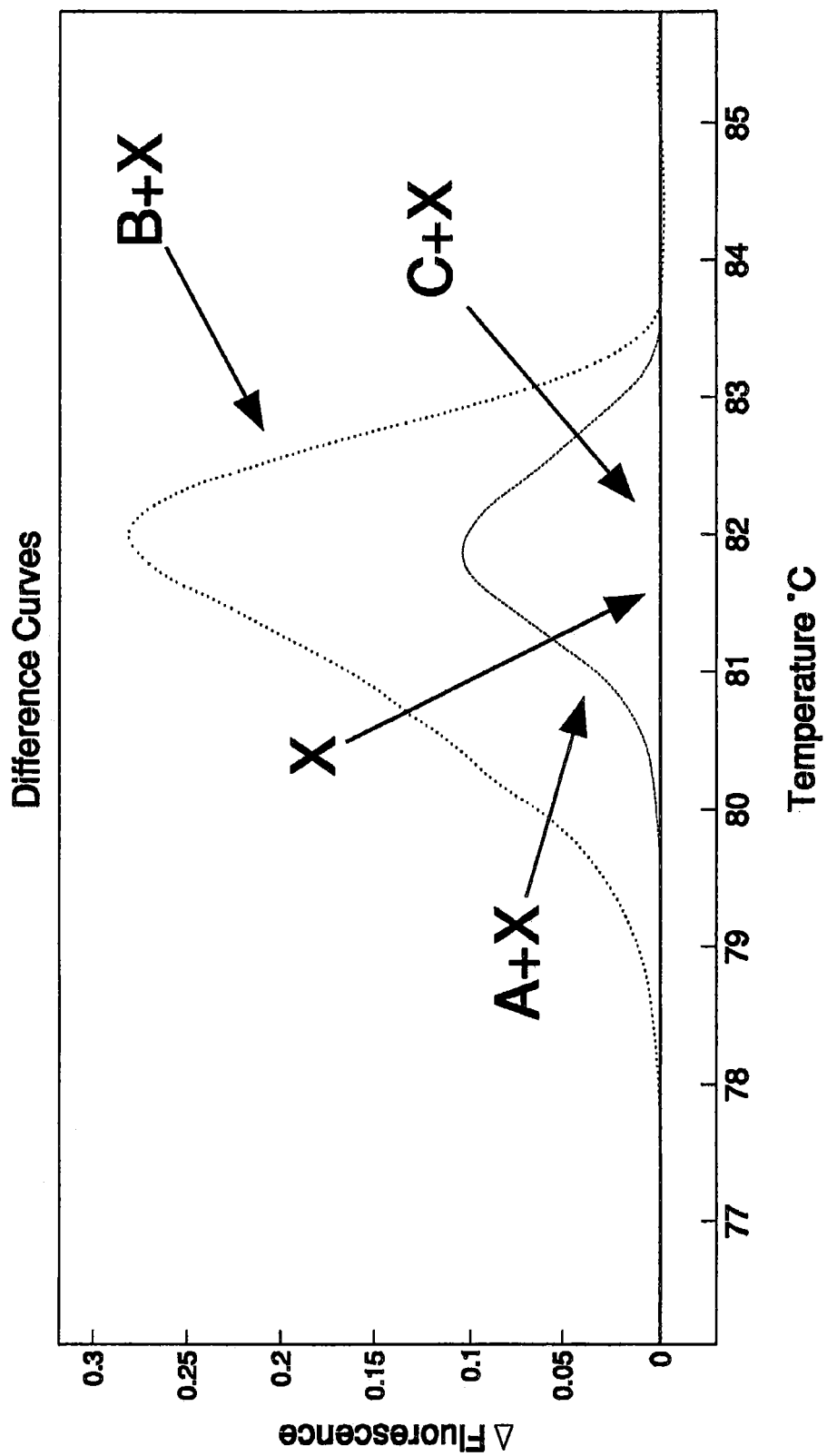

The feasibility of this approach was tested using clinical isolates with data shown in FIGS. 23A and 23B. FIG. 22 shows a simplified schematic of how the second-stage amplification could be used for this typing analysis. Only six wells 582 are shown. The first panel shows a single MLST gene ("Gene 1") that has 5 "standard" alleles (A-E) represented. The top well does not have a standard so that the unknown will be amplified and melted alone. In the second panel, the outer amplicon from unknown "X" enters the array and is distributed to all wells. In the uppermost well, X alone is amplified; in each of the lower wells, X and one of the standard alleles are amplified together. After PCR, the amplicons undergo high-resolution melt analysis, illustratively with curves normalized to the melting curve of X. Where X and the standard allele are different, heteroduplexes form, and the melt does not match that of X. Where X and the standard are the same, the melting curves match, and the allele is identified. In the example shown here, the curves for X and for C have been found to be the same, thus X=C. Preliminary data supporting this approach is shown in FIGS. 23A and 23B. It is expected that to test every target allele for *S. aureus* in this manner, 162 or more wells 582 will be needed. It is understood that this method is particularly well suited for targets that are haploid, as identity is determined by matching melting curves. While this method can be applied to diploid or polyploid targets, the analysis would be more complex.

The above example for *S. aureus* strain typing primarily uses genomic target sequences. It is understood that plasmid targets may also be important. For example, resistance to various antibiotics can be conferred by genes that are carried on plasmids. It is known that small differences in these sequences can affect the resistance conferred. In such an example, the exact species may be less important than identifying the plasmid-based gene, in which case the second-stage amplification and melting may focus primarily or exclusively on genes carried by plasmids. Accordingly, plasmid target sequences may be tested in a similar manner, with or without identifying the species or the strain.

REFERENCES

1. Wittwer C T, Fillmore G C, Garling D J. Minimizing the time required for DNA amplification by efficient heat transfer to small samples. Anal Biochem. 1990 May 1; 186(2):328-31.
2. Wittwer C T, Garling D J. Rapid cycle DNA amplification: time and temperature optimization. Biotechniques. 1991 January; 10(1):76-83.
3. Wittwer C T, Herrmann M G, Moss A A, Rasmussen R P. Continuous fluorescence monitoring of rapid cycle DNA amplification. Biotechniques. 1997 January; 22(1):130-1, 134-8.
4. Wittwer C T, Ririe K M, Andrew R V, David D A, Gundry R A, Balis U J. The LightCycler: a microvolume multi-sample fluorimeter with rapid temperature control. Biotechniques. 1997 January; 22(1):176-81
5. Gundry C N, Vandersteen J G, Reed G H, Pryor R J, Chen J, Wittwer C T. Amplicon melting analysis with labeled primers: a closed-tube method for differentiating homozygotes and heterozygotes. Clin Chem. 2003 March; 49(3): 396-406.
6. Wittwer C T, Reed G H, Gundry C N, Vandersteen J G, Pryor R J., High-resolution genotyping by amplicon melting analysis using LCGreen. Clin Chem. 2003 June; 49(6 Pt 1):853-60.
7. McKinney J T, Longo N, Hahn S, Matern D, Rinaldo P, Dobrowolski S F. Comprehensive analysis of the human medium chain acyl-CoA dehydrogenase gene. Mol Gen Metab. In press
8. Dobrowolski S F, Amat di San Filippo C, McKinney J T, Wilcken B, Longo N Identification of novel mutations in the SLC22A5 gene in primary carnitine deficiency with dye-binding/high-resolution thermal denaturation, Human Mutation, submitted
9. McKinney J T, Saunders C, Dobrowolski S F, High-resolution melting analysis of the human galactose-1-phosphate uridyl transferase gene, in preparation
10. http://www.defenselink.mil/contracts/2003/ct20030925.html
11. Poritz M A, Abbott R, Gerber T, Thatcher S, Bird A, Tuck A, Newswander A M, Belisle S, Ririe K, A Handheld, Battery-operated Real-time PCR Machine, American Society for Microbiology Annual Meeting, Baltimore Md., Mar. 9-12, 2003
12. Elnifro E M, Ashshi A M, Cooper R J, Klapper P E. Multiplex PCR: optimization and application in diagnostic virology. Clin Microbiol Rev. 2000 October; 13(4): 559-70. Review.
13. Elnifro E M, Cooper R J, Klapper P E, Yeo A C, Tullo A B. Multiplex polymerase chain reaction for diagnosis of viral and chlamydial keratoconjunctivitis. Invest Qphthalmol Vis Sci. 2000 June; 41(7):1818-22.
14. Giaever, G., et al. Genomic profiling of drug sensitivities via induced haploinsufficiency. Nature Genetics. 1999, 21, 278-283
15. Winzeler, E., et al Functional Characterization of the *Saccharomyces cerevisiae* Genome by Gene Deletion and Parallel Analysis. Science. 1999. 285, 901-906.
16. Sanchez et al., A multiplex assay with 52 single nucleotide polymorphisms for human identification. Electrophoresis. 2006 v27 p. 1713-24.
17. Zhou et al., Closed-tube genotyping with unlabeled oligonucleotide probes and a saturating DNA dye. Clin Chem. 2004 50 p. 1328-35.
18. Performance Standards for Antimicrobial Susceptibility Testing; Sixteenth Informational Supplement M100-S16. Volume 26 no 3: Clinical and Laboratory Standards Institute 2006.
19. Bradford P A. Extended-spectrum beta-lactamases in the 21st century: characterization, epidemiology, and detection of this important resistance threat. Clin Microbiol Rev. 2001 October; 14(4):933-51, table of contents.
20. Paterson D L. Resistance in gram-negative bacteria: Enterobacteriaceae. Am J Infect Control. 2006 June; 34(5 Suppl 1):S20-8; discussion S64-73.
21. van Leeuwen W B, Jay C, Snijders S, et al. Multilocus sequence typing of *Staphylococcus aureus* with DNA array technology. Journal of clinical microbiology 2003; 41:3323-6.
22. Hujer, et. al., Multi-drug Resistant *Acinetobacter* spp. Isolates from Military and Civilian Patients Treated at the Walter Reed Army Medical Center: Analysis of Antibiotic Resistance Genes. Antimicrob Agents Chemother. 2006 Sep. 25.
23. Huletsky A, Giroux R, Rossbach V, et al. New real-time PCR assay for rapid detection of methicillin-resistant *Staphylococcus aureus* directly from specimens containing a mixture of staphylococci. Journal of clinical microbiology 2004; 42:1875-84.
24. Stamper P D, Cai M, Howard T, Speser S, Carroll K C. Clinical Validation of the Molecular-Based BD GeneOhmTM StaphSR for the Direct Detection of *Staphylococcus aureus* and Methicillin-Resistant *Staphylococcus aureus* in Positive Blood Cultures. Journal of clinical microbiology 2007.
25. Cuny C, Witte W. PCR for the identification of methicillin-resistant *Staphylococcus aureus* (MRSA) strains using a single primer pair specific for SCCmec elements and the neighbouring chromosome-borne orfX. Clin Microbiol Infect 2005; 11:834-7.
26. Hagen R M, Seegmuller I, Navai J, Kappstein I, Lehn N, Miethke T. Development of a real-time PCR assay for rapid identification of methicillin-resistant *Staphylococcus aureus* from clinical samples. Int J Med Microbiol 2005; 295:77-86.

27. Bocchini C E, Hulten K G, Mason E O, Jr., Gonzalez B E, Hammerman W A, Kaplan S L. Panton-Valentine leukocidin genes are associated with enhanced inflammatory response and local disease in acute hematogenous *Staphylococcus aureus* osteomyelitis in children. Pediatrics 2006; 117:433-40.
28. Diep B A, Carleton H A, Chang R F, Sensabaugh Q F, Perdreau-Remington F. Roles of 34 virulence genes in the evolution of hospital- and community-associated strains of methicillin-resistant *Staphylococcus aureus*. The Journal of infectious diseases 2006; 193:1495-503.
29. Vandenesch F, Naimi T, Enright M C, et al. Community-acquired methicillin-resistant *Staphylococcus aureus* carrying Panton-Valentine leukocidin genes: worldwide emergence. Emerging infectious diseases 2003; 9:978-84.
30. Ma X X, It T, Chongtrakool P, Hiramatsu K. Predominance of clones carrying Panton-Valentine leukocidin genes among methicillin-resistant *Staphylococcus aureus* strains isolated in Japanese hospitals from 1979 to 1985. Journal of clinical microbiology 2006; 44:4515-27.
31. Deurenberg R H, Vink C, Driessen C, et al. Rapid detection of Panton-Valentine leukocidin from clinical isolates of *Staphylococcus aureus* strains by real-time PCR. FEW microbiology letters 2004; 240:225-8.
32. Johnsson D, Moiling P, Stralin K, Soderquist B. Detection of Panton-Valentine leukocidin gene in *Staphylococcus aureus* by LightCycler PCR: clinical and epidemiological aspects. Clin Microbiol Infect 2004; 10:884-9.
33. Fosheim G E, Carey R B, Limbago B M. Evaluation of the AdvanDx V R E EVIGENE assay for detection of vanA in vancomycin-resistant *Staphylococcus aureus*. Journal of clinical microbiology 207; 45:1611-3.
34. Hiramatsu K. Vancomycin resistance in staphylococci. Drug Resist Update 1998; 1:135-50.
35. Cookson B D, Robinson D A, Monk A B, et al. Evaluation of molecular typing methods in characterizing a European collection of epidemic methicillin-resistant *Staphylococcus aureus* strains: the HARMONY collection. Journal of clinical microbiology 2007; 45:1830-7.
36. Deurenberg R H, Vink C, Kalenic S, Friedrich A W, Bruggeman C A, Stobberingh E E. The molecular evolution of methicillin-resistant *Staphylococcus aureus*. Clin Microbiol Infect 2007; 13:222-35.
37. Chongtrakool P, Ito T, Ma X X, et al. Staphylococcal cassette chromosome mec (SCCmec) typing of methicillin-resistant *Staphylococcus aureus* strains isolated in 11 Asian countries: a proposal for a new nomenclature for SCCmec elements. Antimicrobial agents and chemotherapy 2006; 50:1001-12.
38. Boye K, Bartels M D, Andersen I S, Moller J A, Westh H. A new multiplex PCR for easy screening of methicillin-resistant *Staphylococcus aureus* SCCmec types I-V. Clin Microbiol Infect 2007; 13:725-7.
39. Francois P, Renzi G, Pittet D, et al. A novel multiplex real-time PCR assay for rapid typing of major staphylococcal cassette chromosome mec elements. Journal of clinical microbiology 2004; 42:3309-12.
40. Oliveira D C, de Lencastre H. Multiplex PCR strategy for rapid identification of structural types and variants of the mec element in methicillin-resistant *Staphylococcus aureus*. Antimicrobial agents and chemotherapy 2092; 46:2155-61.
41. Zhang K, McClure J A, Elsayed S, Louie T, Conly J M. Novel multiplex PCR assay for characterization and concomitant subtyping of staphylococcal cassette chromosome mec types Ito V in methicillin-resistant *Staphylococcus aureus*. Journal of clinical microbiology 2005; 43:5026-33.
42. Milheirico C, Oliveira D C, de Lencastre H. Update to the multiplex PCR strategy for the assignment of mec element types in *Staphylococcus aureus*. Antimicrobial agents and chemotherapy 2007.
43. Enright M C, Spratt B G. Multilocus sequence typing. Trends in microbiology 1999; 7:482-7.
44. Reed G H, Kent J O, Wittwer C T. High-resolution DNA melting analysis for simple and efficient molecular diagnostics. Pharmacogenomics 2007; 8:597-608.
45. Wittwer C T, Reed G H, Gundry C N, Vandersteen J G, Pryor R J. High-resolution genotyping by amplicon melting analysis using LCGreen. Clinical chemistry 2093; 49:853-60.
46. Vandersteen J G, Bayrak-Toydemir P, Palais R A, Wittwer C T. Identifying common genetic variants by high-resolution melting. Clinical chemistry 2007; 53:1191-8.
47. Palais R A, Liew M A, Wittwer C T. Quantitative heteroduplex analysis for single nucleotide polymorphism genotyping. Analytical biochemistry 2005; 346:167-75.
48. Dobrowolski S F, Angeletti J, Banas R A, Naylor E W. Real time PCR assays to detect common mutations in the biotinidase gene and application of mutational analysis to newborn screening for biotinidase deficiency. Molecular genetics and metabolism 2003; 78:100-7.
13. Enright M C, Day N P, Davies C E, Peacock S J, Spratt B G. Multilocus sequence typing for characterization of methicillin-resistant and methicillin-susceptible clones of *Staphylococcus aureus*. Journal of clinical microbiology 2000; 38:1008-15.

While references are made herein to PCR, it is understood that the devices and methods disclosed herein may be suitable for use with other nucleic acid amplification or other biological processing methods, as are known in the art, particularly methods that benefit from a first-stage multiplex reaction and a second-stage individual reaction. Illustrative non-limiting second-stage reactions include primer extension, including allele-specific primer extension; extension terminations, including termination by incorporation of one or more dideoxy nucleotides; incorporation of fluorescent or non-fluorescent labels; and other enzymatic reactions requiring a change in reaction mixture components or component ratios, such as asymmetric PCR, allele-specific PCR, invader assays, and other isothermal amplification or detection chemistries.

Although the invention has been described in detail with reference to preferred embodiments, variations and modifications exist within the scope and spirit of the invention as described and defined in the following claims.

What is claimed is:

1. A method for determining a crossing point (Cp) for each of second-stage amplicons in each of second-stage reaction wells from each of amplification curves, comprising the steps of:

obtaining a sample comprising a target nucleic acid of a specific species or strain of a bacterium, amplifying the target nucleic acid that is present in the sample in a first amplifying step, wherein said first amplifying step is performed in a reaction mixture comprising the target nucleic acid and a pair of first-stage primers, wherein each primer of the pair of first-stage primers hybridizes to a conserved region of a bacterial gene shared by various different bacterial species, thereby generating an amplified reaction mixture comprising a first-stage amplicon, dividing the amplified reaction mixture into a set of second-stage reaction wells, wherein the set of second-stage reaction wells comprises a plurality of the second-stage reaction wells, wherein each of the second-stage reaction wells of the plurality of the second-stage reaction wells comprises a different pair of second-stage primers configured to amplify the first-stage amplicon, and at least one primer of the different pair of second-stage primers in each of the second-stage reaction wells only specifically hybridizes to a variable region of the bacterial gene of one specific species or strain of bacterium of the various different bacterial species and wherein the at least one primer of the pair of second-stage primers is a nested primer of the first-stage primers, amplifying the amplified reaction mixture in each of the second-stage reaction wells by subjecting each of the second-stage reaction wells to amplification reactions in the presence of a fluorescent dye, thereby producing a plurality of second-stage amplicons in each of the second-stage reaction wells, wherein the second-stage amplicons comprise the nucleic acid sequences of the second-stage primers and the fluorescent dye, generating a plurality of amplification curves of the amplification reactions, wherein each of the amplification curves is generated by plotting the intensity of fluorescence generating from the fluorescent dye versus numbers of cycles of one of the amplification reactions, and determining the crossing point (Cp) for each of the second-stage amplicons in each of the second-stage reaction wells from each of the amplification curves.

2. The method of claim 1, wherein the bacterial gene is a housekeeping gene.

3. The method of claim 1, wherein the reaction mixture further comprises an additional pair of primers, wherein each primer of the additional pair of primers hybridizes to a different conserved region of a different target nucleic acid from the specific species or strain of the bacterium that may be present in the sample and the different conserved region is shared by various different bacterial species or strains, thereby generating an additional first-stage amplicon in the amplified reaction mixture, and the dividing step further comprises dividing the amplified reaction mixture into an additional set of the second-stage reaction wells, wherein the additional set of the second-stage reaction wells comprises a plurality of additional reaction wells, wherein each well of the plurality of the additional reaction wells comprises a different pair of primers configured to amplify the additional first-stage amplicon, and at least one primer of the different pair of primers in each of the additional reaction wells only specifically hybridizes to a variable region of the bacterial gene of one specific species or strain of bacterium of the various different bacterial species or strain, wherein the different pair of primers is different than the different pair of second-stage primers.

4. The method of claim 3, wherein the different pair of the second-stage primers in each of the reaction wells comprises a first primer and a second primer and the first primer hybridizes to the variable region of the bacterial gene of one specific species or strain of bacterium of the various different bacterial species or strain.

5. The method of claim 4, wherein the first primer in a first reaction well of the plurality of the second stage reaction wells comprises a nucleic acid sequence, wherein a 3'-end of the nucleic acid sequence only specifically hybridizes with a nucleic acid sequence of a specific species or strain of bacterium of the various different bacterial species or strain, wherein the nucleic acid sequence of the specific species or strain of bacterium encodes amino acids which are unique to the specific species or strain of bacterium such that the amplification reactions in the first reaction well of the plurality of the second stage reaction wells are prevented in conditions of the amplification reactions unless the target nucleic acid of the specific species or strain of the bacterium is present in the sample.

* * * * *

UNITED STATES PATENT AND TRADEMARK OFFICE
CERTIFICATE OF CORRECTION

PATENT NO. : 10,421,991 B2  
APPLICATION NO. : 14/938242  
DATED : September 24, 2019  
INVENTOR(S) : Blaschke-Bonkowsky et al.

Page 1 of 2

It is certified that error appears in the above-identified patent and that said Letters Patent is hereby corrected as shown below:

On the Title Page

Item (56): References Cited, OTHER PUBLICATIONS, Page 2, Column 1, 1st Dobrowolski et al. cite: Please correct "(200." to read -- (2003). --

Item (56): References Cited, OTHER PUBLICATIONS, Page 2, Column 2, Oliviera et al. cite: Please correct "46():" to read -- 46(7): --

In the Specification

Column 1, Line 27: Please correct "Jan. 20, 3016" to read -- Jan. 20, 2016 --

Column 4, Line 20: Please correct "1913 shoes" to read -- 19B shows --

Column 15, Line 46: Please correct "19Q" to read -- 19O --

Column 18, Line 13: Please correct "the "FIG. 8" blister" to read -- the "figure 8" blister --

Column 25, Line 36: Please correct "assembly 3Q 808" to read -- assembly 808 --

Column 26, Line 62: Please correct "29Q" to read -- 29O --

Column 28, Line 13: Please correct "824, 824, and 828" to read -- 824, 826, and 828 --

Column 28, Line 61: Please correct "5151" to read -- **515*l*** --

Column 32, Line 5: Please correct "51Q" to read -- 51O --

Column 45, Table 2, SEQ ID NO. 35: Please correct "rpoB1Efas .i102" to read -- rpoB1Efas .iR02 --

Signed and Sealed this  
Twenty-fifth Day of February, 2020

Andrei Iancu  
*Director of the United States Patent and Trademark Office*

Column 51, Table 5, SEQ ID NO. 78: Please correct "(SEQ ID NO. 78" to read -- (SEQ ID NO. 78) --

Column 59, Line 25: Please correct "Moiling P," to read -- Molling P, --

SEQUENCE LISTING

<160> NUMBER OF SEQ ID NOS: 82

<210> SEQ ID NO 1

<211> LENGTH: 19
<212> TYPE: DNA
<213> ORGANISM: Artificial
<220> FEATURE:
<223> OTHER INFORMATION: Baterial identification PCR primer sequence

<400> SEQUENCE: 1
ggcttygarg tdcgdgacg                                                19

<210> SEQ ID NO 2
<211> LENGTH: 18
<212> TYPE: DNA
<213> ORGANISM: Artificial
<220> FEATURE:
<223> OTHER INFORMATION: Baterial identification PCR primer sequence

<400> SEQUENCE: 2
rcccatbart gcrcggtt                                                 18

<210> SEQ ID NO 3
<211> LENGTH: 21
<212> TYPE: DNA
<213> ORGANISM: Artificial
<220> FEATURE:
<223> OTHER INFORMATION: Baterial identification PCR primer sequence

<400> SEQUENCE: 3
bcactayggb cgyatgtgtc c                                             21

<210> SEQ ID NO 4
<211> LENGTH: 20
<212> TYPE: DNA
<213> ORGANISM: Artificial
<220> FEATURE:
<223> OTHER INFORMATION: Baterial identification PCR primer sequence

<400> SEQUENCE: 4
aahggaatac atgcygtygc                                               20

<210> SEQ ID NO 5
<211> LENGTH: 17
<212> TYPE: DNA
<213> ORGANISM: Artificial
<220> FEATURE:
<223> OTHER INFORMATION: Baterial identification PCR primer sequence

<400> SEQUENCE: 5
tccggyggyy trcaygg                                                  17

<210> SEQ ID NO 6
<211> LENGTH: 20
<212> TYPE: DNA
<213> ORGANISM: Artificial
<220> FEATURE:
<223> OTHER INFORMATION: Baterial identification PCR primer sequence
<220> FEATURE:
<221> NAME/KEY: misc_feature
<222> LOCATION: (6)..(6)
<223> OTHER INFORMATION: n is a, c, g, or t

<400> SEQUENCE: 6
tcbgtngtwa acgccctgtc                                               20

<210> SEQ ID NO 7
<211> LENGTH: 21
<212> TYPE: DNA
<213> ORGANISM: Artificial

```
<220> FEATURE:
<223> OTHER INFORMATION: Baterial identification PCR primer sequence

<400> SEQUENCE: 7
rcgytghggr atgttrttgg t                                              21

<210> SEQ ID NO 8
<211> LENGTH: 23
<212> TYPE: DNA
<213> ORGANISM: Artificial
<220> FEATURE:
<223> OTHER INFORMATION: Baterial identification PCR primer sequence

<400> SEQUENCE: 8
ggyggwggyg gmtayaaggt ttc                                            23

<210> SEQ ID NO 9
<211> LENGTH: 23
<212> TYPE: DNA
<213> ORGANISM: Artificial
<220> FEATURE:
<223> OTHER INFORMATION: Baterial identification PCR primer sequence

<400> SEQUENCE: 9
ggmggyggcg gmtayaaagt atc                                            23

<210> SEQ ID NO 10
<211> LENGTH: 18
<212> TYPE: DNA
<213> ORGANISM: Artificial
<220> FEATURE:
<223> OTHER INFORMATION: Baterial identification PCR primer sequence

<400> SEQUENCE: 10
ttcatgcgta ccaccctc                                                  18

<210> SEQ ID NO 11
<211> LENGTH: 19
<212> TYPE: DNA
<213> ORGANISM: Artificial
<220> FEATURE:
<223> OTHER INFORMATION: Baterial identification PCR primer sequence

<400> SEQUENCE: 11
ccgtagyaaa ggcgaatcc                                                 19

<210> SEQ ID NO 12
<211> LENGTH: 21
<212> TYPE: DNA
<213> ORGANISM: Artificial
<220> FEATURE:
<223> OTHER INFORMATION: Baterial identification PCR primer sequence

<400> SEQUENCE: 12
ggtwacgtcc atgtagtcaa c                                              21

<210> SEQ ID NO 13
<211> LENGTH: 19
<212> TYPE: DNA
<213> ORGANISM: Artificial
<220> FEATURE:
<223> OTHER INFORMATION: Baterial identification PCR primer sequence

<400> SEQUENCE: 13
actttctgct tttgcacgt                                                 19
```

<210> SEQ ID NO 14
<211> LENGTH: 22
<212> TYPE: DNA
<213> ORGANISM: Artificial
<220> FEATURE:
<223> OTHER INFORMATION: Baterial identification PCR primer sequence

<400> SEQUENCE: 14
cttcagtaac ttgaccatca ac                                            22

<210> SEQ ID NO 15
<211> LENGTH: 19
<212> TYPE: DNA
<213> ORGANISM: Artificial
<220> FEATURE:
<223> OTHER INFORMATION: Baterial identification PCR primer sequence

<400> SEQUENCE: 15
ctcattgtcc gtttatgcg                                                19

<210> SEQ ID NO 16
<211> LENGTH: 21
<212> TYPE: DNA
<213> ORGANISM: Artificial
<220> FEATURE:
<223> OTHER INFORMATION: Baterial identification PCR primer sequence

<400> SEQUENCE: 16
tcgatttcct cggttacttt g                                             21

<210> SEQ ID NO 17
<211> LENGTH: 17
<212> TYPE: DNA
<213> ORGANISM: Artificial
<220> FEATURE:
<223> OTHER INFORMATION: Baterial identification PCR primer sequence

<400> SEQUENCE: 17
tcaactccct ggcgacc                                                  17

<210> SEQ ID NO 18
<211> LENGTH: 15
<212> TYPE: DNA
<213> ORGANISM: Artificial
<220> FEATURE:
<223> OTHER INFORMATION: Baterial identification PCR primer sequence

<400> SEQUENCE: 18
cyacgcggta cgggc                                                    15

<210> SEQ ID NO 19
<211> LENGTH: 19
<212> TYPE: DNA
<213> ORGANISM: Artificial
<220> FEATURE:
<223> OTHER INFORMATION: Baterial identification PCR primer sequence

<400> SEQUENCE: 19
aggttgaccg tgaaacagg                                                19

<210> SEQ ID NO 20
<211> LENGTH: 19
<212> TYPE: DNA
<213> ORGANISM: Artificial
<220> FEATURE:
<223> OTHER INFORMATION: Baterial identification PCR primer sequence

<400> SEQUENCE: 20
aggttgaccg tgcaactgg                                              19

<210> SEQ ID NO 21
<211> LENGTH: 21
<212> TYPE: DNA
<213> ORGANISM: Artificial
<220> FEATURE:
<223> OTHER INFORMATION: Baterial identification PCR primer sequence

<400> SEQUENCE: 21
gctggatact cttggttgac c                                           21

<210> SEQ ID NO 22
<211> LENGTH: 21
<212> TYPE: DNA
<213> ORGANISM: Artificial
<220> FEATURE:
<223> OTHER INFORMATION: Baterial identification PCR primer sequence

<400> SEQUENCE: 22
gctggatatt cttggttaac c                                           21

<210> SEQ ID NO 23
<211> LENGTH: 22
<212> TYPE: DNA
<213> ORGANISM: Artificial
<220> FEATURE:
<223> OTHER INFORMATION: Baterial identification PCR primer sequence

<400> SEQUENCE: 23
ygaagaagac gartacacag tt                                          22

<210> SEQ ID NO 24
<211> LENGTH: 21
<212> TYPE: DNA
<213> ORGANISM: Artificial
<220> FEATURE:
<223> OTHER INFORMATION: Baterial identification PCR primer sequence

<400> SEQUENCE: 24
cgtcaacgaa atcaacaaca c                                           21

<210> SEQ ID NO 25
<211> LENGTH: 22
<212> TYPE: DNA
<213> ORGANISM: Artificial
<220> FEATURE:
<223> OTHER INFORMATION: Baterial identification PCR primer sequence

<400> SEQUENCE: 25
tgaagaagat gaatttacag tt                                          22

<210> SEQ ID NO 26
<211> LENGTH: 21
<212> TYPE: DNA
<213> ORGANISM: Artificial
<220> FEATURE:
<223> OTHER INFORMATION: Baterial identification PCR primer sequence

<400> SEQUENCE: 26
cgtcaacaaa gtcaacaatg c                                           21

<210> SEQ ID NO 27

<211> LENGTH: 25
<212> TYPE: DNA
<213> ORGANISM: Artificial
<220> FEATURE:
<223> OTHER INFORMATION: Baterial identification PCR primer sequence

<400> SEQUENCE: 27
gtaaagttga tttagataca catgc                                    25

<210> SEQ ID NO 28
<211> LENGTH: 23
<212> TYPE: DNA
<213> ORGANISM: Artificial
<220> FEATURE:
<223> OTHER INFORMATION: Baterial identification PCR primer sequence

<400> SEQUENCE: 28
cgacatacaa cttcatcatc cat                                      23

<210> SEQ ID NO 29
<211> LENGTH: 25
<212> TYPE: DNA
<213> ORGANISM: Artificial
<220> FEATURE:
<223> OTHER INFORMATION: Baterial identification PCR primer sequence

<400> SEQUENCE: 29
ytwgatgaaa atggtcgttt cytag                                    25

<210> SEQ ID NO 30
<211> LENGTH: 21
<212> TYPE: DNA
<213> ORGANISM: Artificial
<220> FEATURE:
<223> OTHER INFORMATION: Baterial identification PCR primer sequence

<400> SEQUENCE: 30
gtttwggwga tacrtccatg t                                        21

<210> SEQ ID NO 31
<211> LENGTH: 23
<212> TYPE: DNA
<213> ORGANISM: Artificial
<220> FEATURE:
<223> OTHER INFORMATION: Baterial identification PCR primer sequence

<400> SEQUENCE: 31
ckaactcgaa attagacgaa caa                                      23

<210> SEQ ID NO 32
<211> LENGTH: 23
<212> TYPE: DNA
<213> ORGANISM: Artificial
<220> FEATURE:
<223> OTHER INFORMATION: Baterial identification PCR primer sequence

<400> SEQUENCE: 32
ttttctaccg ctaagttttc tga                                      23

<210> SEQ ID NO 33
<211> LENGTH: 20
<212> TYPE: DNA
<213> ORGANISM: Artificial
<220> FEATURE:
<223> OTHER INFORMATION: Baterial identification PCR primer sequence

<400> SEQUENCE: 33

```
acagcygaya tcgaagacca                                          20

<210> SEQ ID NO 34
<211> LENGTH: 23
<212> TYPE: DNA
<213> ORGANISM: Artificial
<220> FEATURE:
<223> OTHER INFORMATION: Baterial identification PCR primer sequence

<400> SEQUENCE: 34
acttctaagt tttcactttg hgc                                      23

<210> SEQ ID NO 35
<211> LENGTH: 23
<212> TYPE: DNA
<213> ORGANISM: Artificial
<220> FEATURE:
<223> OTHER INFORMATION: Baterial identification PCR primer sequence

<400> SEQUENCE: 35
acttctaagt tttcactttg tag                                      23

<210> SEQ ID NO 36
<211> LENGTH: 18
<212> TYPE: DNA
<213> ORGANISM: Artificial
<220> FEATURE:
<223> OTHER INFORMATION: Baterial identification PCR primer sequence

<400> SEQUENCE: 36
attcgtcgtc aaggtcac                                            18

<210> SEQ ID NO 37
<211> LENGTH: 19
<212> TYPE: DNA
<213> ORGANISM: Artificial
<220> FEATURE:
<223> OTHER INFORMATION: Baterial identification PCR primer sequence

<400> SEQUENCE: 37
cgattgaggc tcccctaaa                                           19

<210> SEQ ID NO 38
<211> LENGTH: 19
<212> TYPE: DNA
<213> ORGANISM: Artificial
<220> FEATURE:
<223> OTHER INFORMATION: Baterial identification PCR primer sequence

<400> SEQUENCE: 38
gttatccagc gcgagggta                                           19

<210> SEQ ID NO 39
<211> LENGTH: 19
<212> TYPE: DNA
<213> ORGANISM: Artificial
<220> FEATURE:
<223> OTHER INFORMATION: Baterial identification PCR primer sequence

<400> SEQUENCE: 39
gtgccggttt tttcagtct                                           19

<210> SEQ ID NO 40
<211> LENGTH: 24
<212> TYPE: DNA
```

```
<213> ORGANISM: Artificial
<220> FEATURE:
<223> OTHER INFORMATION: Baterial identification PCR primer sequence

<400> SEQUENCE: 40
gataacaaag ttcacaagca gatg                                          24

<210> SEQ ID NO 41
<211> LENGTH: 17
<212> TYPE: DNA
<213> ORGANISM: Artificial
<220> FEATURE:
<223> OTHER INFORMATION: Baterial identification PCR primer sequence

<400> SEQUENCE: 41
gtcggtttcg ccagtca                                                  17

<210> SEQ ID NO 42
<211> LENGTH: 19
<212> TYPE: DNA
<213> ORGANISM: Artificial
<220> FEATURE:
<223> OTHER INFORMATION: Baterial identification PCR primer sequence

<400> SEQUENCE: 42
gtttctggcc gagctayga                                                19

<210> SEQ ID NO 43
<211> LENGTH: 21
<212> TYPE: DNA
<213> ORGANISM: Artificial
<220> FEATURE:
<223> OTHER INFORMATION: Baterial identification PCR primer sequence

<400> SEQUENCE: 43
cgttttgcca gratytcgta t                                             21

<210> SEQ ID NO 44
<211> LENGTH: 17
<212> TYPE: DNA
<213> ORGANISM: Artificial
<220> FEATURE:
<223> OTHER INFORMATION: Baterial identification PCR primer sequence

<400> SEQUENCE: 44
tatccagcgc gaaggca                                                  17

<210> SEQ ID NO 45
<211> LENGTH: 17
<212> TYPE: DNA
<213> ORGANISM: Artificial
<220> FEATURE:
<223> OTHER INFORMATION: Baterial identification PCR primer sequence

<400> SEQUENCE: 45
ggccagaaac gcaccat                                                  17

<210> SEQ ID NO 46
<211> LENGTH: 19
<212> TYPE: DNA
<213> ORGANISM: Artificial
<220> FEATURE:
<223> OTHER INFORMATION: Baterial identification PCR primer sequence

<400> SEQUENCE: 46
aacacttcgt ccgcttcgt                                                19
```

<210> SEQ ID NO 47
<211> LENGTH: 17
<212> TYPE: DNA
<213> ORGANISM: Artificial
<220> FEATURE:
<223> OTHER INFORMATION: Baterial identification PCR primer sequence

<400> SEQUENCE: 47
gcgaggaagc gcacggt                                                      17

<210> SEQ ID NO 48
<211> LENGTH: 18
<212> TYPE: DNA
<213> ORGANISM: Artificial
<220> FEATURE:
<223> OTHER INFORMATION: Baterial identification PCR primer sequence

<400> SEQUENCE: 48
tcgccacaac aaggtctg                                                     18

<210> SEQ ID NO 49
<211> LENGTH: 18
<212> TYPE: DNA
<213> ORGANISM: Artificial
<220> FEATURE:
<223> OTHER INFORMATION: Baterial identification PCR primer sequence

<400> SEQUENCE: 49
ggccaggatg tcccarct                                                     18

<210> SEQ ID NO 50
<211> LENGTH: 24
<212> TYPE: DNA
<213> ORGANISM: Artificial
<220> FEATURE:
<223> OTHER INFORMATION: Baterial identification PCR primer sequence

<400> SEQUENCE: 50
gtcattcgtt ttaaagcaga tgga                                              24

<210> SEQ ID NO 51
<211> LENGTH: 23
<212> TYPE: DNA
<213> ORGANISM: Artificial
<220> FEATURE:
<223> OTHER INFORMATION: Baterial identification PCR primer sequence

<400> SEQUENCE: 51
gtgataggag tcttctctaa cgt                                               23

<210> SEQ ID NO 52
<211> LENGTH: 19
<212> TYPE: DNA
<213> ORGANISM: Artificial
<220> FEATURE:
<223> OTHER INFORMATION: Baterial identification PCR primer sequence

<400> SEQUENCE: 52
agaataccgt cgtggtcat                                                    19

<210> SEQ ID NO 53
<211> LENGTH: 18
<212> TYPE: DNA
<213> ORGANISM: Artificial
<220> FEATURE:

-continued

<223> OTHER INFORMATION: Baterial identification PCR primer sequence

<400> SEQUENCE: 53
accttggcgc ttatctgt                                                 18

<210> SEQ ID NO 54
<211> LENGTH: 23
<212> TYPE: DNA
<213> ORGANISM: Artificial
<220> FEATURE:
<223> OTHER INFORMATION: Baterial identification PCR primer sequence

<400> SEQUENCE: 54
aacgactcag tttgattaca gtg                                           23

<210> SEQ ID NO 55
<211> LENGTH: 24
<212> TYPE: DNA
<213> ORGANISM: Artificial
<220> FEATURE:
<223> OTHER INFORMATION: Baterial identification PCR primer sequence

<400> SEQUENCE: 55
aaatgttctt cttgttccat acct                                          24

<210> SEQ ID NO 56
<211> LENGTH: 26
<212> TYPE: DNA
<213> ORGANISM: Artificial
<220> FEATURE:
<223> OTHER INFORMATION: Baterial identification PCR primer sequence

<400> SEQUENCE: 56
gyaaggttca ttatcaagaa taycaa                                        26

<210> SEQ ID NO 57
<211> LENGTH: 24
<212> TYPE: DNA
<213> ORGANISM: Artificial
<220> FEATURE:
<223> OTHER INFORMATION: Baterial identification PCR primer sequence

<400> SEQUENCE: 57
aagtgaactg ttgttcctga taag                                          24

<210> SEQ ID NO 58
<211> LENGTH: 23
<212> TYPE: DNA
<213> ORGANISM: Artificial
<220> FEATURE:
<223> OTHER INFORMATION: Baterial identification PCR primer sequence

<400> SEQUENCE: 58
gctattcgat tcaaagccga taa                                           23

<210> SEQ ID NO 59
<211> LENGTH: 27
<212> TYPE: DNA
<213> ORGANISM: Artificial
<220> FEATURE:
<223> OTHER INFORMATION: Baterial identification PCR primer sequence

<400> SEQUENCE: 59
tctaacttcc tcttctcttt catcttt                                       27

```
<210> SEQ ID NO 60
<211> LENGTH: 24
<212> TYPE: DNA
<213> ORGANISM: Artificial
<220> FEATURE:
<223> OTHER INFORMATION: Baterial identification PCR primer sequence

<400> SEQUENCE: 60
cgtcgtgaag gacaagaaga taaa                                           24

<210> SEQ ID NO 61
<211> LENGTH: 20
<212> TYPE: DNA
<213> ORGANISM: Artificial
<220> FEATURE:
<223> OTHER INFORMATION: Baterial identification PCR primer sequence

<400> SEQUENCE: 61
cttgttgctc tccttcaatg                                                20

<210> SEQ ID NO 62
<211> LENGTH: 23
<212> TYPE: DNA
<213> ORGANISM: Artificial
<220> FEATURE:
<223> OTHER INFORMATION: Baterial identification PCR primer sequence

<400> SEQUENCE: 62
ccaatttatt tggaaggtga acg                                            23

<210> SEQ ID NO 63
<211> LENGTH: 25
<212> TYPE: DNA
<213> ORGANISM: Artificial
<220> FEATURE:
<223> OTHER INFORMATION: Baterial identification PCR primer sequence

<400> SEQUENCE: 63
gcgaatgaaa tgatrttgct tgaga                                          25

<210> SEQ ID NO 64
<211> LENGTH: 19
<212> TYPE: DNA
<213> ORGANISM: Artificial
<220> FEATURE:
<223> OTHER INFORMATION: Baterial identification PCR primer sequence

<400> SEQUENCE: 64
actccaacct ggatgaaga                                                 19

<210> SEQ ID NO 65
<211> LENGTH: 18
<212> TYPE: DNA
<213> ORGANISM: Artificial
<220> FEATURE:
<223> OTHER INFORMATION: Baterial identification PCR primer sequence

<400> SEQUENCE: 65
acgtccatgt agtcaacc                                                  18

<210> SEQ ID NO 66
<211> LENGTH: 22
<212> TYPE: DNA
<213> ORGANISM: Artificial
<220> FEATURE:
<223> OTHER INFORMATION: Baterial identification PCR primer sequence
```

```
<400> SEQUENCE: 66
gaactccaac ctggatgaaa ac                                                22

<210> SEQ ID NO 67
<211> LENGTH: 19
<212> TYPE: DNA
<213> ORGANISM: Artificial
<220> FEATURE:
<223> OTHER INFORMATION: Baterial identification PCR primer sequence

<400> SEQUENCE: 67
actccaacct ggatgacga                                                   19

<210> SEQ ID NO 68
<211> LENGTH: 19
<212> TYPE: DNA
<213> ORGANISM: Artificial
<220> FEATURE:
<223> OTHER INFORMATION: Baterial identification PCR primer sequence

<400> SEQUENCE: 68
tcgcyacccg tctggaata                                                   19

<210> SEQ ID NO 69
<211> LENGTH: 20
<212> TYPE: DNA
<213> ORGANISM: Artificial
<220> FEATURE:
<223> OTHER INFORMATION: Baterial identification PCR primer sequence

<400> SEQUENCE: 69
cgtctttmgg rtccakgttg                                                  20

<210> SEQ ID NO 70
<211> LENGTH: 20
<212> TYPE: DNA
<213> ORGANISM: Artificial
<220> FEATURE:
<223> OTHER INFORMATION: Baterial identification PCR primer sequence

<400> SEQUENCE: 70
gtctggaata ccagtggacc                                                  20

<210> SEQ ID NO 71
<211> LENGTH: 17
<212> TYPE: DNA
<213> ORGANISM: Artificial
<220> FEATURE:
<223> OTHER INFORMATION: Baterial identification PCR primer sequence

<400> SEQUENCE: 71
ctgatccaga gcagcct                                                     17

<210> SEQ ID NO 72
<211> LENGTH: 18
<212> TYPE: DNA
<213> ORGANISM: Artificial
<220> FEATURE:
<223> OTHER INFORMATION: Baterial identification PCR primer sequence

<400> SEQUENCE: 72
cggtcaggaa gatgctgc                                                    18

<210> SEQ ID NO 73
<211> LENGTH: 19
```

```
<212> TYPE: DNA
<213> ORGANISM: Artificial
<220> FEATURE:
<223> OTHER INFORMATION: Baterial identification PCR primer sequence

<400> SEQUENCE: 73
ggtgaagtgc ttggtagcc                                                    19

<210> SEQ ID NO 74
<211> LENGTH: 19
<212> TYPE: DNA
<213> ORGANISM: Artificial
<220> FEATURE:
<223> OTHER INFORMATION: Baterial identification PCR primer sequence

<400> SEQUENCE: 74
cggtcaggaa gatgttgct                                                    19

<210> SEQ ID NO 75
<211> LENGTH: 24
<212> TYPE: DNA
<213> ORGANISM: Artificial
<220> FEATURE:
<223> OTHER INFORMATION: Baterial identification PCR primer sequence

<400> SEQUENCE: 75
tgaccttctg gtttcagagt agat                                              24

<210> SEQ ID NO 76
<211> LENGTH: 17
<212> TYPE: DNA
<213> ORGANISM: Artificial
<220> FEATURE:
<223> OTHER INFORMATION: Baterial identification PCR primer sequence

<400> SEQUENCE: 76
aacatcggcg acggcaa                                                      17

<210> SEQ ID NO 77
<211> LENGTH: 18
<212> TYPE: DNA
<213> ORGANISM: Artificial
<220> FEATURE:
<223> OTHER INFORMATION: Baterial identification PCR primer sequence

<400> SEQUENCE: 77
gctggagcaa cgattggc                                                     18

<210> SEQ ID NO 78
<211> LENGTH: 29
<212> TYPE: DNA
<213> ORGANISM: Artificial
<220> FEATURE:
<223> OTHER INFORMATION: Baterial identification PCR primer sequence

<400> SEQUENCE: 78
acttggttga gtactcacca gtcacagaa                                         29

<210> SEQ ID NO 79
<211> LENGTH: 29
<212> TYPE: DNA
<213> ORGANISM: Artificial
<220> FEATURE:
<223> OTHER INFORMATION: Baterial identification PCR primer sequence

<400> SEQUENCE: 79
```

-continued

```
acttggttaa gtactcacca gtcacagaa                                              29

<210> SEQ ID NO 80
<211> LENGTH: 28
<212> TYPE: DNA
<213> ORGANISM: Artificial
<220> FEATURE:
<223> OTHER INFORMATION: Baterial identification PCR primer sequence

<400> SEQUENCE: 80
ccttgatcgt tgggaaccgg agctgaat                                               28

<210> SEQ ID NO 81
<211> LENGTH: 28
<212> TYPE: DNA
<213> ORGANISM: Artificial
<220> FEATURE:
<223> OTHER INFORMATION: Baterial identification PCR primer sequence

<400> SEQUENCE: 81
ccttgatagt tgggaaccgg agctgaat                                               28

<210> SEQ ID NO 82
<211> LENGTH: 18
<212> TYPE: DNA
<213> ORGANISM: Artificial
<220> FEATURE:
<223> OTHER INFORMATION: Baterial identification PCR primer sequence

<400> SEQUENCE: 82
ttcrtgmgth ccdccttc                                                          18
```